(12) United States Patent
Reed et al.

(10) Patent No.: US 10,982,234 B2
(45) Date of Patent: Apr. 20, 2021

(54) MICROORGANISMS THAT CO-CONSUME GLUCOSE WITH NON-GLUCOSE CARBOHYDRATES AND METHODS OF USE

(71) Applicant: WISCONSIN ALUMNI RESEARCH FOUNDATION, Madison, WI (US)

(72) Inventors: Jennifer L. Reed, Madison, WI (US); Joonhoon Kim, Busan (KR)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 16/379,433

(22) Filed: Apr. 9, 2019

(65) Prior Publication Data

US 2019/0264238 A1 Aug. 29, 2019

Related U.S. Application Data

(62) Division of application No. 14/791,590, filed on Jul. 6, 2015, now Pat. No. 10,301,653.

(51) Int. Cl.
  *C12N 1/20* (2006.01)
  *C12P 7/06* (2006.01)
  (Continued)

(52) U.S. Cl.
  CPC ............ *C12P 7/065* (2013.01); *C07K 14/245* (2013.01); *C12N 1/14* (2013.01); *C12N 1/20* (2013.01);
  (Continued)

(58) Field of Classification Search
  None
  See application file for complete search history.

(56) References Cited

U.S. PATENT DOCUMENTS 4,837,148 A 6/1989 Cregg
4,929,555 A 5/1990 Cregg et al.
(Continued)

OTHER PUBLICATIONS

Jeppsson et al., "Reduced oxidative pentose phosphate pathway flux in recombinant xylose-utilizing *Saccharomyces cerevisiae* strains improves the ethanol yield from xylose", Applied Environmental Microbiology, vol. 68, No. 4, pp. 1604-1609, 2002 (Year: 2002).*
(Continued)

*Primary Examiner* — Richard C Ekstrom
(74) *Attorney, Agent, or Firm* — Daniel A. Blasiole; DeWitt LLP

(57) ABSTRACT

Microorganisms that co-consume glucose with non-glucose carbohydrates, such as xylose, and methods of using same. The microorganisms comprise modifications that reduce or ablate the activity of a phosphoenolpyruvate (PEP):carbohydrate phosphotransferase system (PTS) protein or modifications that reduce or ablate the activity of a phosphoglucose isomerase and a GntR. The PTS protein may be selected from an enzyme I (EI), an HPr, an FPr, and an enzyme $II^{Glc}$ ($EII^{Glc}$). Additional modifications include reduction or ablation of the activity of a pyruvate formate lyase, a lactate dehydrogenase, and a fumarate reductase and inclusion of recombinant pyruvate decarboxylase and alcohol dehydrogenase genes. The microorganisms are particularly suited to co-consuming glucose and xylose in media containing these substrates and producing ethanol therefrom.

16 Claims, 20 Drawing Sheets

Specification includes a Sequence Listing.

(51) Int. Cl.
| | |
|---|---|
| *C12P 7/10* | (2006.01) |
| *C12N 9/88* | (2006.01) |
| *C12N 9/04* | (2006.01) |
| *C12N 1/14* | (2006.01) |
| *C07K 14/245* | (2006.01) |
| *C12N 9/12* | (2006.01) |
| *C12N 9/92* | (2006.01) |

(52) U.S. Cl.
CPC ......... *C12N 9/0006* (2013.01); *C12N 9/1205* (2013.01); *C12N 9/88* (2013.01); *C12N 9/92* (2013.01); *C12P 7/06* (2013.01); *C12P 7/10* (2013.01); *C12Y 101/01001* (2013.01); *C12Y 401/01001* (2013.01); *Y02E 50/10* (2013.01)

(56) References Cited

U.S. PATENT DOCUMENTS

| | | | |
|---|---|---|---|
| 9,187,772 | B2 | 11/2015 | Zhang |
| 9,260,729 | B2 | 2/2016 | Sun |
| 9,605,280 | B2 | 3/2017 | Zhang |
| 10,301,653 | B2* | 5/2019 | Reed ............... C12N 9/92 |
| 2010/0255553 | A1 | 10/2010 | Srienc |
| 2011/0014666 | A1 | 1/2011 | Voelker |
| 2011/0165660 | A1* | 7/2011 | Picataggio ............... C12P 7/10 435/254.21 |
| 2011/0195464 | A1 | 8/2011 | Preston |
| 2012/0058530 | A1 | 3/2012 | Zhang |
| 2012/0308991 | A1 | 12/2012 | Eiteman |
| 2013/0157319 | A1 | 6/2013 | Chao |
| 2013/0157330 | A1 | 6/2013 | Zhang |
| 2013/0323766 | A1 | 12/2013 | Sillers |
| 2014/0248669 | A1 | 9/2014 | Marliere |
| 2015/0225745 | A1 | 8/2015 | Vroom |
| 2015/0232903 | A1* | 8/2015 | Hiidesaki ............... C12N 15/52 435/92 |
| 2016/0083752 | A1 | 3/2016 | Burgard |
| 2016/0083753 | A1 | 3/2016 | Grabar |
| 2016/0097064 | A1 | 4/2016 | Zhang |
| 2016/0130618 | A1* | 5/2016 | Hara ............... C12P 13/04 435/107 |
| 2016/0145648 | A1 | 5/2016 | Zhang |
| 2016/0160245 | A1 | 6/2016 | Yocum |
| 2016/0230198 | A1 | 8/2016 | Vemuri |
| 2016/0326553 | A1 | 11/2016 | Burgard |
| 2017/0073665 | A1 | 3/2017 | Krawczyk |
| 2017/0183694 | A1 | 6/2017 | Pharkya |
| 2019/0264238 | A1* | 8/2019 | Reed ............... C12N 1/20 |

OTHER PUBLICATIONS

Jeppsson et al., "Reduced oxidative pentose phosphate pathway flux in recombinant xylose-utilizing *Saccharomyces cerevisiae* strains improves the ethanol yield from xylose", Applied and Environmental Microbiology, vol. 68, No. 4, pp. 1604-1609, 2002 (Year: 2002).*

Alpert et al., 1985. The bacterial phosphoenolpyruvate-dependent phosphotransferase system. Isolation of active site peptides by reversed-phase high performance liquid chromatography and determination of their primary structure. *J. Chromatogr.* 326:363-371.

Alpert et al., 1985. Phosphoenolpyruvate-dependent protein kinase Enzyme I of *Streptococcus faecalis*. Purification and properties of the enzyme and characterization of its active center. *Biochemistry* 24:959-964.

Anderson et al., 1971. Sugar transport. III. Purification and properties of a phosphocarrier protein of the phosphoenolpyruvate-dependent phosphotransferase system of *Escherichia coli*. *J. Biol. Chem.* 246:7023-7033.

Baba et al., 2006. Construction of *Escherichia coli* K-12 in-frame, single-gene knockout mutants: the Keio collection. *Mol Syst Biol*, 2: p. 2006 0008.

Balderas-Hernández et al., 2011. A. Adaptive evolution of *Escherichia coli* inactivated in the phosphotransferase system operon improves co-utilization of xylose and glucose under anaerobic conditions, *Appl Biochem Biotechnol*, Feb.;163(4):485-96.

Barua et al., An automated phenotype-driven approach (GeneForce) for refining metabolic and regulatory models. *PLoS Comput Biol*, 2010. 6(10): p. e1000970.

Beneski et al., 1982. Sugar transport by the bacterial phosphotransferase system. Isolation and characterization of a phosphocarrier protein HPr from wild type and mutants of *Salmonella typhimurium*, *J. Biol. Chem.* 257:14492-14498.

Beyreuther et al., 1977. The phosphoenolpyruvate-dependent phosphotransferase system of *Staphylococcus aureus*. 1. Aminoacid sequence of the phosphocarrier protein HPr. *Eur. J. Biochem.* 75:275-286.

Binder et al., Fermentable sugars by chemical hydrolysis of biomass, *Proc Natl Acad Sci U S A*. Mar. 9, 2010;107(10):4516-21.

Blatch et al., 1990. Nucleotide sequence and analysis of the *Vibrio alginolyticus* sucrose uptake-encoding region. Gene 95:17-23.

Boos et al., 1990. Trehalose transport and metabolism in *Escherichia coli*. *J. Bacteriol.* 172:3450-3461.

Bramley et al., 1987. Sequence homologies between proteins of bacterial phosphoenolpyruvate-dependent sugar phosphotransferase systems: identification of possible phosphate-carrying histidine residues, *Proc. Natl. Acad. Sci. USA* 84:4777-4780.

Byrne et al., 1988. DNA sequences of the cysK regions of *Salmonella typhimurium* and *Escherichia coli* and linkage of the cysK regions to *ptsH*. *J. Bacteriol.* 170:3150-3157.

Covert et al., Integrating high-throughput and computational data elucidates bacterial networks. *Nature*, 2004. 429(6987): p. 92-6.

Da Costa et al., Ionic Liquids as a tool for lignocellulosic biomass fractionation. *Sustainable Chemical Processes*, 2013. 1(3):1-31.

Datsenko et al., One-step inactivation of chromosomal genes in *Escherichia coli* K-12 using PCR products. *Proc Natl Acad Sci U S A*. Jun. 6, 2000 ;97(12):6640-5.

De Reuse et al., 1988. The ptsH, ptsI, and crr genes of the *Escherichia coli* phosphoenolpyruvate-dependent phosphotransferase system: a complex operon with several modes of transcription. *J. Bacteriol.* 170:3827-3837.

Deutscher et al., 1986. Streptococcal phosphoenolpyruvate:sugar phosphotransferase system: amino acid sequence and site of ATP-dependent phosphorylation of HPr. *Biochemistry* 25:6543-6551.

Dooijewaard et al., 1979. *Escherichia coli* phosphoenolpyruvate dependent phosphotransferase system. Copurification of HPr and α1-6 glucan. *Biochemistry* 18:2990-2996.

Ebner et al., 1988. DNA sequence of the gene serA encoding the sucrose transport protein Enzyme$^{Scr}$ of the phosphotransferase system from enteric bacteria: homology of the Enzyme II$^{Scr}$ and Enzyme II$^{Bgl}$ proteins. *Mol. Microbiol.* 2:9-17.

Eisermann et al., 1991. Staphylococcal phosphoenolpyruvate-dependent phosphotransferase system. Purification and protein sequencing of the *Staphylococcus carnosus* histidine-containing protein, and cloning and DNA sequencing of the ptsH gene. *Eur. J. Biochem.* 197:9-14.

El Hassouni et al., 1992. Nucleotide sequence of the arb genes, which control β-glucoside utilization in *Erwinia chrysanthemi*: comparison with the *Escherichia coli* bgl operon and evidence for a new β-glycohydrolase family including enzymes from eubacteria, archaebacteria, and humans, *J. Bacteriol.* 174:765-777.

Erni et al., 1986. Glucose permease of the bacterial phosphotransferase system. Gene cloning, overproduction, and amino acid sequence of enzyme II$^{Glc}$. *J. Biol. Chem.* 261:16398-16403.

Feist et al., A genome-scale metabolic reconstruction for *Escherichia coli* K-12 MG1655 that accounts for 1260 ORFs and thermodynamic information. *Mol Syst Biol*, 2007. 3: p. 121.

Feldheim et al., Physiological consequences of the complete loss of phosphoryl-transfer proteins HPr and FPr of the phosphoenolpyruvate:sugar phosphotransferase system and analysis of fructose (fru) operon expression in *Salmonella typhimurium*. *J. Bacteriol.* Sep. 1990; 172(9):5459-69.

(56) References Cited

OTHER PUBLICATIONS

Fouet et al., 1987. *Bacillus subtilis* sucrose-specific enzyme II of the phosphotransferase system: expression in *Escherichia coli* and homology to enzymes II from enteric bacteria. *Proc. Natl. Acad. Sci. USA* 84:8773-8777.

Gagnon et al., 1992. Cloning, sequencing, and expression in *Escherichia coli* of the ptsI gene encoding enzyme I of the phosphoenolpyruvate:sugar phosphotransferase transport system from *Streptococcus salivarius*. *Gene* 121:71-78.

Gardner et al., 2010. Requirement of the type II secretion system for utilization of cellulosic substrates by *Cellvibrio japonicus*. *Appl. Environ. Microbiol*. 76:5079-5087.

Geerse et al., 1986. Relationship between pseudo-HPr and the PEP: fructose phosphotransferase system in *Salmonella typhimurium* and *Escherichia coli*. *Mol. Gen. Genet*. 203:435-444.

Geerse et al., 1989. The PEP: fructose phosphotransferase system in *Salmonella typhimurium*: FPr combines enzyme $III^{Fru}$ and pseudo-HPr activities. *Mol. Gen. Genet* 216(2-3):517-25.

Gonzy-Tréboul et al., 1991. The glucose permease of the phosphotransferase system of *Bacillus subtilis*: evidence for II01c and III01c domains. *Mol. Microbiol*. 5:1241-1249.

Gonzy-Tréboul et al., 1989. Phosphoenolpyruvate:sugar phosphotransferase system of *Bacillus subtilis*: nucleotide sequence of ptsX, ptsH, and the 5'-end of ptsI and evidence for a ptsHI operon. *Mol. Microbiol*. 3:103-112.

Hall et al., 1992. Nucleotide sequence, function, activation, and evolution of the cryptic asc operon of *Escherichia coli* K12. *Mol. Biol. Evol*. 9:688-706.

Jaffor et al., 1977, Mycoplasma phosphoenolpyruvate-dependent sugar phosphotransferase system: purification and characterization of enzyme I. *J. Bacteriol*. 131:988-996.

Jaffor et al., 1976. Mycoplasma phosphoenolpyruvate-dependent sugar phosphotransferase system: purification and characterization of the phosphocarrier protein. *J. Bacteriol*. 127:1298-1306.

Jenkinson et al., 1989. Properties of a phosphocarrier protein (HPr) extracted from intact cells of *Streptococcus sanguis*. *J. Gen. Microbiol*. 135:3183-3197.

Kalbitzer et al., 1982. HPr proteins of different microorganisms studied by hydrogen-1 high resolution nuclear magnetic resonance: similarities of structures and mechanisms. *Biochemistry* 21:2879-2885.

Keating et al., Aromatic inhibitors derived from ammonia-pretreated lignocellulose hinder bacterial ethanologenesis by activating regulatory circuits controlling inhibitor efflux and detoxification, *Front Microbiol*, 2014. 5: p. 402.

Kim et al., OptORF: Optimal metabolic and regulatory perturbations for metabolic engineering of microbial strains. *BMC Syst Biol*, 2010. 4: p. 53.

Kim et al., RELATCH: relative optimality in metabolic networks explains robust metabolic and regulatory responses to perturbations. *Genome Biol*, 2012. 13(9): p. R78.

Kohlbrecher et al., 1992. Staphylococcal phosphoenolpyruvate-dependent phospho-transferase system: molecular cloning and nucleotide sequence of the *Staphylococcus carnosus* ptsI gene and expression and complementation studies of the gene product. *J. Bacteriol*. 174:2208-2214.

Lengeler et al., 1992, The Enzymes II of the PTS as carbohydrate transport systems: what the evolutionary studies tell us on their structure and function, p. 77-85. In E. Quagliariello and F. Palmieri (ed.), Molecular mechanisms of transport. Elsevier Biomedical Press, Amsterdam.

Licalsi et al., 1991. Sugar transport by the bacterial phosphotransferase system. Structural and thermodynamic domains of Enzyme I of *Salmonella typhimurium*. *J. Biol. Chem*. 266:19519-19527.

Lopez-De Los Santos et al., Genetic engineering of the phosphocarrier protein NPr of the *Escherichia coli* phosphotransferase system selectively improves sugar uptake activity. *J Biol Chem*. Aug. 24, 2012; 287(35):29931-9.

Marquet et al., 1976. The phosphoenolpyruvate: methyl-a-n-glucoside phosphotransferase system in *Bacillus subtilis* Marburg 168: purification and identification of the phosphocarrier protein (HPr). *Biochimie* 58:435-441.

Mimura et al., 1984. Resolution of the phosphotransferase enzymes of *Streptococcus mutans*: purification and preliminary characterization of a heat-stable phosphocarrier protein. *Infect. Immun*. 44:708-715.

Nelson, S. 0 et al., 1984. Molecular cloning, sequencing, and expression of the err gene: the structural gene for $III^{Glc}$ of the bacterial PEP:glucose phosphotransferase system. *EMBO J*. 3:1587-1593.

Orth et al., A comprehensive genome-scale reconstruction of *Escherichia coli* metabolism—2011. *Mol Syst Biol*, 2011. 7: p. 535.

Peri et al., 1990. Cloning and characterization of the N-acetylglucosamine cosa operon of *Escherichia coli*. *Biochem. Cell Biol*. 68:123-137.

Peri et al., 1988. Sequence of cloned Enzyme $II^{N-acetylglucomamine}$ of the phosphoenolpyruvate:Nacetylglucosamine phosphotransferase system of *Escherichia coli*, *Biochemistry* 27:6054-6061.

Postma PW et al., Phosphoenolpyruvate:carbohydrate phosphotransferase systems of bacteria. *Microbiol Rev*. Sep. 1993;57(3):543-94.

Powers, D. A et al., 1984. The primary structure of the *Salmonella typhimurium* HPr, a phosphocarrier protein of the phosphoenolpyruvate:glycose phosphotransferase system. A correction. *J. Biol. Chem*. 259:15212-15214.

Reed, J.L. et al., An expanded genome-scale model of *Escherichia coli* K-12 (iJR904 GSM/GPR). *Genome Biol*, 2003. 4(9): p. R54.

Reidl, J. et al., 1991. The malX malY operon of *Escherichia coli* encodes a novel enzyme II of the phosphotransferase system recognizing glucose and maltose and an enzyme abolishing the endogenous induction of the maltose system. *J. Bacteriol*. 173:4862-4876.

Reizer, J et al., 1989. Metabolitesensitive, ATP-dependent, protein kinase-catalyzed phosphorylation of HPr, a phosphocarrier protein of the phosphotransferase system in Gram-positive bacteria. *Biochimie* 71:989-996.

Reizer, J. et al., 1992, Functional interactions between proteins of the phosphoenolpyruvate:sugar phosphotransferase systems of *Bacillus subtilis* and *Escherichia coli*. *J. Biol. Chem*. 267:9158-9169.

Reizer, J. et al., 1988. The phosphoenolpyruvate:sugar phosphotransferase system in Gram-positive bacteria: properties, mechanism and regulation. *Crit. Rev. Microbiol*. 15:297-338.

Reizer, J. et al., 1989. Mechanistic and physiological consequences of HPr (ser) phosphorylation on the activities of the phosphoenolpyruvate: sugar phosphotransferase system in Gram-positive bacteria: studies with site-specific mutants of HPr, *EMBO J*. 8:2111-2120.

Robillard, G. T. et al., 1979. *Escherichia coli* phosphoenolpyruvale dependent phosphotransferase system. Complete purification of Enzyme I by hydrophobic interaction chromatography. *Biochemistry* 18:2984-2989.

Rogers, M. J. et al., 1988. Nucleotide sequences of the *Escherichia coli* nagE and nagB genes: the structural genes for the N-acetylglucosamine transport protein of the bacterial phosphoenolpyruvate: sugar phosphotransferase system and for glucosamine-6-phosphate deaminase. *Gene* 62 197-207.

Saffen, D et al., 1987. Sugar transport. By the bacterial phosphotransferase system. Molecular cloning and structural analysis of the *Escherichia coli* ptsH, ptsI, and crr genes. *J. Biol. Chem*. 262:16241-16253.

Saier, M.H. et al., The catabolite repressor/activator (Cra) protein of enteric bacteria. *J Bacteriol*, 1996. 178(12): p. 3411-7.

Sato, Y. et al., 1989. Characterization and sequence analysis of the scrA gene encoding enzyme $II^{Scr}$ of the *Streptococcus mutans* phosphoenolpyruvate-dependent sucrose phosphotransferase system. *J. Bacteriol*. 171:263-271.

Schnetz, K., C et al., 1987. β-Glucoside (bgl)operon of *Escherichia coli* K-12: nucleotide sequence, genetic organization, and possible evolutionary relationship to regulatory components of two *Bacillus subtilis* genes. *J. Bacteriol*. 169:2579-2590.

(56) References Cited

OTHER PUBLICATIONS

Schnierow, B. J et al., 1989. Partial nucleotide sequence of the pts operon in *Salmonella typhimurium*: comparative analyses in five bacterial genera. *Mol. Microbiol.* 3:113-118.

Schwalbach, M.S. et al., Complex physiology and compound stress responses during fermentation of alkali-pretreated corn stover hydrolysate by an *Escherichia coli* ethanologen. *Appl Environ Microbiol*, 2012. 78(9): p. 3442-57.

Simoni, R. D. et al., 1973. Sugar transport. IV. Isolation and characterization of the lactose phosphotransferase system in *Staphylococcus aureus*. *J. Biol. Chem.* 248:932-940.

Sutrina. S. L. et al., 1988, Inducer expulsion in *Streptococcus pyogenes*: properties and mechanism of the efflux reaction. *J. Bacteriol.* 170:1874-1877.

Tchieu et al., The complete phosphotransferase system in *Escherichia coli*. *J Mol Microbiol Biotechnol*. Jul. 2001;3(3):329-46.

Thibault, L. et al., 1985. Phosphoenolpyruvate-sugar phosphotransferase transport system of *Streptococcus mutans*: purification of HPr and enzyme I and determination of their intracellular concentrations by rocket inlmunoelectrophoresis. *Inject. lmmun.* 50:817-825.

Titgemeyer, F. et al., 1990. The nucleotide sequence of ptsH gene from *Klebsiella pneumoniae*. *Nucleic Acids Res.* 18:1898.

Vadeboncoeur, C. et al., 1983. Purification of proteins similar to HPr and enzyme I from the oral bacterium *Streptococcus salivarius*. Biochemical and immunochemical properties. *Can. J. Microbiol.* 29:1694-1705.

Vogler, A. P. et al., 1991. Comparison of the sequences of the nagE operons from *Klebsiella pneumonia* and *Escherichia coli* K12: enhanced variability of the enzyme $II^{N-acetylglucosamine}$ in regions connecting fuctional domains. *Mol. Gen. Genet.* 230:270-276.

Waygood, E. B. et al., 1980. Enzyme I of the phosphoenolpyruvate:sugar phosphotransferase system of *Escherichia coli*. Purification to homogeneity and some properties. *Can. J. Biochem.* 58:40-48.

Waygood, E. B. et al., 1980. Resolution of the phosphoenolpyruvate: fructose phosphotransferase system of *Escherichia coli* into two components: enzyme utructose and fructose-induced HPrlike protein (FPr). *Can. J. Biochem.* 58:1144-1146.

Waygood, E. B. et al., 1986. Phosphoproteins and the phosphoenolpyruvate:sugar phosphotransferase system of *Streptococcus salivarius*. Detection of two different ATP-dependent phosphorylations of the phosphocarrier protein HPr. *Can. J. Microbiol.* 32:310-318.

Weigel, N. et al., 1982. Sugar transport by the bacterial phosphotransferase system. Primary structure and active site of a general phosphocarrier protein (HPr) from *Salmonella typhimurium*. *J. Biol. Chem.* 257:14499-14509.

Weigel, N. et al., 1982. Sugar transport by the bacterial phosphotransferase system. Isolation and characterization of Enzyme I from *Salmonella typhimurium*. *J. Biol. Chem.* 257: 14461-14469.

Zagorec, M. et al., 1992. Cloning and nucleotide sequence of the ptsG gene of *Bacillus subtilis*. *Mol. Gen. Genet.* 234:325-328.

Zukowski, M. M. et al., 1990. Nucleotide sequence of the sacS locus of *Bacillus subtilis* reveals the presence of two regulatory genes. *Gene* 90:153-155.

\* cited by examiner

MICROORGANISMS THAT CO-CONSUME GLUCOSE WITH NON-GLUCOSE CARBOHYDRATES AND METHODS OF USE

STATEMENT REGARDING FEDERALLY SPONSORED RESEARCH

This invention was made with government support under DE-FC02-07ER64494 awarded by the US Department of Energy. The government has certain rights in the invention.

FIELD OF THE INVENTION

The invention is generally directed to microorganisms that co-consume glucose with non-glucose carbohydrates as well as methods of using the microorganisms for the production of commodity chemicals. The invention in a specific aspect is directed to microorganisms that co-consume glucose and xylose, e.g., in lignocellulosic hydrolysates, for converting the glucose and xylose into ethanol.

BACKGROUND

Ethanol obtained from the fermentation of starch from grains or sucrose from sugar cane is blended with gasoline to supplement petroleum supplies. The relatively oxygenated ethanol increases the efficiency of combustion and the octane value of the fuel mixture. Production of ethanol from grain and other foodstuffs, however, can limit the amount of agricultural land available for food and feed production, thereby raising the market prices of grains and leading to the expansion of agricultural production into forests or marginal lands thereby resulting in ecological damage. Moreover, the intense tillage and fertilization of prime agricultural land for the production of grains can result in excessive soil erosion and runoff or penetration of excess phosphorous and nitrogen into waterways and aquifers. Production of ethanol from lignocellulosic agricultural or woody feedstocks that do not compete with food and animal feed supplies is therefore highly desirous for the large-scale development of renewable fuels from biomass.

Several obstacles currently limit the use of biomass for renewable fuel production. The biomass must be pretreated to extract the sugars, lignins, and other components from the starting material. Mild conditions for pre-hydrolysis are desirable because they result in the formation of lower amounts of inhibitory components such as furfural, hydroxymethyl furfural, and sugar degradation products such as formic acid. The resulting sugars can be present in the form of monosaccharides such as D-glucose, D-xylose, D-mannose, D-galactose and L-arabinose or as various oligomers or polymers of these constituents along with other lignocellulosic components such as acetic acid, 4-O-methylglucuronic acid, and ferulic acid. Glucose in sugar hydrolysates may repress the induction of transcripts for proteins essential for the assimilation of less readily utilized sugars that are also present in hydrolysates, such as xylose, cellobiose, galactose, arabinose, and rhamnose. In addition, the production of ethanol from glucose can attain inhibitory concentrations even before use of other sugars commences. This results in the incomplete utilization of sugars and sugar mixtures in hydrolysates. Glucose in sugar hydrolysates may also repress the induction of transcripts for proteins essential for the depolymerization of cellulose, cellulo-oligosaccharides, xylan, xylo-oligosaccharides, mannan, manno-oligosaccharides, and other more complex hemicelluloses and oligosaccharides derived from them. These poly- and oligo-saccharides can be present in hydrolysates that have been recovered under mild treatment conditions.

Bacteria such as *Escherichia coli, Zymomonas mobilis*, and *Klebsiella oxytoca* and yeasts such as *Saccharomyces cerevisiae* and *Scheffersomyces stipitis* have been engineered for the production of ethanol from xylose, arabinose, xylo- and cellulo-oligosaccharides since native strains of these organisms are limited either by low production rates, strong preference for utilization of glucose over xylose, susceptibility to inhibitors, susceptibility to microbial or bacteriophage contamination, high requirements for nutrients, or containment regulations due to the expression of transgenes in order to achieve xylose or cellobiose utilization. There remains a need for microorganisms that will ferment glucose, xylose, and other sugars from lignocellulosic materials at high rates and yields without these drawbacks.

SUMMARY OF THE INVENTION

The invention provides microorganisms and uses thereof that address at least some of the above-mentioned needs.

The microorganisms of the invention include recombinant microorganisms. One version is a microorganism comprising modifications that reduce or ablate the activity of a phosphoenolpyruvate (PEP):carbohydrate phosphotransferase system (PTS) protein selected from the group consisting of an enzyme I (EI), an HPr, an FPr, and an enzyme $II^{Glc}$ ($EII^{Glc}$). In some versions, the microorganism comprises a modification that reduces or ablates the activity of one or both of HPr and FPr. The HPr may comprise the HPr of *E. coli* or an ortholog thereof, and the FPr may comprise the FPr of *E. coli* or an ortholog thereof. In some versions, the microorganism comprises a modification that reduces or ablates the activity of one or both of an EI and an $EII^{Glc}$.

Another version is a microorganism comprising a first modification that reduces or ablates the activity of a phosphoglucose isomerase and a second modification selected from the group consisting of a modification that reduces or ablates the activity of GntR, a modification that introduces a recombinant phosphogluconate dehydratase gene, a modification that introduces a recombinant 2-keto-4-hydroxyglutarate aldolase gene, a modification that introduces a recombinant 2-keto-3-deoxy-6-phosphogluconate aldolase gene, and a modification that introduces a recombinant oxaloacetate decarboxylase gene. In some versions, the second modification comprises a modification that reduces or ablates the activity of GntR. In some versions, the second modification comprises a modification that introduces a recombinant phosphogluconate dehydratase gene. In some versions, the second modification comprises one or more modifications that introduce one or more of a recombinant 2-keto-4-hydroxyglutarate aldolase gene, a recombinant 2-keto-3-deoxy-6-phosphogluconate aldolase gene, and a recombinant oxaloacetate decarboxylase gene. In some versions, the second modification comprises one or more modifications that introduce a recombinant phosphogluconate dehydratase gene and one or more of a recombinant 2-keto-4-hydroxyglutarate aldolase gene, a recombinant 2-keto-3-deoxy-6-phosphogluconate aldolase gene, and a recombinant oxaloacetate decarboxylase gene. In some versions, the second modification comprises one or more modifications that introduce a recombinant phosphogluconate dehydratase gene, a recombinant 2-keto-4-hydroxyglutarate aldolase gene, a recombinant 2-keto-3-deoxy-6-phosphogluconate aldolase gene, and a recombinant oxaloacetate decarboxylase gene.

The microorganisms in any of the above-mentioned versions may further comprise at least one, some, or all of a modification that reduces or ablates the activity of a pyruvate formate lyase, a modification that reduces or ablates the activity of a lactate dehydrogenase, a modification that reduces or ablates the activity of a fumarate reductase, a modification that introduces a recombinant pyruvate decarboxylase gene, and a modification that introduces a recombinant alcohol dehydrogenase gene.

A method of the invention comprises consuming a carbohydrate by culturing a microorganism as described herein in a medium. The medium preferably comprises glucose and xylose, and the culturing preferably co-consumes the xylose with the glucose. The medium may comprise a biomass hydrolysate, such as an enzymatic or acid hydrolysate. In some versions, the microorganism is adapted to growth in a first medium comprising a component selected from the group consisting of glucose, xylose, and ethanol prior to culturing the microorganism in the medium. In some versions, the culturing produces an amount of ethanol during the consumption of the carbohydrate.

The objects and advantages of the invention will appear more fully from the following detailed description of the preferred embodiment of the invention made in conjunction with the accompanying drawings.

DETAILED DESCRIPTION OF THE INVENTION

Figure 1:
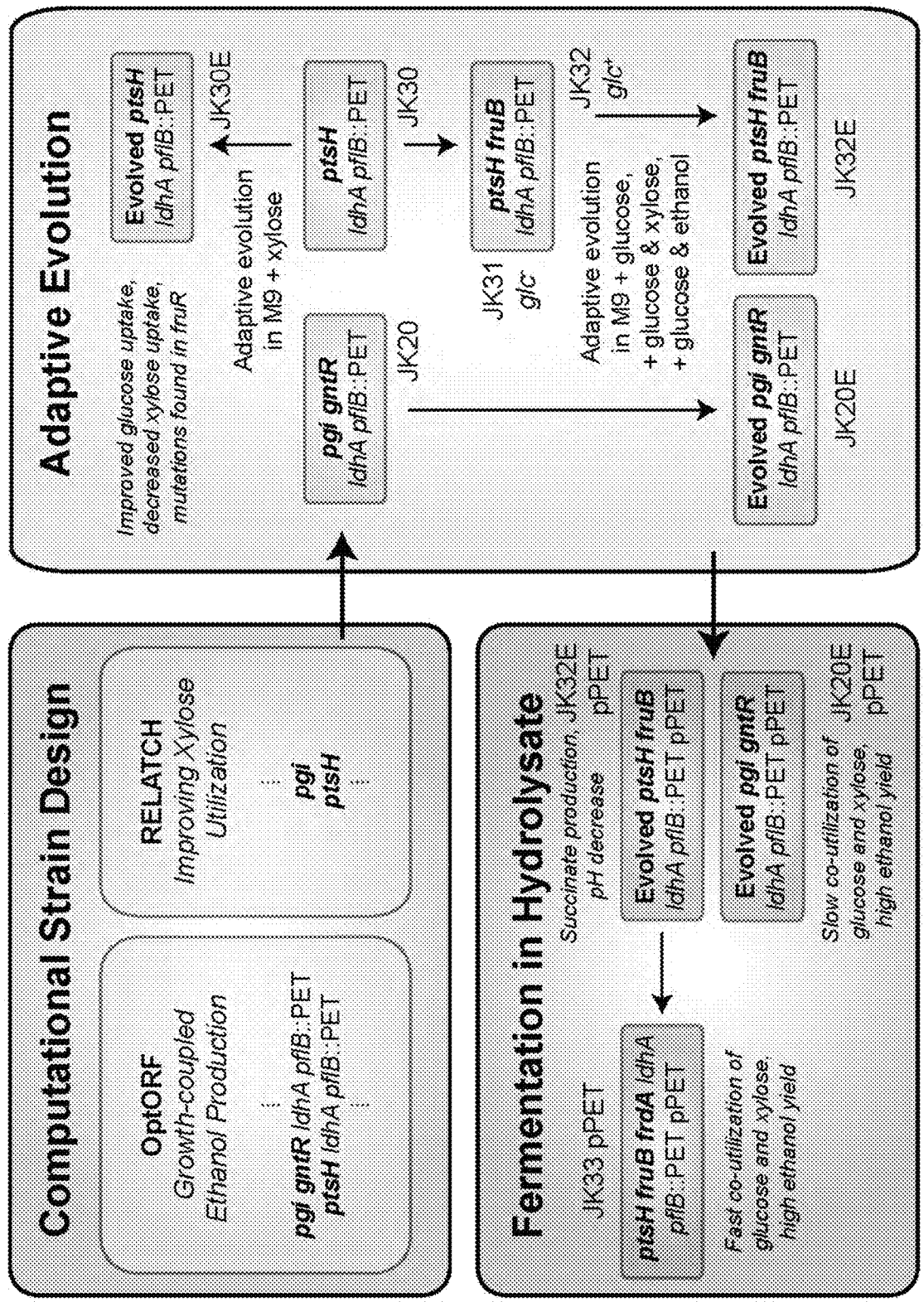
FIG. 1 shows a schema of the development and fermentation characteristics of exemplary microorganisms of the invention.

One aspect of the invention is a recombinant (i.e., genetically modified) microorganism. The microorganism may be a eukaryotic microorganism or a prokaryotic microorganism. Exemplary eukaryotic microorganisms include protists and yeasts. Exemplary prokaryotes include bacteria and archaea. Examples of suitable bacterial cells include gram-positive bacteria such as strains of *Bacillus*, (e.g., *B. brevis* or *B. subtilis*), *Pseudomonas*, and *Streptomyces*, and gram-negative bacteria, such as strains of *Escherichia coli* and *Aeromonas hydrophila*. Examples of suitable yeast cells include strains of *Saccharomyces* (e.g., *S. cerevisiae*), *Schizosaccharomyces*, *Kluyveromyces*, *Pichia* (e.g., *P. pastoris* or *P. methlanolica*), *Hansenula* (e.g., *H. Polymorpha*), *Yarrowia*, *Scheffersomyces*, (e.g., *S. stipitis*), and *Candida*.

In some versions of the invention, the microorganism is a microorganism that comprises a phosphoenolpyruvate (PEP):carbohydrate phosphotransferase system (PTS). The PTS is a well characterized carbohydrate transport system utilized by microorganisms such as bacteria. See Postma et al. 1993 and Tchieu et al. 2001, which are incorporated herein by reference in their entirely. Exemplary bacteria comprising the PTS include those from the genera *Bacillus*, *Clostridium*, *Enterobacteriaceae*, *Enterococcus*, *Erwinia*, *Escherichia*, *Klebsiella*, *Lactobacillus*, *Lactococcus*, *Mycoplasma*, *Pasteurella*, *Rhodobacter*, *Rhodoseudomonas*, *Salmonella*, *Staphylococcus*, *Streptococcus*, *Vibrio*, and *Xanthomonas*. Exemplary species include *E. coli*, *Salmonella typhimurium*, *Staphylococcus camosus*, *Bacillus subtilis*, *Mycoplasma capricolum*, *Enterococcus faecalis*, *Staphylococcus aureus*, *Streptococcus salivarius*, *Streptococcus mutans*, *Klebsiella pneumoniae*, *Staphylococcus camosus*, *Streptococcus sanguis*, *Rhodobacter capsulatus*, *Vibrio alginolyticus*, *Erwinia chrysanthemi*, *Xanthomonas campestris*, *Lactococcus lactis*, *Lactobacillus casei*, *Rhodoseudomonas sphaeroides*, *Erwinia carotovora*, *Pasteurella multocida*, and *Clostridium acetobutylicum*.

In some versions of the invention, the microorganism comprises intact fadA, fadB, fadI, fadJ, and/or fadR genes or expresses the functional gene products thereof.

The microorganisms of the invention comprise modifications that reduce or ablate the activity of gene products of one or more genes. Such a modification that that reduces or ablates the activity of gene products of one or more genes is referred to herein as a "functional deletion" of the gene product. "Functional deletion" or its grammatical equivalents refers to any modification to a microorganism that ablates, reduces, inhibits, or otherwise disrupts production of a gene product, renders a produced gene product non-functional, or otherwise reduces or ablates a produced gene product's activity. Accordingly, in some instances, a gene product that is functionally deleted means that the gene product is not produced by the microorganism at all. "Gene product" refers to a protein or polypeptide encoded and produced by a particular gene. "Gene" refers to a nucleic acid sequence capable of producing a gene product and may include such genetic elements as a coding sequence together with any other genetic elements required for transcription and/or translation of the coding sequence. Such genetic elements may include a promoter, an enhancer, and/or a ribosome binding site (RBS), among others.

One of ordinary skill in the art will appreciate that there are many well-known ways to functionally delete a gene product. For example, functional deletion can be accomplished by introducing one or more genetic modifications. As used herein, "genetic modifications" refer to any differences in the nucleic acid composition of a cell, whether in the cell's native chromosome or in endogenous or exogenous non-chromosomal plasmids harbored within the cell. Examples of genetic modifications that may result in a functionally deleted gene product include but are not limited to substitutions, partial or complete deletions, insertions, or other variations to a coding sequence or a sequence controlling the transcription or translation of a coding sequence, such as placing a coding sequence under the control of a less active promoter, etc. In some versions, a gene or coding sequence can be replaced with a selection marker or screenable marker. Various methods for introducing genetic modifications are well known in the art and include homologous recombination, among other mechanisms. See, e.g., Green et al., *Molecular Cloning: A laboratory manual*, 4$^{th}$ ed., Cold Spring Harbor Laboratory Press (2012) and Sambrook et al.,

*Molecular Cloning: A Laboratory Manual*, 3rd ed., Cold Spring Harbor Laboratory Press (2001). Various other genetic modifications that functionally delete a gene product are described in the examples below. In some versions, functional deletion can be accomplished by expressing ribozymes or antisense sequences that target the mRNA of the gene of interest. Functional deletion can also be accomplished by inhibiting the activity of the gene product, for example, by chemically inhibiting a gene product with a small-molecule inhibitor, by expressing a protein that interferes with the activity of the gene product, or by other means.

In certain versions of the invention, the functionally deleted gene product may have less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the activity of the non-functionally deleted gene product.

In certain versions of the invention, a cell with a functionally deleted gene product may have less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the activity of the gene product compared to a cell with the non-functionally deleted gene product.

In certain versions of the invention, the functionally deleted gene product may be expressed at an amount less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the amount of the non-functionally deleted gene product.

In certain versions of the invention, the functionally deleted gene product may result from a genetic modification in which at least 1, at least 2, at least 3, at least 4, at least 5, at least 10, at least 20, at least 30, at least 40, at least 50, or more nonsynonymous substitutions are present in the gene or coding sequence of the gene product.

In certain versions of the invention, the functionally deleted gene product may result from a genetic modification in which at least 1, at least 2, at least 3, at least 4, at least 5, at least 10, at least 20, at least 30, at least 40, at least 50, or more bases are inserted in the gene or coding sequence of the gene product.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of the gene product's gene or coding sequence is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of a promoter driving expression of the gene product is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of an enhancer controlling transcription of the gene product's gene is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of a sequence controlling translation of the gene product's mRNA is deleted or mutated.

In certain versions of the invention, the decreased activity or expression of the functionally deleted gene product is determined with respect to the activity or expression of the gene product in its unaltered state as found in nature. In certain versions of the invention, the decreased activity or expression of the functionally deleted gene product is determined with respect to the activity or expression of the gene product in its form in a corresponding microorganism. In certain versions, the genetic modifications giving rise to a functionally deleted gene product are determined with respect to the gene in its unaltered state as found in nature. In certain versions, the genetic modifications giving rise to a functionally deleted gene product are determined with respect to the gene in its form in a corresponding microorganism. As used herein, "corresponding microorganism" refers to a microorganism of the same species having the same or substantially same genetic and proteomic composition as a microorganism of the invention, with the exception of genetic and proteomic differences resulting from the manipulations described herein for the microorganisms of the invention.

In some versions of the invention, a gene product of the PTS is functionally deleted. The PTS may comprise such proteins as enzyme I (EI), HPr, FPr, multiphosphoryl transfer protein (MTP), enzyme II (EII) and enzyme III (EIII). The following reactions comprise exemplary PTS-mediated translocation and phosphorylation reactions with a given carbohydrate (P=phospho group):

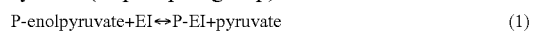  (1)

  (2)

  (3)

  (4)

  (5)

In most cases, EI and HPr are soluble, cytoplasmic proteins that participate in the phosphorylation of all PTS carbohydrates in a given organism and thus have been called the general PTS proteins. The EIIs are carbohydrate specific and may consist of a single membrane-bound protein composed of three domains (A, B, and C), such as that for mannitol (EII$^{Mtl}$) in *E. coli*, or of two or more proteins, at least one of which is membrane bound (e.g., B and C) and one of which is soluble (IIA or EIII), such as the IICB$^{glc}$-IIA$^{Glc}$ pair for glucose in *E. coli*. In both cases, the phospho group is transferred from PEP to the incoming carbohydrate via obligatory phospho intermediates of EI, HPr, EIIA, and EIIB. The EIIC domain, which makes up the integral membrane portion of an EII, presumably forms its translocation channel and at least part of its specific substrate-binding site. In a third variation, exemplified by the mannose PTS in *E. coli*, both A and B domains are fused in a single soluble polypeptide, while there are two integral membrane proteins (IIC$^{Man}$ and IID$^{Man}$) involved in mannose translocation.

Although the glucose, mannitol, and mannose PTSs of *E. coli* are the most common in terms of protein organization in most organisms, other variations are possible. For example, the cellobiose PTS in *E. coli* has been shown to have each functional domain of its EII as a separate protein: two soluble proteins (IIA$^{Cel}$ and IIB$^{Cel}$) that each contain a site of covalent phosphorylation, and one membrane-bound protein (IIC$^{Cel}$). For PTS-mediated fructose transport, a protein called FPr (fructose-specific HPr) combines the functions of the IIA$^{Fru}$ domain and of an HPr-like protein (Geerse et al. 1989). In this case, then, it is FPr rather than HPr that is phosphorylated by EI (on the HPr-like domain) as an intermediate in fructose translocation.

In some versions of the invention, an EI in the recombinant microorganism is functionally deleted. EIs include enzymes classified under Enzyme Commission (EC) number 2.7.3.9. An exemplary EI is the PtsI of *E. coli*, which is encoded by ptsI. An exemplary sequence of the *E. coli* PtsI is SEQ ID NO:2, and an exemplary sequence of the *E. coli* ptsI is SEQ ID NO:1. Other EIs include homologs of the *E. coli* PtsI. Homologs of the *E. coli* PtsI include orthologs of the *E. coli* PtsI, paralogs of such orthologs having PtsI activity, and paralogs of the *E. coli* PtsI in *E. coli* having PtsI activity. The *E. coli* PtsI and homologs thereof are well-recognized in the art. See Postma et al. 1993, Tchieu et al. 2001, Robillard et al. 1979, Waygood et al. 1980, Byrne et al 1988, De Reuse et al. 1988, Saffen et al. 1987, Weigel et al. 1982, LiCalsi et al. 1991, Schnierow et al. 1989, Kohlbrecher et al. 1992, Reizer et al. 1992, Gonzy-Tréboul et al. 1989, Jaffor et al. 1977, Alpert et al. 1985, Hengstenberg et al. 1976, Albert et al. 1985, Vadeboncoeur et al. 1983, Gagnon et al. 1992, and Thibault et al. 1985.

In some versions of the invention, an HPr in the recombinant microorganism is functionally deleted. HPrs include enzymes classified under EC 2.7.11.-. HPrs also include proteins classified as TC 8.A.8.1.1 in the Transporter Classification System. An exemplary HPr is the HPr of *E. coli*, which is encoded by ptsH. An exemplary sequence of the *E. coli* HPr is SEQ ID NO:4, and an exemplary sequence of the *E. coli* ptsH is SEQ ID NO:3. Other HPrs include homologs of the *E. coli* HPr. Homologs of the *E. coli* HPr include orthologs of the *E. coli* HPr, paralogs of such orthologs having the HPr activity, and paralogs of the *E. coli* HPr in *E. coli* having HPr activity. The *E. coli* HPr and homologs thereof are well-recognized in the art. See Postma et al. 1993, Tchieu et al. 2001 Anderson et al. 1971, Dooijewaard et al. 1979, Byrne et al. 1988, De Reuse et al. 1988, Saffen et al. 1987, Weigel et al. 1982, Beneski et al. 1982, Byrne et al. 1988, Powers et al. 1984, Schnierow et al. 1989, Titgemeyer et al. 1990, Kalbitzer et al. 1982, Marquet et al. 1976, Reizer et al. 1989, Reizer et al. 1989, Gonzy-Tréboul et al. 1989, Jaffor et al. 1976, Beyreuther et al. 1977, Simoni et al. 1973, Reizer et al. 1988, Eisermann et al. 1991, Deutscher et al. 1986, Vadeboncoeur et al. 1983, Waygood et al. 1986, Mimurs et al. 1984, Thibault et al. 1985, and Jenkinson 1989.

In some versions of the invention, an FPr in the recombinant microorganism is functionally deleted. FPrs include enzymes classified under EC 2.7.1.69. An exemplary FPr is the FPr of *E. coli*, which is encoded by fruB. An exemplary sequence of the *E. coli* FPr is SEQ ID NO:6, and an exemplary sequence of the *E. coli* fruB is SEQ ID NO:5. Other FPrs include homologs of the *E. coli* FPr. Homologs of the *E. coli* FPr include orthologs of the *E. coli* FPr, paralogs of such orthologs having FPr activity, and paralogs of the *E. coli* FPr in *E. coli* having FPr activity. The *E. coli* FPr and homologs thereof are well-recognized in the art. See Postma et al. 1993, Tchieu et al. 2001, Waygood 1980, Geerse et al. 1986, Sutrina et al. 1988, and Geerse et al. 1989.

In some versions of the invention, a glucose-specific EII (EII$^{Glc}$) is functionally deleted. EII$^{Glc}$ proteins include any protein comprising one or more of an EIIA domain, an EIIB domain, and an EIIC domain having activity for glucose. EIIA$^{Glc}$ domains include those having activity classified under EC:2.7.1.-. EIIB$^{Glc}$ domains include those having activity classified under EC:2.7.1.69. An exemplary EII$^{Glc}$ is the EIIA$^{Glc}$ of *E. coli*, which is encoded by crr. An exemplary sequence of the *E. coli* EIIA$^{Glc}$ is SEQ ID NO:8, and an exemplary sequence of the *E. coli* crr is SEQ ID NO:7. Another exemplary EII$^{Glc}$ is the PTS system glucose-specific EIICB component (PTGCB) of *E. coli*, which is encoded by ptsG. An exemplary sequence of the *E. coli* PTGCB is SEQ ID NO:10, and an exemplary sequence of the *E. coli* ptsG is SEQ ID NO:9. EII$^{Glc}$ proteins are well-recognized in the art. See Postma et al. 1993, Tchieu et al. 2001, Erni et al. 1986, Saffen et al. 1987, Nelson et al. 1984, Gonzy-Tréboul et al. 1991, Gonzy-Tréboul et al. 1989, Zagorec et al. 1992, Reidl et al. 1991, Boos et al. 1990, Peri et al. 1990, Peri et al. 1988, Rogers et al. 1988, Vogler et al. 1991, Ebner et al. 1988, Lengeler et al. 1992, Blatch et al. 1990, Fouet et al. 1987, Zukowski et al. 1990, Sato et al. 1989, Bramley et al. 1987, Schnetz et al. 1987, El Hassouni et al. 1992, and Hall et al. 1992.

In some versions of the invention, a non-PTS protein is functionally deleted. Microorganisms in which non-PTS proteins are functionally deleted may or may not comprise a PTS and may comprise any type of microorganism described herein.

Accordingly, in some versions of the invention a phosphoglucose isomerase in the recombinant microorganism is functionally deleted. Phosphoglucose isomerases are also known as glucose-6-phosphate isomerases and phosphohexose isomerases. Phosphoglucose isomerases include enzymes classified under EC 5.3.1.9. An exemplary phosphoglucose isomerase is the glucose-6-phosphate isomerase of *E. coli*, which is encoded by pgi. An exemplary sequence of the *E. coli* glucose-6-phosphate isomerase is SEQ ID NO:12, and an exemplary sequence of the *E. coli* pgi is SEQ ID NO:11. Other phosphoglucose isomerases include homologs of the *E. coli* glucose-6-phosphate isomerase. Homologs of the *E. coli* glucose-6-phosphate isomerase include orthologs of the *E. coli* glucose-6-phosphate isomerase, paralogs of such orthologs having phosphoglucose isomerase activity, and paralogs of the *E. coli* glucose- 6-phosphate isomerase in *E. coli* having phosphoglucose isomerase activity. Phosphoglucose isomerases are well-recognized in the art.

In some versions of the invention a GntR in the recombinant microorganism is functionally deleted. GntRs are transcriptional regulators of enzymes involved in gluconate metabolism. An exemplary GntR is the GntR of *E. coli*, which is encoded by gntR. An exemplary sequence of the *E. coli* GntR is SEQ ID NO:14, and an exemplary sequence of the *E. coli* gntR is SEQ ID NO:13. Other GntRs include homologs of the *E. coli* GntR. Homologs of the *E. coli* GntR include orthologs of the *E. coli* GntR, paralogs of such orthologs having GntR activity, and paralogs of the *E. coli* GntR in *E. coli* having GntR activity. GntRs are well-recognized in the art. The deletion of GntR in *E. coli* is believed to lead to higher expression of the endogenous edd-eda operon, the latter of which encodes a phosphogluconate dehydratase and a multifunctional 2-keto-4-hydroxyglutarate aldolase/2-keto-3-deoxy-6-phosphogluconate aldolase. Thus, an additional or alternative modification to functionally deleting a GntR is expressing or overexpressing a phosphogluconate dehydratase, a 2-keto-4-hydroxyglutarate aldolase, a 2-keto-3-deoxy-6-phosphogluconate aldolase, and/or an oxaloacetate decarboxylase. Phosphogluconate dehydratases, 2-keto-4-hydroxyglutarate aldolases, 2-keto-3-deoxy-6-phosphogluconate aldolases, and oxaloacetate decarboxylases are discussed below.

In some versions of the invention, a lactate dehydrogenase in the recombinant microorganism is functionally deleted. Lactate dehydrogenases include enzymes classified under EC 1.1.1.27. An exemplary lactate dehydrogenase is the LdhA of *E. coli*, which is encoded by ldhA. An exemplary sequence of the *E. coli* LdhA is SEQ ID NO:16, and an exemplary sequence of the *E. coli* ldhA is SEQ ID NO:15. Other lactate dehydrogenases include homologs of the *E. coli* LdhA. Homologs of the *E. coli* LdhA include orthologs of the *E. coli* LdhA, paralogs of such orthologs having lactate dehydrogenase activity, and paralogs of the *E. coli* LdhA in *E. coli* having lactate dehydrogenase activity. The *E. coli* LdhA and homologs thereof are well-recognized in the art.

In some versions of the invention, a pyruvate formate lyase in the recombinant microorganism is functionally deleted. Pyruvate formate lyases include enzymes classified under EC 2.3.1.54. An exemplary pyruvate formate lyase is the PFL of *E. coli*, which is encoded by pflB. An exemplary sequence of the *E. coli* PFL is SEQ ID NO:18, and an exemplary sequence of the *E. coli* pflB is SEQ ID NO:17. Other pyruvate formate lyases include homologs of the *E. coli* PFL. Homologs of the *E. coli* PFL include orthologs of the *E. coli* PFL, paralogs of such orthologs having pyruvate formate lyase activity, and paralogs of the *E. coli* PFL in *E. coli* having pyruvate formate lyase activity. The *E. coli* PFL and homologs thereof are well-recognized in the art.

In some versions of the invention, a pyruvate formate lyase activating enzyme in the recombinant microorganism is functionally deleted. Pyruvate formate lyase activating enzymes include enzymes classified under EC 1.97.1.4. Pyruvate formate lyase activating enzymes activate pyruvate formate lyases. Functionally deleting a pyruvate formate lyase activating enzyme constitutes a way to functionally delete a pyruvate formate lyase. An exemplary pyruvate formate lyase activating enzyme is the PFL activase of *E. coli*, which is encoded by pflA. An exemplary sequence of the *E. coli* PFL activase is SEQ ID NO:20, and an exemplary sequence of the *E. coli* pflA is SEQ ID NO:19. Other pyruvate formate lyase activating enzymes include homologs of the *E. coli* PFL activase. Homologs of the *E. coli* PFL activase include orthologs of the *E. coli* PFL activase, paralogs of such orthologs having pyruvate formate lyase activating activity, and paralogs of the *E. coli* PFL activase in *E. coli* having pyruvate formate lyase activating activity. The *E. coli* PFL activase and homologs thereof are well-recognized in the art.

In some versions of the invention, fumarate reductase in the recombinant microorganism is functionally deleted. Fumarate reductases include enzymes classified under EC 1.3.5.4 and EC 1.3.1.6. Fumarate reductases are multisubunit enzymes, which typically comprise A, B, C, and D subunits. A fumarate reductase can be functionally deleted by, e.g., modifying the genes for any one or more of the subunits. An exemplary fumarate reductase is the QFR of *E. coli*, which is comprised of FrdA, FrdB, FrdC, and FrdD. FrdA is encoded by frdA. FrdB is encoded by frdB. FrdC is encoded by frdC. FrdD is encoded by frdD. An exemplary sequence of the *E. coli* FrdA is SEQ ID NO:22, and an exemplary sequence of the *E. coli* frdA is SEQ ID NO:21. An exemplary sequence of the *E. coli* FrdB is SEQ ID NO:24, and an exemplary sequence of the *E. coli* frdB is SEQ ID NO:23. An exemplary sequence of the *E. coli* FrdC is SEQ ID NO:26, and an exemplary sequence of the *E. coli* frdC is SEQ ID NO:25. An exemplary sequence of the *E. coli* FrdD is SEQ ID NO:28, and an exemplary sequence of the *E. coli* frdD is SEQ ID NO:27. Other fumarate reductases include homologs of the *E. coli* QFR. Homologs of the *E. coli* QFR include orthologs of the *E. coli* QFR, paralogs of such orthologs having fumarate reductase activity, and paralogs of the *E. coli* QFR in *E. coli* having fumarate reductase activity. The *E. coli* QFR and homologs thereof are well-recognized in the art.

The above-mentioned proteins may be functionally deleted in various combinations in a cell to enhance ethanol production in the cell and/or to enhance dual sugar (e.g., glucose and xylose) consumption. One exemplary combination comprises functional deletion of any one or more of an EI, an HPr, an FPr, and an EII$^{Glc}$. Another exemplary combination comprises a functional deletion of any one or more of an EI, an HPr, an FPr, and an EII$^{Glc}$ and a functional deletion of any one or more of a pyruvate formate lyase, a lactate dehydrogenase, and a fumarate reductase. Another exemplary combination comprises a functional deletion of any one or more of an EI, an HPr, an FPr, and an EII$^{Glc}$ and a functional deletion of each of a pyruvate formate lyase, a lactate dehydrogenase, and a fumarate reductase. Another exemplary combination comprises a functional deletion of any one or more of an EI and an EII$^{Glc}$ and a functional deletion of any one or more of a pyruvate formate lyase, a lactate dehydrogenase, and a fumarate reductase. Another exemplary combination comprises a functional deletion of any one or more of an EI and an EII$^{Glc}$ and a functional deletion of each of a pyruvate formate lyase, a lactate dehydrogenase, and a fumarate reductase. Another exemplary combination comprises a functional deletion of an HPr and a functional deletion of any one or more of a pyruvate formate lyase, a lactate dehydrogenase, and a fumarate reductase. Another exemplary combination comprises a functional deletion of an HPr and a functional deletion of each of a pyruvate formate lyase, a lactate dehydrogenase, and a fumarate reductase. Another exemplary combination comprises a functional deletion of an FPr with a functional deletion of any one or more of a pyruvate formate lyase, a lactate dehydrogenase, and a fumarate reductase. Another exemplary combination comprises a functional deletion of an FPr and a functional deletion of each of a pyruvate formate lyase, a lactate dehydrogenase, and a fumarate reductase. Another exemplary combination comprises a functional deletion of an HPr and an FPr and a functional deletion of any one or more of a pyruvate formate lyase, a lactate dehydrogenase, and a fumarate reductase. Another exemplary combination comprises a functional deletion of an HPr and an FPr and a functional deletion of each of a pyruvate formate lyase, a lactate dehydrogenase, and a fumarate reductase. Another exemplary combination comprises a functional deletion of any one or more of a phosphoglucose isomerase and a GntR and a functional deletion of any one or more of a pyruvate formate lyase, a lactate dehydrogenase, and a fumarate reductase. Another exemplary combination comprises a functional deletion of any one or more of a phosphoglucose isomerase and a GntR and a functional deletion of each of a pyruvate formate lyase and a lactate dehydrogenase. Another exemplary combination comprises a functional deletion of each of a phosphoglucose isomerase and a GntR and a functional deletion of any one or more of a pyruvate formate lyase, a lactate dehydrogenase, and a fumarate reductase. Another exemplary combination comprises a functional deletion of each of a phosphoglucose isomerase and a GntR and a functional deletion of each of a pyruvate formate lyase and a lactate dehydrogenase.

In various versions of the invention, the cell is genetically modified to comprise a recombinant gene. In most cases, the recombinant gene is configured to be expressed or overexpressed in the cell. If a cell endogenously comprises a particular gene, the gene may be modified to exchange or optimize promoters, exchange or optimize enhancers, or exchange or optimize any other genetic element to result in increased expression of the gene. Alternatively, one or more additional copies of the gene or coding sequence thereof may be introduced to the cell for enhanced expression of the gene product. If a cell does not endogenously comprise a particular gene, the gene or coding sequence thereof may be introduced to the cell for expression of the gene product. The gene or coding sequence may be incorporated into the genome of the cell or may be contained on an extra-chromosomal plasmid. The gene or coding sequence may be introduced to the cell individually or may be included in an operon. Techniques for genetic manipulation are described in further detail below.

In some versions of the invention, the cells are genetically modified to express or overexpress a recombinant phosphogluconate dehydratase gene. "Phosphogluconate dehydratase gene" refers to a polynucleotide that encodes or expresses a phosphogluconate dehydratase or a gene product having phosphogluconate dehydratase activity. Phosphogluconate dehydratases are also known as 6-phosphogluconate dehydratases 6-phosphogluconic dehydrases, gluconate-6-phosphate dehydratases, gluconate 6-phosphate dehydratases, 6-phosphogluconate dehydrases, and 6-phospho-D-gluconate hydro-lyases. Phosphogluconate dehydratase activity includes the activity characterized by the enzymes classified under EC 4.2.1.12. An exemplary phosphogluconate dehydratase is the Edd of E. coli, which is encoded by edd. An exemplary sequence of the E. coli Edd is SEQ ID NO:30, and an exemplary sequence of the E. coli edd is SEQ ID NO:29. Other phosphogluconate dehydratases include homologs of the E. coli Edd. Homologs of the E. coli Edd include orthologs of the E. coli Edd, paralogs of such orthologs having phosphogluconate dehydratase activity, and paralogs of the E. coli Edd in E. coli having phosphogluconate dehydratase activity. Phosphogluconate dehydratases are well-recognized in the art.

In some versions of the invention, the cells are genetically modified to express or overexpress a recombinant 2-keto-4-hydroxyglutarate aldolase gene. "2-Keto-4-hydroxyglutarate aldolase gene" refers to a polynucleotide that encodes or expresses a 2-keto-4-hydroxyglutarate aldolase or a gene product having 2-keto-4-hydroxyglutarate aldolase activity. 2-Keto-4-hydroxyglutarate aldolases are also known as 4-hydroxy-2-oxoglutarate aldolases, 2-oxo-4-hydroxyglutarate aldolases, 4-hydroxy-2-oxoglutarate glyoxylate-lyases, KHG-aldolases, and KHGAs. 2-Keto-4-hydroxyglutarate aldolase activity includes the activity characterized by the enzymes classified under EC 4.1.3.16 and EC 4.1.3.42. An exemplary 2-keto-4-hydroxyglutarate aldolase is the Eda of E. coli, which is encoded by eda. An exemplary sequence of the E. coli Eda is SEQ ID NO:32, and an exemplary sequence of the E. coli eda is SEQ ID NO:31. Other 2-keto-4-hydroxyglutarate aldolases include homologs of the E. coli Eda. Homologs of the E. coli Eda include orthologs of the E. coli Eda, paralogs of such orthologs having 2-keto-4-hydroxyglutarate aldolase activity, and paralogs of the E. coli Eda in E. coli having 2-keto-4-hydroxyglutarate aldolase activity. 2-Keto-4-hydroxyglutarate aldolases are well-recognized in the art.

In some versions of the invention, the cells are genetically modified to express or overexpress a recombinant 2-keto-3-deoxy-6-phosphogluconate aldolase gene. "2-Keto-3-deoxy-6-phosphogluconate aldolase gene" refers to a polynucleotide that encodes or expresses a 2-keto-3-deoxy-6-phosphogluconate aldolase or a gene product having 2-keto-3-deoxy-6-phosphogluconate aldolase activity. 2-Keto-3-deoxy-6-phosphogluconate aldolases are also known as 2-dehydro-3-deoxy-phosphogluconate aldolases, 2-dehydro-3-deoxy-D-gluconate-6-phosphate D-glyceraldehyde-3-phosphate-lyases, KDPG-aldolases, phospho-2-dehydro-3-deoxygluconate aldolases, and phospho-2-keto-3-deoxygluconate aldolases. 2-Keto-3-deoxy-6-phosphogluconate aldolase activity includes the activity characterized by the enzymes classified under EC 4.1.2.14 and EC 4.1.2.55. An exemplary 2-keto-3-deoxy-6-phosphogluconate aldolase is the Eda of E. coli, which is encoded by eda. An exemplary sequence of the E. coli Eda is SEQ ID NO:32, and an exemplary sequence of the E. coli eda is SEQ ID NO:31. Other 2-keto-3-deoxy-6-phosphogluconate aldolases include homologs of the E. coli Eda. Homologs of the E. coli Eda include orthologs of the E. coli Eda, paralogs of such orthologs having 2-keto-3-deoxy-6-phosphogluconate aldolase activity, and paralogs of the E. coli Eda in E. coli having 2-keto-3-deoxy-6-phosphogluconate aldolase activity. 2-Keto-3-deoxy-6-phosphogluconate aldolases are well-recognized in the art.

In some versions of the invention, the cells are genetically modified to express or overexpress a recombinant oxaloacetate decarboxylase gene. "Oxaloacetate decarboxylase gene" refers to a polynucleotide that encodes or expresses an oxaloacetate decarboxylase or a gene product having oxaloacetate decarboxylase activity. Oxaloacetate decarboxylases are also known as oxaloacetate β-decarboxylases and oxaloacetate carboxy-lyases. Oxaloacetate decarboxylase activity includes the activity characterized by the enzymes classified under EC 4.1.1.3 and EC 1.1.1.38. An exemplary oxaloacetate decarboxylase is the Eda of E. coli, which is encoded by eda. An exemplary sequence of the E. coli Eda is SEQ ID NO:32, and an exemplary sequence of the E. coli eda is SEQ ID NO:31. Other oxaloacetate decarboxylases include homologs of the E. coli Eda. Homologs of the E. coli Eda include orthologs of the E. coli Eda, paralogs of such orthologs having oxaloacetate decarboxylase activity, and paralogs of the *E. coli* Eda in *E. coli* having oxaloacetate decarboxylase activity. Oxaloacetate decarboxylases are well-recognized in the art.

In some versions of the invention, the cells are genetically modified to express or overexpress a recombinant pyruvate decarboxylase gene. "Pyruvate decarboxylase gene" refers to a polynucleotide that encodes or expresses a pyruvate decarboxylase or a gene product having pyruvate decarboxylase activity. Pyruvate decarboxylase activity includes the activity characterized by the enzymes classified under EC 4.1.1.1. An exemplary pyruvate decarboxylase is the PDC of *Zymomonas mobilis*, which is encoded by pdc. An exemplary sequence of the *Z. mobilis* PDC is SEQ ID NO:34, and an exemplary sequence of the *Z. mobilis* pdc is SEQ ID NO:33. Other pyruvate decarboxylases include homologs of the *Z. mobilis* PDC. Homologs of the *Z. mobilis* PDC include orthologs of the *Z. mobilis* PDC, paralogs of such orthologs having pyruvate decarboxylase activity, and paralogs of the *Z. mobilis* PDC in *E. coli* having pyruvate decarboxylase activity. Pyruvate decarboxylases are well-recognized in the art.

In some versions of the invention, the cells are genetically modified to express or overexpress a recombinant alcohol dehydrogenase gene. "Alcohol dehydrogenase gene" refers to a polynucleotide that encodes or expresses an alcohol dehydrogenase or a gene product having alcohol dehydrogenase activity. Alcohol dehydrogenase activity includes the activity characterized by the enzymes classified under EC 1.1.1.1. An exemplary alcohol dehydrogenase is the ADH2 of *Zymomonas mobilis*, which is encoded by adhB. An exemplary sequence of the *Z. mobilis* ADH2 is SEQ ID NO:36, and an exemplary sequence of the *Z. mobilis* adhB is SEQ ID NO:35. Other alcohol dehydrogenases include homologs of the *Z. mobilis* ADH2. Homologs of the *Z. mobilis* ADH2 include orthologs of the *Z. mobilis* ADH2, paralogs of such orthologs having alcohol dehydrogenase activity, and paralogs of the *Z. mobilis* ADH2 in *Z. mobilis* having alcohol dehydrogenase activity. Alcohol dehydrogenases are well-recognized in the art.

The recombinant pyruvate decarboxylase gene and/or the recombinant alcohol dehydrogenase gene can be included in a microorganism comprising a functional deletion of any of the genes or gene products, or combinations thereof, described herein.

The cells of the invention may be genetically altered to functionally delete, express, or overexpress homologs of any of the specific genes or gene products explicitly described herein. Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Nucleic acid or gene product (amino acid) sequences of any known gene, including the genes or gene products described herein, can be determined by searching any sequence databases known the art using the gene name or accession number as a search term. Common sequence databases include GenBank (http://www.ncbi.nlm.nih.gov/genbank/), ExPASy (http://expasy.org/), KEGG (www.genome.jp/kegg/), among others. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity (e.g., identity) over 50, 100, 150 or more residues (nucleotides or amino acids) is routinely used to establish homology (e.g., over the full length of the two sequences to be compared). Higher levels of sequence similarity (e.g., identity), e.g., 30%, 35% 40%, 45% 50%, 55%, 60%, 65%, 70%, 75%, 80%, 85%, 90%, 95%, or 99% or more, can also be used to establish homology. Accordingly, homologs of the genes or gene products described herein include genes or gene products having at least about 30%, 35%, 40%, 45%, 50%, 55%, 60%, 65%, 70%, 75%, 80%, 85%, 90%, 95%, or 99% identity to the genes or gene products described herein. Methods for determining sequence similarity percentages (e.g., BLASTP and BLASTN using default parameters) are described herein and are generally available. The homologous proteins should demonstrate comparable activities and, if an enzyme, participate in the same or analogous pathways. Homologs include orthologs and paralogs. "Orthologs" are genes and products thereof in different species that evolved from a common ancestral gene by speciation. Normally, orthologs retain the same or similar function in the course of evolution. Paralogs are genes and products thereof related by duplication within a genome. As used herein, "orthologs" and "paralogs" are included in the term "homologs."

For sequence comparison and homology determination, one sequence typically acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence based on the designated program parameters. A typical reference sequence of the invention is a nucleic acid or amino acid sequence corresponding to the genes or gene products described herein.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see Current Protocols in Molecular Biology, F. M. Ausubel et al., eds., Current Protocols, a joint venture between Greene Publishing Associates, Inc. and John Wiley & Sons, Inc., (supplemented through 2008)).

One example of an algorithm that is suitable for determining percent sequence identity and sequence similarity for purposes of defining homologs is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues;

always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001. The above-described techniques are useful in identifying homologous sequences for use in the methods described herein.

The terms "identical" or "percent identity", in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described above (or other algorithms available to persons of skill) or by visual inspection.

The phrase "substantially identical" in the context of two nucleic acids or polypeptides refers to two or more sequences or subsequences that have at least about 60%, about 65%, about 70%, about 75%, about 80%, about 85%, about 90, about 95%, about 98%, or about 99% or more nucleotide or amino acid residue identity, when compared and aligned for maximum correspondence, as measured using a sequence comparison algorithm or by visual inspection. Such "substantially identical" sequences are typically considered to be "homologous", without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, at least about 250 residues, or over the full length of the two sequences to be compared.

Terms used herein pertaining to genetic manipulation are defined as follows.

Deletion: The removal of one or more nucleotides from a nucleic acid molecule or one or more amino acids from a protein, the regions on either side being joined together.

Derived: When used with reference to a nucleic acid or protein, "derived" means that the nucleic acid or polypeptide is isolated from a described source or is at least 70%, 80%, 90%, 95%, 99%, or more identical to a nucleic acid or polypeptide included in the described source.

Endogenous: As used herein with reference to a nucleic acid molecule and a particular cell, "endogenous" refers to a nucleic acid sequence or polypeptide that is in the cell and was not introduced into the cell using recombinant engineering techniques. For example, an endogenous gene is a gene that was present in a cell when the cell was originally isolated from nature.

Exogenous: As used herein with reference to a nucleic acid molecule or polypeptide in a particular cell, "exogenous" refers to any nucleic acid molecule or polypeptide that does not originate from that particular cell as found in nature. Thus, a non-naturally-occurring nucleic acid molecule or protein is considered to be exogenous to a cell once introduced into the cell. A nucleic acid molecule or protein that is naturally-occurring also can be exogenous to a particular cell. For example, an entire coding sequence isolated from cell X is an exogenous nucleic acid with respect to cell Y once that coding sequence is introduced into cell Y, even if X and Y are the same cell type. The term "heterologous" is used herein interchangeably with "exogenous."

Expression: The process by which a gene's coded information is converted into the structures and functions of a cell, such as a protein, transfer RNA, or ribosomal RNA. Expressed genes include those that are transcribed into mRNA and then translated into protein and those that are transcribed into RNA but not translated into protein (for example, transfer and ribosomal RNAs).

Introduce: When used with reference to genetic material, such as a nucleic acid, and a cell, "introduce" refers to the delivery of the genetic material to the cell in a manner such that the genetic material is capable of being expressed within the cell. Introduction of genetic material includes both transformation and transfection. Transformation encompasses techniques by which a nucleic acid molecule can be introduced into cells such as prokaryotic cells or non-animal eukaryotic cells. Transfection encompasses techniques by which a nucleic acid molecule can be introduced into cells such as animal cells. These techniques include but are not limited to introduction of a nucleic acid via conjugation, electroporation, lipofection, infection, and particle gun acceleration.

Isolated: An "isolated" biological component (such as a nucleic acid molecule, polypeptide, or cell) has been substantially separated or purified away from other biological components in which the component naturally occurs, such as other chromosomal and extrachromosomal DNA and RNA and proteins. Nucleic acid molecules and polypeptides that have been "isolated" include nucleic acid molecules and polypeptides purified by standard purification methods. The term also includes nucleic acid molecules and polypeptides prepared by recombinant expression in a cell as well as chemically synthesized nucleic acid molecules and polypeptides. In one example, "isolated" refers to a naturally-occurring nucleic acid molecule that is not immediately contiguous with both of the sequences with which it is immediately contiguous (one on the 5' end and one on the 3' end) in the naturally-occurring genome of the organism from which it is derived.

Nucleic acid: Encompasses both RNA and DNA molecules including, without limitation, cDNA, genomic DNA, and mRNA. Nucleic acids also include synthetic nucleic acid molecules, such as those that are chemically synthesized or recombinantly produced. The nucleic acid can be double-stranded or single-stranded. Where single-stranded, the nucleic acid molecule can be the sense strand, the antisense strand, or both. In addition, the nucleic acid can be circular or linear.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. An origin of replication is operably linked to a coding sequence if the origin of replication controls the replication or copy number of the nucleic acid in the cell. Operably linked nucleic acids may or may not be contiguous.

Operon: Configurations of separate genes that are transcribed in tandem as a single messenger RNA are denoted as operons. Thus, a set of in-frame genes in close proximity under the transcriptional regulation of a single promoter constitutes an operon. Operons may be synthetically generated using the methods described herein.

Overexpress: When a gene is caused to be transcribed at an elevated rate compared to the endogenous or basal transcription rate for that gene. In some examples, overexpression additionally includes an elevated rate of translation of the gene compared to the endogenous translation rate for that gene. Methods of testing for overexpression are well known in the art, for example transcribed RNA levels can be assessed using RT-PCR and protein levels can be assessed using SDS page gel analysis.

Recombinant: A recombinant nucleic acid molecule or polypeptide is one that has a sequence that is not naturally occurring, has a sequence that is made by an artificial combination of two otherwise separated segments of sequence, or both. This artificial combination can be achieved, for example, by chemical synthesis or by the artificial manipulation of isolated segments of nucleic acid molecules or polypeptides, such as genetic engineering techniques. "Recombinant" is also used to describe nucleic acid molecules that have been artificially manipulated but contain the same regulatory sequences and coding regions that are found in the organism from which the nucleic acid was isolated, such as an introduced additional copy of a nucleic acid molecule naturally present in the organism. A recombinant cell or microorganism is one that contains an exogenous nucleic acid molecule, such as a recombinant nucleic acid molecule.

Recombinant cell: A cell that comprises a recombinant nucleic acid.

Vector or expression vector: An entity comprising a nucleic acid molecule that is capable of introducing the nucleic acid, or being introduced with the nucleic acid, into a cell for expression of the nucleic acid. A vector can include nucleic acid sequences that permit it to replicate in the cell, such as an origin of replication. A vector can also include one or more selectable marker genes and other genetic elements known in the art. Examples of suitable vectors are found below.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below.

Exogenous nucleic acids can be introduced stably or transiently into a cell using techniques well known in the art, including electroporation, calcium phosphate precipitation, DEAE-dextran mediated transfection, liposome-mediated transfection, conjugation, transduction, and the like. For stable transformation, a nucleic acid can further include a selectable marker. Suitable selectable markers include antibiotic resistance genes that confer, for example, resistance to neomycin, tetracycline, chloramphenicol, or kanamycin, genes that complement auxotrophic deficiencies, and the like. (See below for more detail.)

Various embodiments of the invention use an expression vector that includes a heterologous nucleic acid encoding a protein involved in a metabolic or biosynthetic pathway. Suitable expression vectors include, but are not limited to viral vectors, phage vectors, bacteriophage vectors, plasmids, phagemids, cosmids, fosmids, bacterial artificial chromosomes, P1-based artificial chromosomes, yeast plasmids, yeast artificial chromosomes, and any other vectors specific for cells of interest.

Useful vectors can include one or more selectable marker genes to provide a phenotypic trait for selection of transformed cells. The selectable marker gene encodes a protein necessary for the survival or growth of transformed cells grown in a selective culture medium. Cells not transformed with the vector containing the selectable marker gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*. In alternative embodiments, the selectable marker gene is one that encodes dihydrofolate reductase or confers neomycin resistance (for use in eukaryotic cell culture), or one that confers tetracycline or ampicillin resistance (for use in a prokaryotic cell, such as *E. coli*).

The coding sequence in the expression vector is operably linked to an appropriate expression control sequence (promoters, enhancers, and the like) to direct synthesis of the encoded gene product. Such promoters can be derived from microbial or viral sources. Depending on the cell/vector system utilized, any of a number of suitable transcription and translation control elements, including constitutive and inducible promoters, transcription enhancer elements, transcription terminators, etc. can be used in the expression vector (see e.g., Bitter et al. (1987) *Methods in Enzymology*, 153:516-544).

Suitable promoters for use in prokaryotic cells include but are not limited to: promoters capable of recognizing the T4, T3, Sp6, and T7 polymerases; the $P_R$ and $P_L$ promoters of bacteriophage lambda; the trp, recA, heat shock, and lacZ promoters of *E. coli*; the alpha-amylase and the sigma-specific promoters of *B. subtilis*; the promoters of the bacteriophages of *Bacillus; Streptomyces* promoters; the int promoter of bacteriophage lambda; the bla promoter of the beta-lactamase gene of pBR322; and the CAT promoter of the chloramphenicol acetyl transferase gene. Prokaryotic promoters are reviewed by Glick, *J. Ind. Microbiol.* 1:277 (1987); Watson et al, Molecular Biology of the Gene, 4th Ed., Benjamin Cummins (1987); and Sambrook et al., In: *Molecular Cloning: A Laboratory Manual*, $3^{rd}$ ed., Cold Spring Harbor Laboratory Press (2001).

Non-limiting examples of suitable promoters for use within a eukaryotic cell are typically viral in origin and include the promoter of the mouse metallothionein I gene (Hamer et al. (1982) *J. Mol. Appl. Gen.* 1:273); the TK promoter of Herpes virus (McKnight (1982) *Cell* 31:355); the SV40 early promoter (Benoist et al. (1981) *Nature* (London) 290:304); the Rous sarcoma virus promoter; the cytomegalovirus promoter (Foecking et al. (1980) *Gene* 45:101); and the yeast gal4 gene promoter (Johnston et al. (1982) *PNAS* (USA) 79:6971; Silver et al. (1984) *PNAS* (USA) 81:5951.

Coding sequences can be operably linked to an inducible promoter. Inducible promoters are those wherein addition of an effector induces expression. Suitable effectors include proteins, metabolites, chemicals, or culture conditions capable of inducing expression. Suitable inducible promoters include but are not limited to the lac promoter (regulated by IPTG or analogs thereof), the lacUV5 promoter (regulated by IPTG or analogs thereof), the tac promoter (regulated by IPTG or analogs thereof), the trc promoter (regulated by IPTG or analogs thereof), the araBAD promoter (regulated by L-arabinose), the phoA promoter (regulated by phosphate starvation), the recA promoter (regulated by nalidixic acid), the proU promoter (regulated by osmolarity changes), the cst-I promoter (regulated by glucose starvation), the tetA promoter (regulated by tetracycline), the cadA promoter (regulated by pH), the nar promoter (regulated by anaerobic conditions), the $p_L$ promoter (regulated by thermal shift), the cspA promoter (regulated by thermal shift), the T7 promoter (regulated by thermal shift), the T7-lac promoter (regulated by IPTG), the T3-lac promoter (regulated by IPTG), the T5-lac promoter (regulated by IPTG), the T4 gene 32 promoter (regulated by T4 infection), the nprM-lac promoter (regulated by IPTG), the VHb promoter (regulated by oxygen), the metallothionein promoter (regulated by heavy metals), the MMTV promoter (regulated by steroids such as dexamethasone) and variants thereof.

Alternatively, a coding sequence can be operably linked to a repressible promoter. Repressible promoters are those wherein addition of an effector represses expression. Examples of repressible promoters include but are not limited to the trp promoter (regulated by tryptophan); tetracycline-repressible promoters, such as those employed in the "TET-OFF"-brand system (Clontech, Mountain View, Calif.); and variants thereof.

In some versions, the cell is genetically modified with a heterologous nucleic acid encoding a biosynthetic pathway gene product that is operably linked to a constitutive promoter. Suitable constitutive promoters are known in the art.

In some versions, the cell is genetically modified with an exogenous nucleic acid encoding a single protein. In other embodiments, a modified cell is one that is genetically modified with exogenous nucleic acids encoding two or more proteins. Where the cell is genetically modified to express two or more proteins, those nucleic acids can each be contained in a single or in separate expression vectors. When the nucleic acids are contained in a single expression vector, the nucleotide sequences may be operably linked to a common control element (e.g., a promoter), that is, the common control element controls expression of all of the coding sequences in the single expression vector.

When the cell is genetically modified with heterologous nucleic acids encoding two or more proteins, one of the nucleic acids can be operably linked to an inducible promoter, and one or more of the nucleic acids can be operably linked to a constitutive promoter. Alternatively, all can be operably linked to inducible promoters or all can be operably linked to constitutive promoters.

Nucleic acids encoding enzymes desired to be expressed in a cell may be codon-optimized for that particular type of cell. Codon optimization can be performed for any nucleic acid by "OPTIMUMGENE"-brand gene design system by GenScript (Piscataway, N.J.).

The introduction of a vector into a bacterial cell may be performed by protoplast transformation (Chang and Cohen (1979) *Molecular General Genetics,* 168:111-115), using competent cells (Young and Spizizen (1961) *Journal of Bacteriology,* 81:823-829; Dubnau and Davidoff-Abelson (1971) *Journal of Molecular Biology,* 56: 209-221), electroporation (Shigekawa and Dower (1988) *Biotechniques,* 6:742-751), or conjugation (Koehler and Thorne (1987) *Journal of Bacteriology,* 169:5771-5278). Commercially available vectors for expressing heterologous proteins in bacterial cells include but are not limited to pZERO, pTrc99A, pUC19, pUC18, pKK223-3, pEX1, pCAL, pET, pSPUTK, pTrxFus, pFastBac, pThioHis, pTrcHis, pTrcHis2, and pLEx, in addition to those described in the following Examples.

Methods for transforming yeast cells with heterologous DNA and producing heterologous polypeptides therefrom are disclosed by Clontech Laboratories, Inc., Palo Alto, Calif., USA (in the product protocol for the "YEAST-MAKER"-brand yeast transformation system kit); Reeves et al. (1992) *FEMS Microbiology Letters* 99:193-198; Manivasakam and Schiestl (1993) *Nucleic Acids Research* 21(18): 4414-5; and Ganeva et al. (1994) *FEMS Microbiology Letters* 121:159-64. Expression and transformation vectors for transformation into many yeast strains are available. For example, expression vectors have been developed for the following yeasts: *Candida albicans* (Kurtz, et al. (1986) *Mol. Cell. Biol.* 6:142); *Candida maltosa* (Kunze et al. (1985) *J. Basic Microbiol.* 25:141); *Hansenula polymorpha* (Gleeson et al. (1986) *J. Gen. Microbiol.* 132:3459) and Roggenkamp et al. (1986) *Mol. Gen. Genet.* 202:302); *Kluyveromyces fragilis* (Das et al. (1984) *J. Bacteriol.* 158:1165); *Kluyveromyces lactis* (De Louvencourt et al. (1983) *J. Bacteriol.* 154:737) and Van den Berg et al. (1990) Bio/Technology 8:135); *Pichia quillerimondii* (Kunze et al. (1985) *J. Basic Microbiol.* 25:141); *Pichia pastoris* (Cregg et al. (1985) *Mol. Cell. Biol.* 5:3376; U.S. Pat. Nos. 4,837, 148; and 4,929,555); *Saccharomyces cerevisiae* (Hinnen et al. (1978) *Proc. Natl. Acad. Sci. USA* 75:1929 and Ito et al. (1983) *J. Bacteriol.* 153:163); *Schizosaccharomyces pombe* (Beach et al. (1981) *Nature* 300:706); and *Yarrowia lipolytica* (Davidow et al. (1985) *Curr. Genet.* 10:380-471 and Gaillardin et al. (1985) *Curr. Genet.* 10:49).

Suitable procedures for transformation of *Aspergillus* cells are described in EP 238 023 and U.S. Pat. No. 5,679, 543. Suitable methods for transforming Fusarium species are described by Malardier et al., *Gene,* 1989, 78:147-56 and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al. (1983) *Journal of Bacteriology,* 153: 163; and Hinnen et al. (1978) *PNAS USA,* 75:1920.

The microorganisms of the invention are particularly suited to co-consuming glucose with non-glucose carbohydrates, such as xylose. Accordingly, methods of the invention comprise culturing a microorganism of the invention in a medium comprising glucose and xylose. The xylose may be present at any level within the medium. The glucose and xylose may each independently be present in the medium at least at 5 g/l, 10 g/l, 15 g/l, 20 g/l, 25 g/l, 30 g/l, 35 g/l, 40 g/l, 45 g/l, 50 g/l, 55 g/l, 60 g/l, 65 g/l, 70 g/l, 75 g/l, 80 g/l, 85 g/l, 90 g/l, 95 g/l, 100 g/l, 110 g/l, 120 g/l, 130 g/l or even more. The medium may also comprise other components, including those derived from a biomass or lignocellulosic material such as cellobiose, arabinose, and rhamnose.

In culturing the microorganism, the microorganism may consume at least about 1%, 2.5%, 5%, 7.5%, or 10% of the initial amount of xylose in the medium during the time the microorganism consumes about 10% of the initial amount of glucose in the medium; at least about 5%, 10%, 15%, or 20% of the initial amount of xylose in the medium during the time the microorganism consumes about 20% of the initial amount of glucose in the medium; at least about 10%, 15%, 20%, 25%, or 30% of the initial amount of xylose in the medium during the time the microorganism consumes about 30% of the initial amount of glucose in the medium; at least about 10%, 20%, 25%, 30%, 35%, or 40% of the initial amount of xylose in the medium during the time the microorganism consumes about 40% of the initial amount of glucose in the medium; at least about 10%, 20%, 30%, 35%, 40%, 45%, or 50% of the initial amount of xylose in the medium during the time the microorganism consumes about 50% of the initial amount of glucose in the medium; at least about 20%, 40%, 45%, 50%, 55%, or 60% of the initial amount of xylose in the medium during the time the microorganism consumes about 60% of the initial amount of glucose in the medium; at least about 40%, 50%, 55%, 60%, 65%, or 70% of the initial amount of xylose in the medium during the time the microorganism consumes about 70% of the initial amount of glucose in the medium; at least about 50%, 60%, 65%, 70%, 75%, or 80% of the initial amount of xylose in the medium during the time the microorganism consumes about 80% of the initial amount of glucose in the medium; or at least about 50%, 60%, 70%, 75%, 80%, 85%, or 90% of the initial amount of xylose in the medium during the time the microorganism consumes about 90% of the initial amount of glucose in the medium.

In some versions, the medium comprises a biomass hydrolysate. Biomass is biological material derived from living or once-living organisms. Biomass can be from plant, animal, or other organic material. Biomass is carbon based and is composed of a mixture of organic molecules containing hydrogen, usually including atoms of oxygen, often nitrogen and also small quantities of other atoms, including alkali, alkaline earth and heavy metals. The biomass hydrolysate for use in the present invention can be produced from any biomass feedstock. Exemplary types of biomass feedstocks include sucrose-rich feedstocks such as suger cane; starchy materials, such as corn grain; and lignocellulosic biomass, such as costal Bermuda grass, switchgrass (*Pancium virgatum*), corn cobs, corn stover, cotton seed hairs, grasses, hardwood, hardwood stems, maple, leaves, newspaper, sugarcane bagasse, nut shells, paper, primary wastewater solids, softwood, softwood stems, pine loblolly pine, solid cattle manure, sorted refuse, grain hulls, swine waste, switchgrass, waste papers from chemical pulps, wheat straw, wood, wood chips, wood pulp, woody residues *Miscanthus*, date palm (*Phoenix dectylifera*), oil palm, *Sorghum*, and *Arundo donax*.

Prior to hydrolysis, the biomass feedstock may be pretreated or non-pretreated. Pretreatment of biomass feedstock removes a large proportion of the lignin and other materials and enhances the porosity of the biomass prior to hydrolysis. The biomass feedstock may be pretreated by any method. Exemplary pretreatments include chipping, grinding, milling, steam pretreatment, ammonia fiber expansion (AFEX, also referred to as ammonia fiber explosion), ammonia recycle percolation (ARP), $CO_2$ explosion, steam explosion, ozonolysis, wet oxidation, acid hydrolysis, dilute-acid hydrolysis, alkaline hydrolysis, ionic liquid, organosolv, and pulsed electrical field treatment, among others. See, e.g., Kumar et al. 2009 and da Costa Lopes et al. 2013.

The pretreated or non-pretreated biomass may be hydrolyzed by any suitable method. Hydrolysis converts biomass polymers to fermentable sugars, such as glucose and xylose, and other monomeric or oligomeric components. Exemplary hydrolysis methods include enzymatic hydrolysis (e.g., with cellulases or other enzymes), acid hydrolysis (e.g., with sulfurous, sulfuric, hydrochloric, hydrofluoric, phosphoric, nitric, and/or formic acids), and ionic liquid hydrolysis (e.g., with 1-ethyl-3-methylimidazolium chloride) (Binder et al. 2010) among other methods. The hydrolysate may be in aqueous solution, concentrated, or dehydrated.

The microorganisms of the invention are particularly suited for producing ethanol from the consumption of carbohydrates such as glucose and/or xylose. Accordingly, methods of the invention comprise culturing a microorganism in a medium for a time sufficient to produce an amount of ethanol. The medium in such culturing may comprise glucose and xylose and/or may be a biomass hydrolysate as described above. The culturing may produce ethanol in an amount of at least about 10 mM, 25 mM, 50 mM, 75 mM, 100 mM, 150 mM, 200 mM, 250 mM, 300 mM, 350 mM, 400 mM, 450 mM, 500 mM, 550 mM, 600 mM, 650 mM, 700 mM, 750 mM, 800 mM, 850 mM, 900 mM or more. The culturing may produce a yield of ethanol based on the consumption of glucose and xylose of at least about 50%, 60%, 70%, 75%, 80%, 85%, 90%, 95%, 97%, 99% or more.

Prior to the culturing described herein, the microorganisms of the invention may be adapted to growth in the presence of certain components through adaptive evolution. Such components may comprise any one or more of glucose, xylose, ethanol, and biomass hydrolysate. The adapting may comprise serially passing the microorganisms in media comprising constant or increasing amounts of one or more of the components. In some versions, the adapting may comprise serially passing the microorganisms in media comprising constant or increasing amounts of one or more of the components to the exclusion of another one or more of the components. In some versions, the adapting may comprise serially passing the microorganisms in media comprising constant or increasing amounts of a first set of components and then serially passing the microorganisms in media comprising constant or increasing amounts of a second set of components, wherein the first set of components is different from the second set of components. In some versions, the adapting may comprise serially passing the microorganisms in media comprising constant or increasing amounts of a first set of components, then serially passing the microorganisms in media comprising constant or increasing amounts of a second set of components, and then serially passing the microorganisms in media comprising constant or increasing amounts of a third set of components, wherein at least two or all three of the first set of components, the second set of components and the third set of components are different from each other.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLE

Introduction

Efficient conversion of lignocellulose-derived sugars to ethanol and other biofuels is a crucial step in sustainable bioenergy production from biomass. Glucose and xylose are the major sugars in pretreated lignocellulosic hydrolysate, and can both be converted by microorganisms into ethanol and other biofuels. However, microbial conversion of these sugars in lignocellulosic hydrolysate is hindered by the fact that microbes preferentially consume glucose first and do not consume xylose after glucose is depleted. This has been attributed to stresses associated with growth in hydrolysate (e.g., inhibitors produced from pretreatment, ethanol produced by fermentation, and high osmolarity).

Computational models of metabolic networks have been successfully used to study and engineer microbial metabolism to produce valuable chemicals. We used genome-scale metabolic models of *Escherichia coli* to identify gene knockout strategies to improve co-utilization of glucose and xylose in lignocellulosic hydrolysate (FIG. 1). Using the computational predictions, we constructed gene knockout mutants with inserted *Zymomonas mobilis* pyruvate decarboxylase and alcohol dehydrogenase genes to increase conversion of sugars to ethanol.

The constructed *E. coli* strains co-utilized glucose and xylose anaerobically in minimal media, but their growth and glucose uptake rates were much slower than the parental *E. coli* strain's. The engineered strains were then adaptively evolved in minimal media containing (1) glucose, (2) glucose and xylose, and (3) glucose and gradually increasing concentrations of ethanol. The evolved strains were able to simultaneously convert glucose and xylose into ethanol when grown in a synthetic hydrolysate (SynH) medium. In addition, two of the evolved strains co-utilized most of the glucose and xylose in ammonia fiber explosion (AFEX) pre-treated corn stover and switchgrass hydrolysates. The developed strains show significantly improved conversion of sugars into ethanol in lignocellulosic hydrolysates and provide a platform that may be further engineered to produce next-generation biofuels.

Material and Methods

Computational Strain Design for Improved Conversion of Glucose and Xylose to Ethanol Genome-scale metabolic and transcriptional regulatory models of *Escherichia coli* (Reed et al. 2003, Covert et al. 2004, Feist et al. 2007, Barua et al. 2010, Orth et al. 2011) were used to identify genetic perturbations to improve the conversion of glucose and xylose to ethanol. The *E. coli* metabolic models were augmented with reactions catalyzed by *Zymomonas mobilis* pyruvate decarboxylase and alcohol dehydrogenase. A bi-level strain design method, OptORF (Kim et al. 2010), was first used to find metabolic gene or transcription factor deletions that would couple cellular growth and ethanol production in a minimal medium containing glucose and xylose. An uptake rate of 10 mmol/gDW/hr was used for glucose or xylose to simulate minimal media containing either glucose or xylose, and glucose uptake rate of 6 mmol/gDW/hr and xylose uptake rate of 4 mmol/gDW/hr were used to simulate minimal media containing both glucose and xylose. A flux prediction method, RELATCH (Kim et al. 2012), was used to find metabolic gene deletions that would improve xylose utilization in the presence of glucose. Among the genetic perturbation strategies identified by OptORF, the strategies that include the gene deletions identified by RELATCH were selected for experimental characterization.

Strain Construction and Adaptive Evolution

*E. coli* K-12 MG1655 was used to construct the strains based on the computational design. A PET cassette containing *Z. mobilis* pyruvate decarboxylase ($pdc_{Zm}$) and alcohol dehydrogenase ($adhB_{Zm}$), and chloramphenicol resistance marker (cat) was inserted into the pflB locus as described in a previous study (Schwalbach et al. 2012). The rest of genes were subsequently deleted using P1 transduction or other previously described methods (Baba et al. 2006, Datsenko et al. 2000).

TABLE 1

List of plasmids and strains

| Plasmids/Strains | Genotype |
| --- | --- |
| pPET | $pdc_{Zmo}$ $adhB_{Zmo}$ (pJGG2, Gardner et al. 2010) |
| Parent | *E. coli* K-12 MG1655 |
| JK10 | ldhA::kan pflB::($pdc_{Zmo}$ $adhB_{Zmo}$ cat) |
| JK10 pPET | JK10 with pPET |
| JK20 | ldhA::kan pflB::($pdc_{Zmo}$ $adhB_{Zmo}$ cat) Δpgi ΔgntR |
| JK20 pPET | JK20 with pPET |
| JK20E | JK20 adaptively evolved in M9 + glucose, xylose, ethanol |
| JK20E pPET | Isolate of JK20E with pPET |
| JK30 | ldhA::kan pflB::($pdc_{Zmo}$ $adhB_{Zmo}$ cat) ΔptsH |
| JK30E | JK30 adaptively evolved in M9 + xylose |
| JK31 | ΔldhA pflB::($pdc_{Zmo}$ $adhB_{Zmo}$ cat) ΔptsH fruB::kan (glc⁻) (from JK30) |
| JK32 | ΔldhA pflB::($pdc_{Zmo}$ $adhB_{Zmo}$ cat) ΔptsH fruB::kan (glc⁺) (isolate of JK31 grown on M9 glucose agar plates) |
| JK32 pPET | JK32 with pPET |
| JK32E | JK32 adaptively evolved in M9 + glucose, xylose, ethanol |
| JK32E pPET | isolate of JK32E with pPET |
| JK33E | ΔldhA pflB::($pdc_{Zmo}$ $adhB_{Zmo}$ cat) ΔptsH ΔfruB frdA::kan (derived from isolate from JK32E) |
| JK33E pPET | JK33E with pPET |

The constructed strain JK30 was adaptively evolved at 37° C. by transferring cells to a fresh M9 minimal medium containing 2 g/L xylose at mid-exponential phase repeatedly. The adaptively evolved strain after 7 serial transfers was designated as JK30E. The strain JK31, which was derived from JK30, initially did not grow on glucose as a sole carbon source. Aliquots of cells were plated on glucose M9 agar plates and colonies were found after incubating at 37° C. for a few days, and an isolate was found that was able to grow in a M9 medium containing 2 g/L glucose (designated as JK32). The strains JK20 and JK32 were then each independently adaptively evolved at 37° C. by transferring cells to a fresh medium at mid-exponential phase, repeatedly. First, cells were transferred five times in M9 minimal media containing 10 g/L glucose and five times in M9 minimal media containing 6 g/L glucose and 4 g/L xylose to improve sugar uptake. Next, cells were transferred five times in M9 minimal media containing 10 g/L glucose with ethanol concentration from 1% to 5% (v/v) increased by 1% at each transfer. Cells were then transferred five times in M9 minimal media containing 10 g/L glucose and 5% ethanol to increase ethanol tolerance. Overall, the strains JK20 and JK32 were adaptively evolved independently for a total of ~100 generations, and the evolved strains were designated as JK20E and JK32E, respectively. After the adaptive evolution, an additional copy of the PET cassette with gentamycin resistance marker on a plasmid (pPET) (Schwalbach et al. 2012) was transformed into the strains and single colonies were isolated on LB agar plates containing gentamycin. Strains containing the pPET plasmids are labeled accordingly (e.g., JK20E pPET).

Strain Characterization and Growth Condition

The initial characterization of the constructed strains was performed anaerobically in a M9 medium containing 6 g/L glucose and 4 g/L xylose to evaluate sugar utilization and ethanol production. The medium was flushed with $N_2$ gas and cultures were maintained anaerobic in Hungate tubes. Subsequent characterization in a synthetic hydrolysate medium (without lignocellulose-derived inhibitors) containing 60 g/L glucose and 30 g/L xylose (Keating et al. 2014) was done using 125 ml flasks with 50 ml of working volume in an anaerobic chamber sparged with 80% $N_2$, 10% $CO_2$, and 10% $H_2$ gas. In order to prevent the pH of cultures from decreasing significantly due to succinate production, 300 mM of phosphate buffer at pH 7 was added to the synthetic hydrolysate medium in flask experiments.

Fermentation experiments were conducted in duplicates using 250 ml mini-bioreactors (Applikon Biotechnology) with 100 ml of synthetic hydrolysate (SynH), ammonia fiber explosion (AFEX)-treated corn stover hydrolysate (ACSH), or AFEX-treated switchgrass hydrolysate (ASGH). The bioreactors were sparged with 95% $N_2$ and 5% $CO_2$ mixture gas at a flow rate of 20 ml/min, stirred at 500 rpm, and maintained at pH 7 and 37° C. Due to the sparging, the ethanol was evaporated from the culture and the amount of evaporated ethanol was estimated by a simple mass transfer model using data from an independent ethanol evaporation experiment.

Results

Computational Strain Designs to Improve Conversion of Glucose and Xylose to Ethanol We identified genetic perturbations that would improve conversion of glucose and xylose to ethanol using genome-scale metabolic and transcriptional regulatory models of *E. coli*. The lactate dehydrogenase and pyruvate formate-lyase reactions were removed from the *E. coli* metabolic models and the *Zymomonas mobilis* pyruvate decarboxylase and alcohol dehydrogenase reactions were added to represent the ΔldhA pflB::(pdc$_{Zmo}$ adhB$_{Zmo}$ cat) genotype of a base strain (JK10) used in this study.

First, we used OptORF to find metabolic or transcriptional regulatory gene deletions that would improve ethanol production at the maximal growth rate. Metabolic models (Reed et al. 2003, Feist et al. 2007) or integrated metabolic and transcriptional regulatory models (Covert et al. 2004, Barua et al. 2010) were employed to generate diverse sets of genetic perturbation strategies to couple growth and ethanol production from glucose and/or xylose.

We then used RELATCH to find metabolic gene deletions that would improve the xylose uptake in a minimal medium containing glucose and xylose. The phenotype and gene expression of GLBRCE1 *E. coli* strain (Keating et al. 2014) was used to generate a reference metabolic state for RELATCH predictions. We evaluated the effect of single gene deletions on the xylose uptake rate under two different cases where cells are using only glucose or both glucose and xylose in the reference state. Among the identified gene deletions that would improve the xylose uptake rate in both RELATCH simulation cases, the deletion of phosphoglucoisomerase (pgi) or phosphoenolpyruvate phosphotransferase system (ptsH or ptsI) was also part of the strategies identified by OptORF. In the strategies involving the pgi deletion, the deletion of GntR transcriptional repressor was also found to remove the repression of Entner-Doudoroff pathway genes. We constructed two *E. coli* strains based on these results (Table 2).

TABLE 2

Computationally predicted growth and ethanol production for different strains

| | Rate (mmol/gDW/hr) | | | | |
|---|---|---|---|---|---|
| Strains | Glucose Uptake | Xylose Uptake | Ethanol Production | Growth Rate (1/hr) | Ethanol Yield (%) |
| JK10 and JK10 pPET | 10 | 5 | 22.6 | 0.37 | 79.7 |
| JK20 and JK20 pPET | 10 | 5 | 23.8 | 0.29 | 84.1 |
| JK30 and JK30 pPET | 10 | 5 | 23.0 | 0.34 | 81.2 |

Figure 2A:
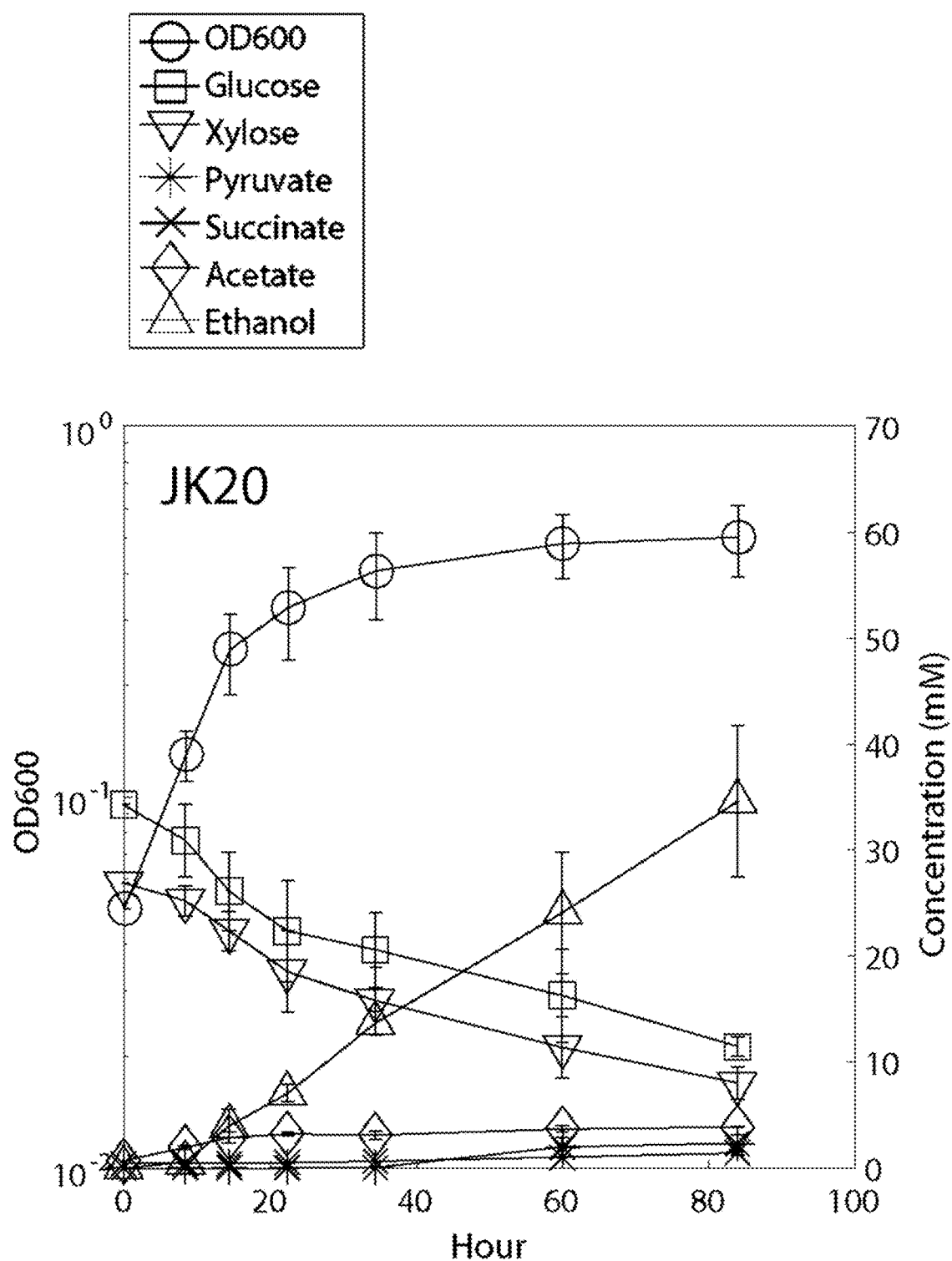
FIGS. 2A-2D show growth (OD600) and compound concentrations versus time for microorganisms of the invention cultured anaerobically in a minimal medium containing glucose and xylose.
Figure 2B:
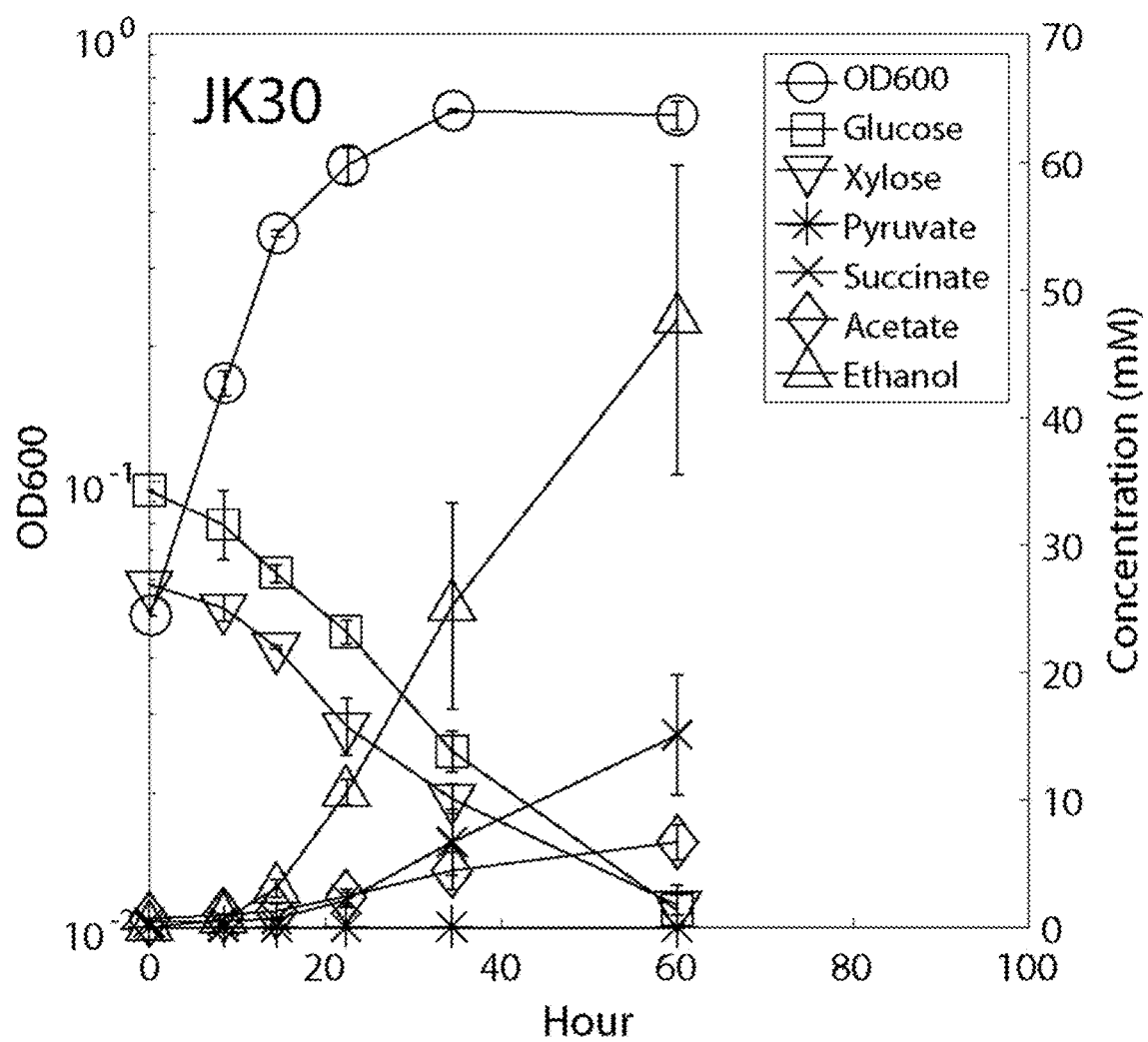
Figure 2C:
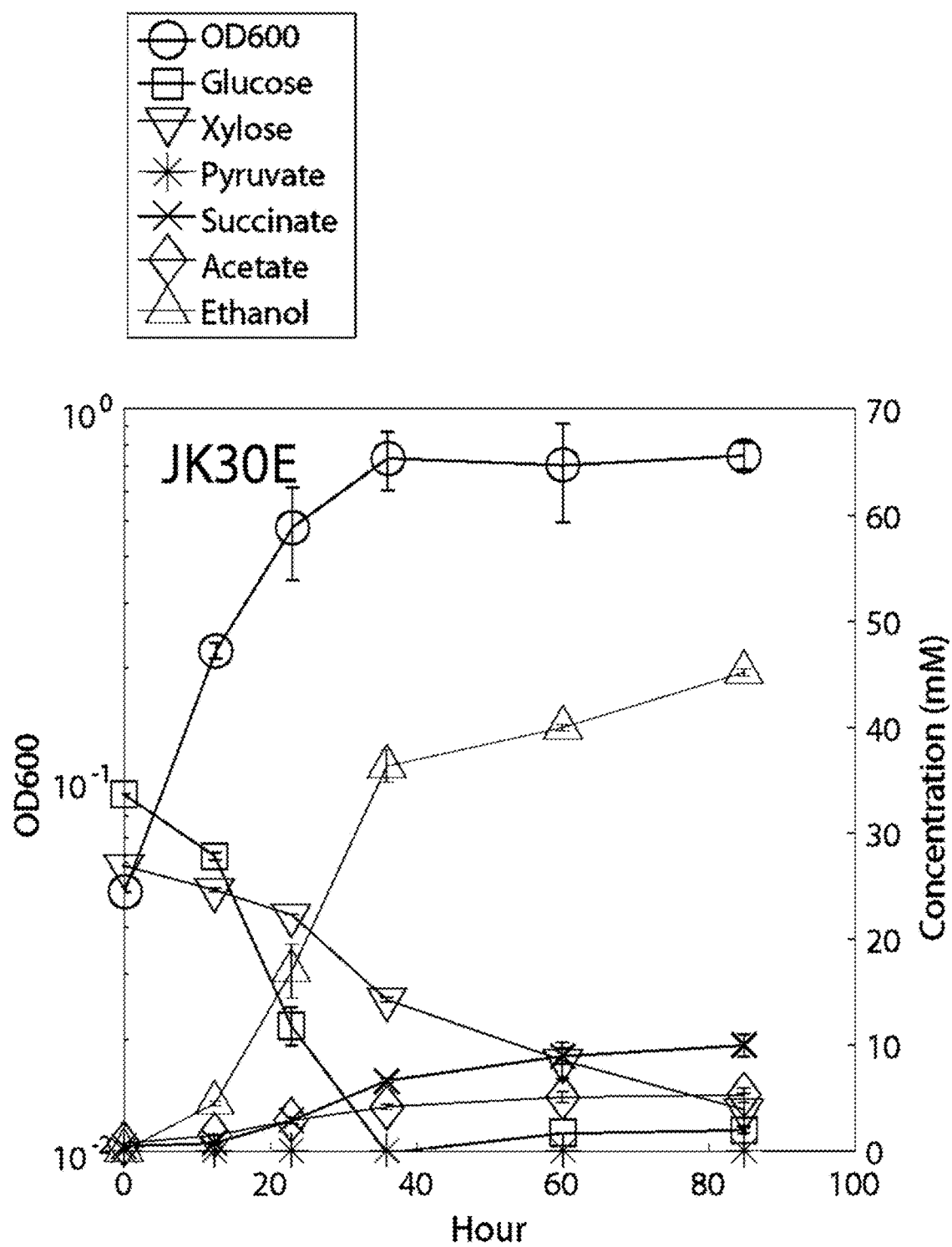

Co-Utilization of Glucose and Xylose by Engineered *E. coli* Strains in a Minimal Medium The two computationally designed strains JK20 and JK30 were grown anaerobically in a M9 minimal medium containing 6 g/L of glucose and 4 g/L of xylose. Both JK20 and JK30 co-utilized glucose and xylose and produced ethanol (FIGS. 2A and 2B). While JK20 produced mainly ethanol from glucose and xylose, JK30 also produced some succinate and acetate as co-products. Since the overall conversion was slow in both strains, they were adaptively evolved in a M9 minimum medium containing 2 g/L xylose to improve the conversion of xylose to ethanol. However, after 7 serial transfers, we found that evolved strain JK30E showed a 2-fold increase in glucose uptake but had a 2-fold decrease in xylose uptake (FIG. 2C) when grown in M9 media with glucose and xylose. This was unexpected since the cells were adaptively evolved in the absence of glucose.

Figure 2D:
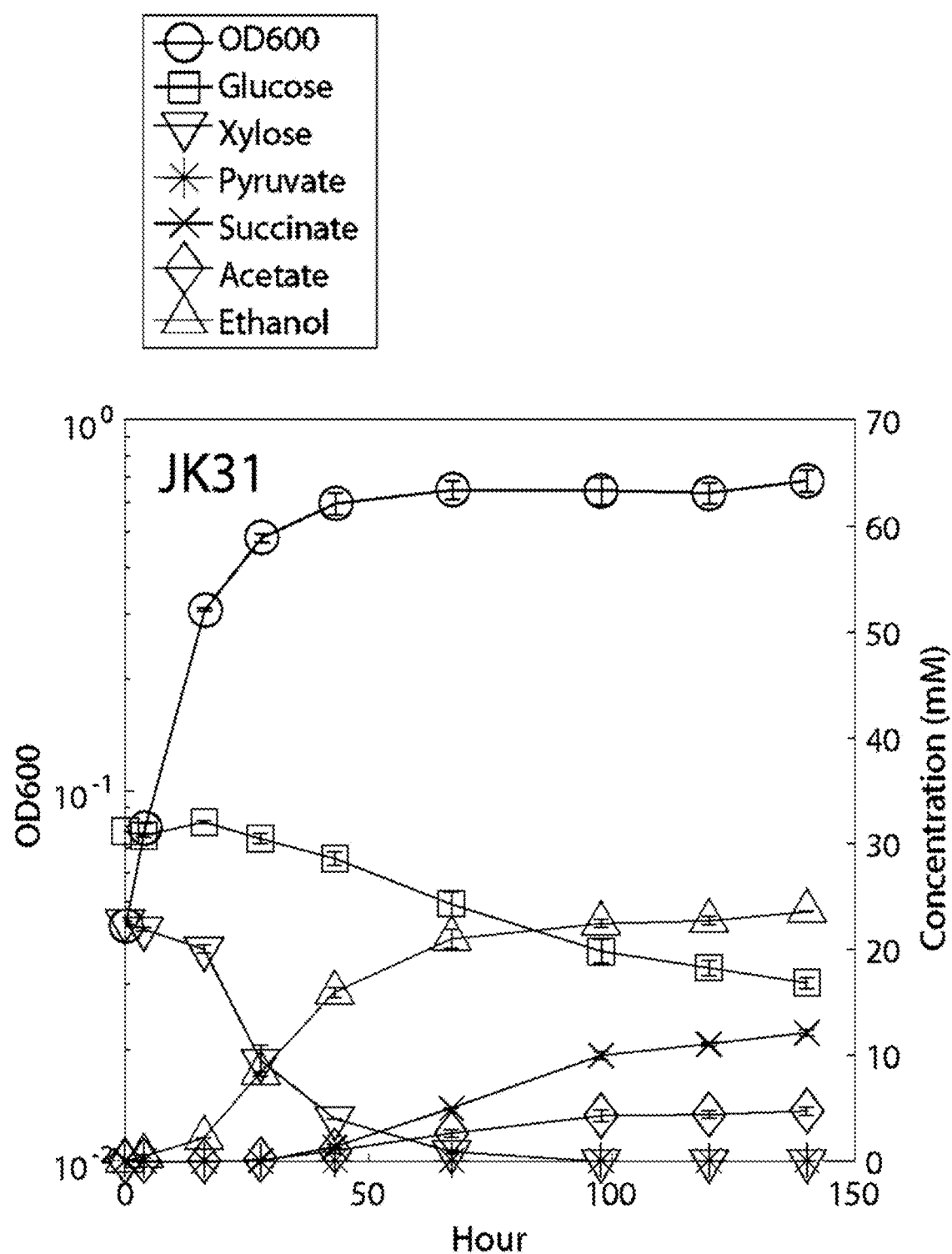

Sequencing of JK30E found mutations in the fruR gene, exclusively either a point mutation (N50K, 2 out of 6) or an in-frame deletion (957-962del, 4 out of 6). The fruR product regulates expression of the fruBKA operon, and FPr (encoded by fruB) can substitute for HPr (encoded by ptsH) (Saier et al. 1996). When the fruB gene was removed from JK30, the resulting strain JK31 had very slow glucose uptake when grown in a M9 minimal medium containing 6 g/L of glucose and 4 g/L of xylose (FIG. 2D), and did not grow in a M9 minimal medium containing 10 g/L of glucose. A culture of JK31 cells were plated on M9-glucose agar plates and placed in an incubator at 37° C., and colonies were found and isolated after two days. These cells were able to grow in a M9 minimal medium containing 10 g/L of glucose, and one isolate was designated as JK32.

Adaptive Evolution of Co-Utilization Strains in Minimal Media

The strains JK20 and JK32 were adaptively evolved in M9 minimal media to improve the conversion of sugars to ethanol. Cells were first adaptively evolved in a medium containing 10 g/L of glucose, and subsequently in a medium containing 6 g/L of glucose and 4 g/L of xylose. Next, cells were adaptively evolved in a medium containing 10 g/L of glucose and 1%-5% (v/v) ethanol, where the ethanol concentration was increased by 1% at each transfer. At 5% ethanol, the growth inhibition was significant and cells were again adaptively evolved in a medium containing 10 g/L of glucose and 5% ethanol. The resulting strains were designated as JK20E and JK32E, respectively.

Figure 3A:
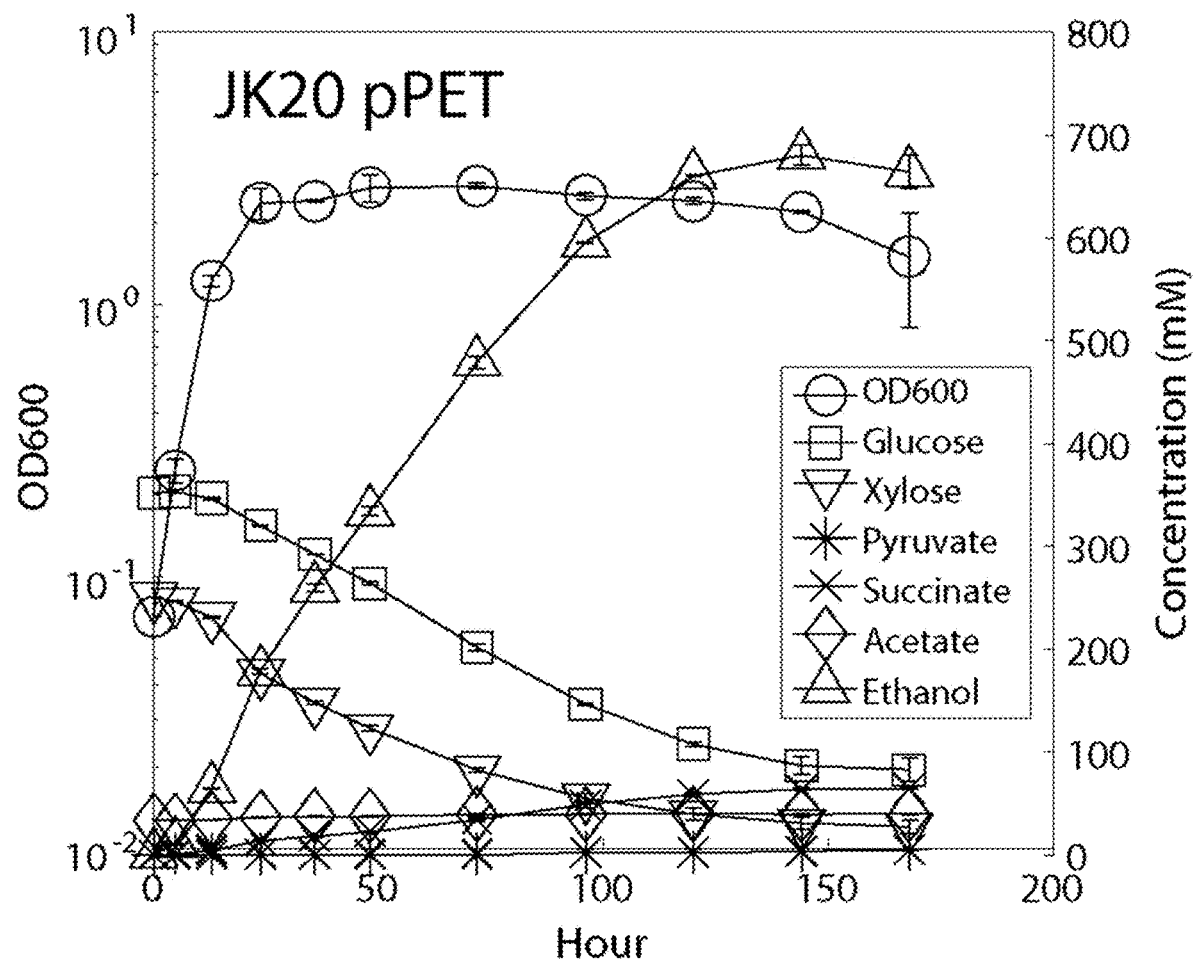
FIGS. 3A-3E show growth (OD600) and compound concentrations versus time for microorganisms of the invention cultured anaerobically in shake flasks in a synthetic hydrolysate medium (SynH, which lacks lignotoxins).
Figure 3B:
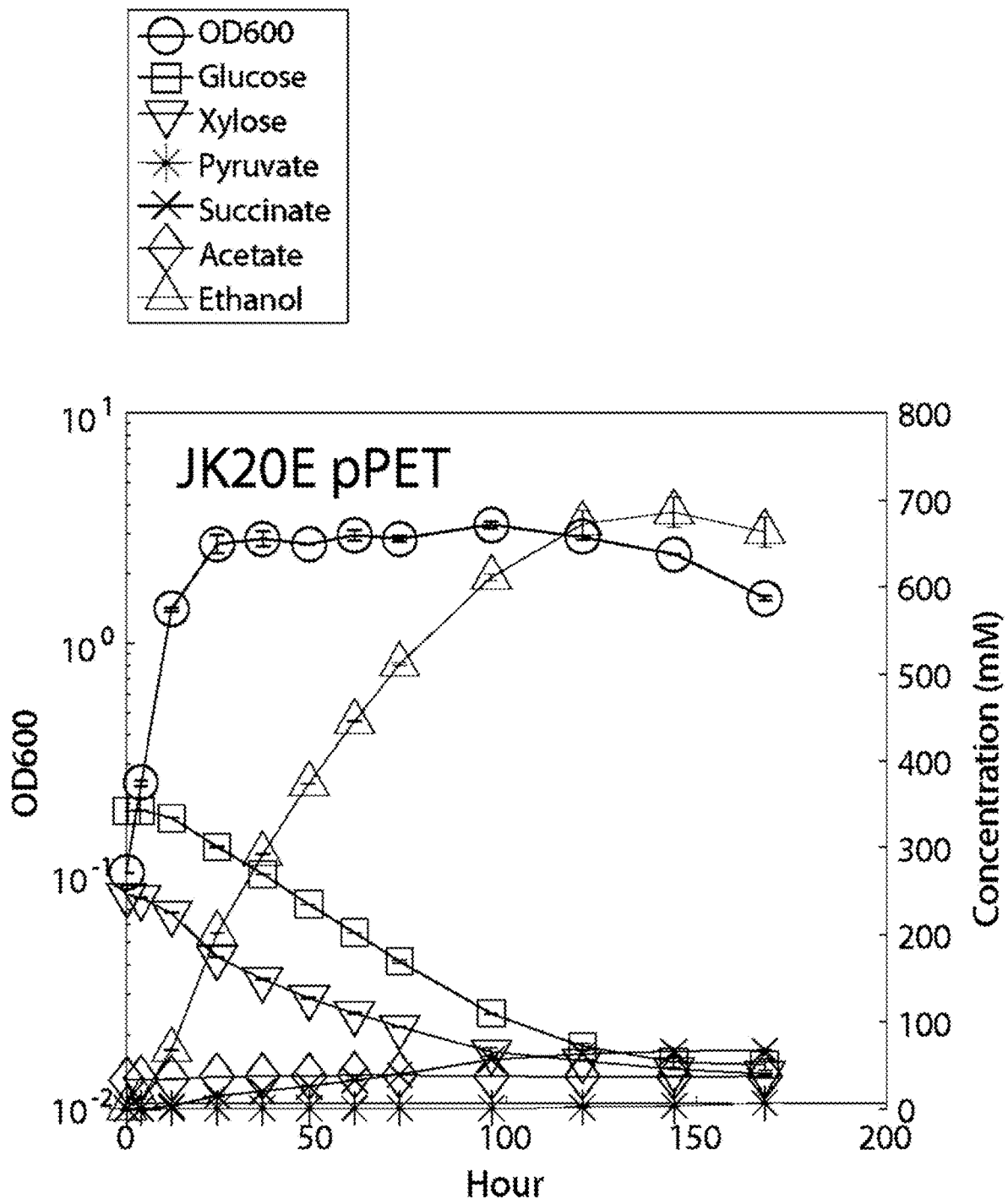
Figure 3C:
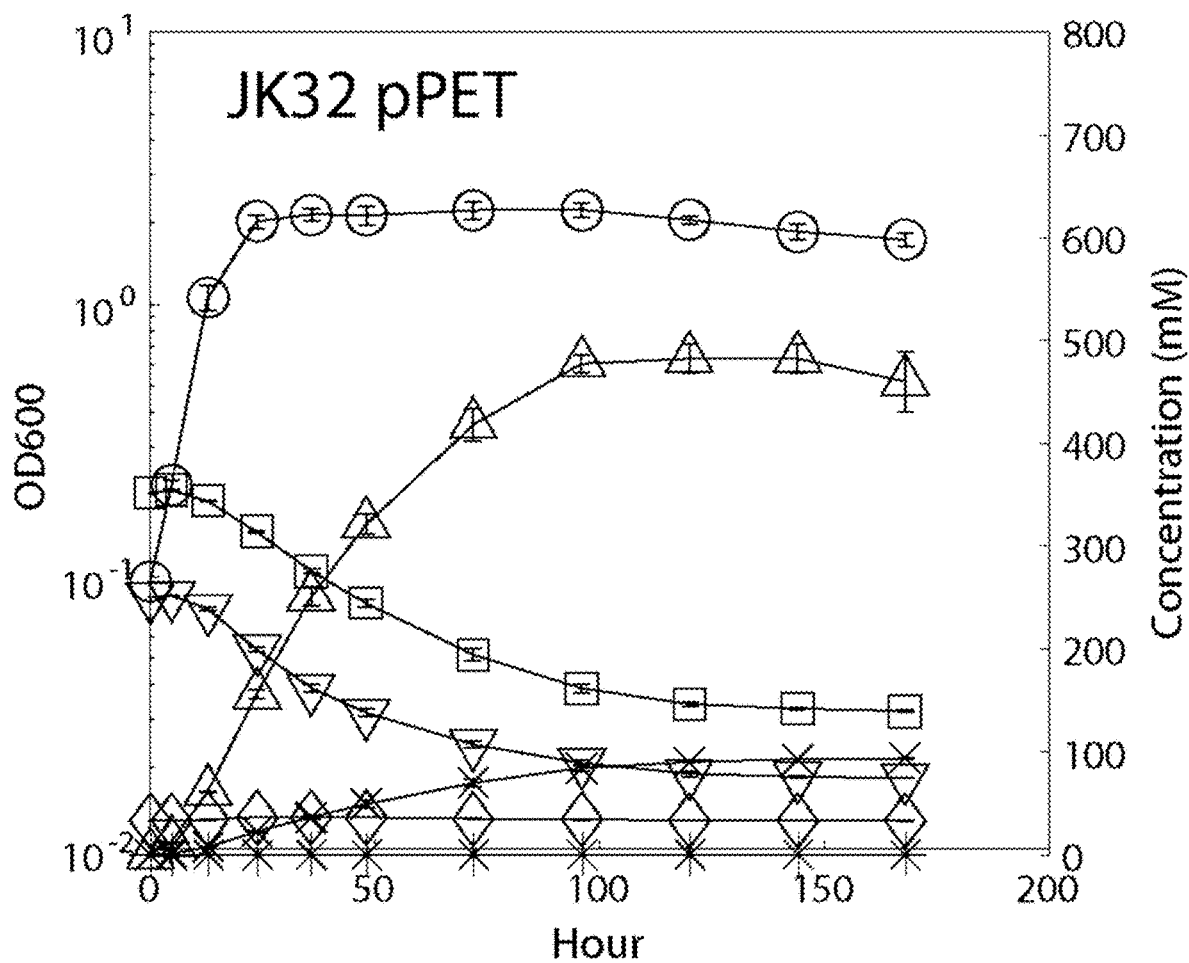
Figure 3D:
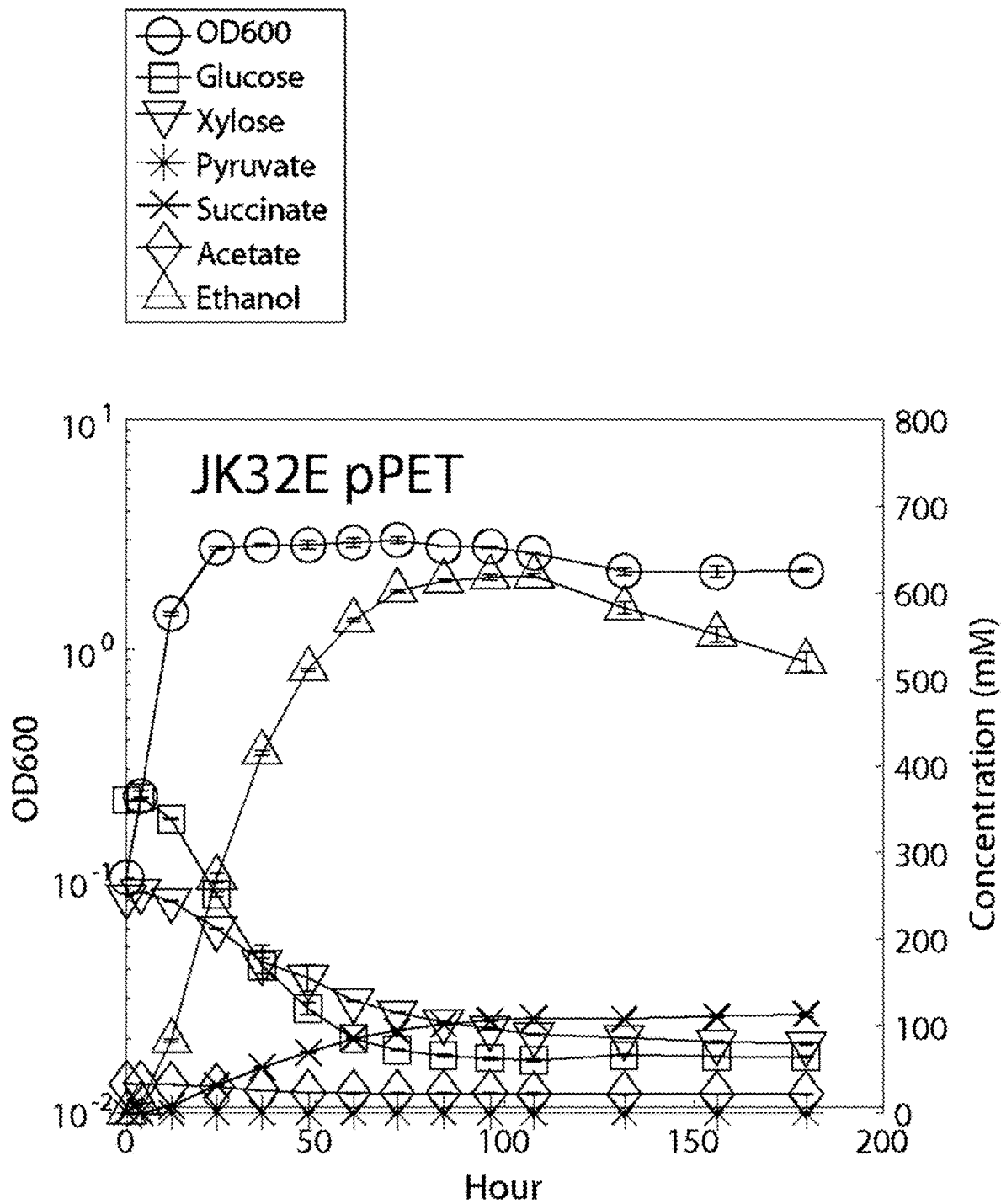
Figure 3E:
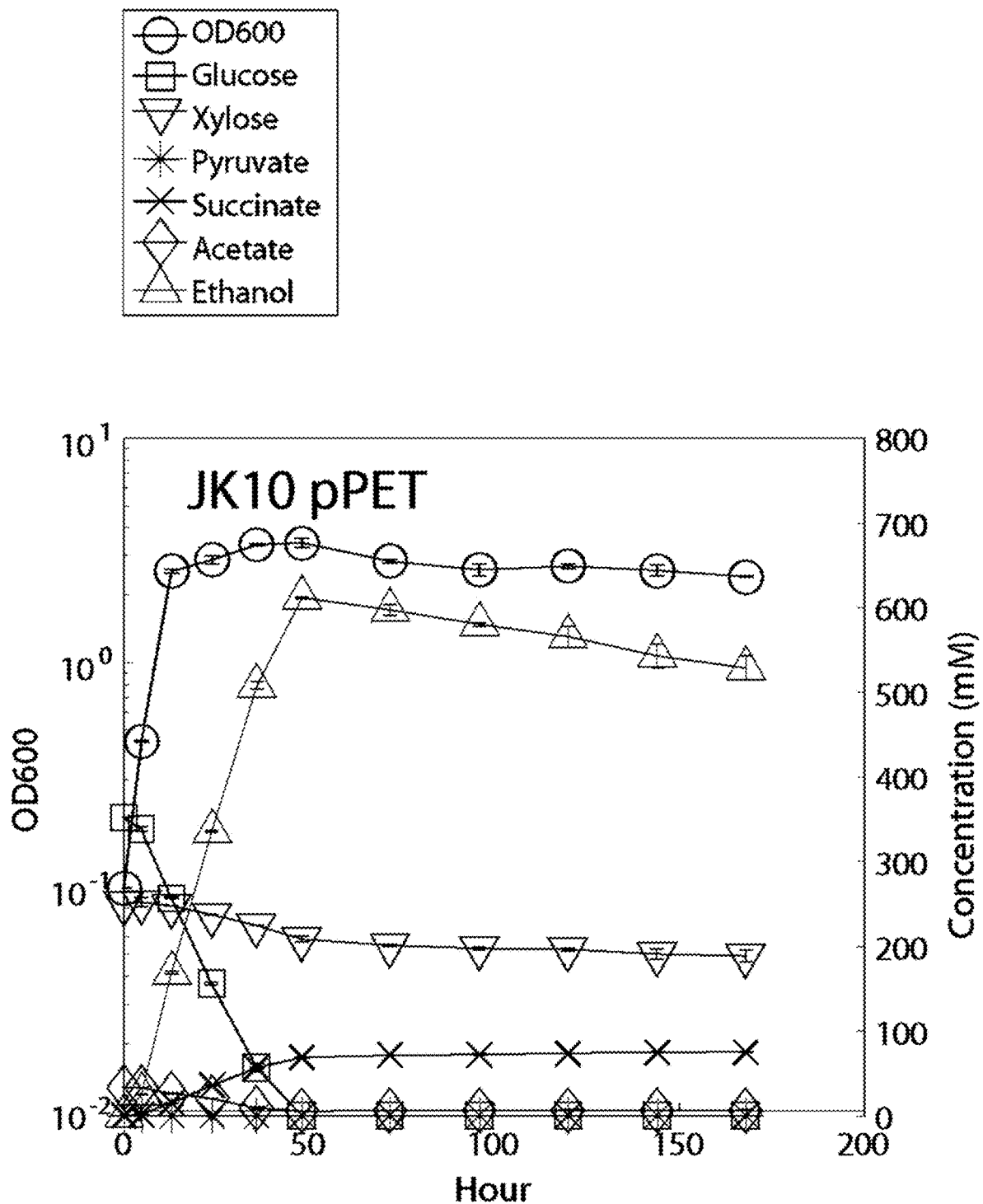
Figure 3F:
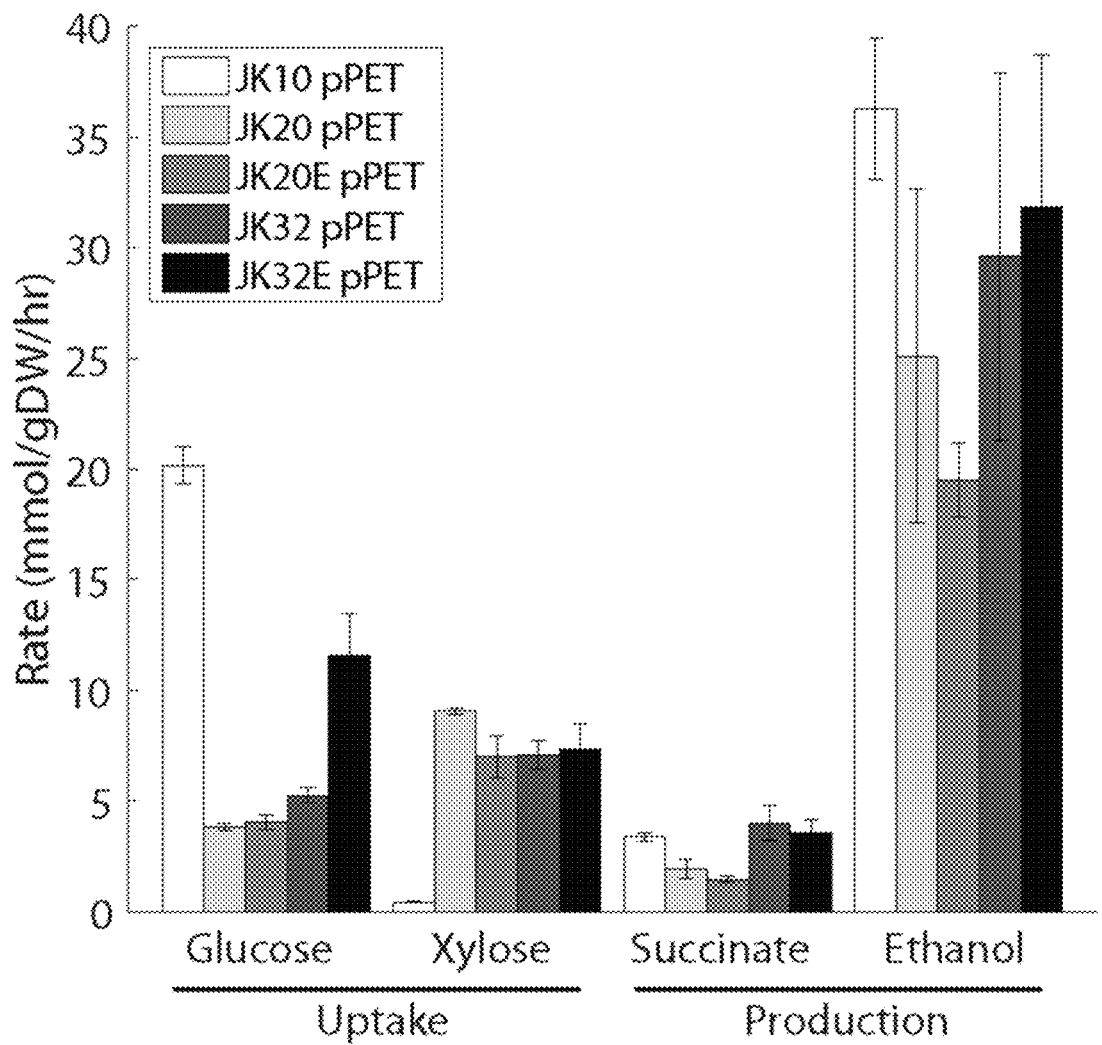
FIG. 3F shows glucose and xylose uptake rates and succinate and ethanol production rates for microorganisms of the invention.

We grew the initial and evolved strains in shake flasks containing a synthetic hydrolysate medium without known inhibitors from pretreatment (SynH) to evaluate their ability to convert high concentration of glucose and xylose to ethanol. An additional copy of PET cassette on a plasmid (pPET) was inserted into the initial strains and single isolates from the evolved strains to further increase the conversion of pyruvate to ethanol. Both the initial and evolved strains simultaneously consumed glucose and xylose and produced ethanol. While JK20E pPET did not show significant improvements over JK20 pPET (FIGS. 3A and 3B), we found that JK32E pPET had 2-fold increase in glucose uptake and improved ethanol production when compared to JK32 pPET (FIGS. 3C and 3D). The control strain JK10 pPET rapidly consumed glucose first and did not utilize much xylose after the glucose was depleted (FIG. 3E). We found that JK32E pPET also produced significant amount of succinate in addition to ethanol (FIG. 3D), and constructed a new strain JK33 pPET by deleting frdA gene from JK32E to remove succinate production. A summary of glucose and xylose uptake rates and succinate and ethanol production rates for each of JK10 pPET, JK20 pPET, JK20E pPET, JK32 pPET, and JK32E pPET is shown in FIG. 3F.

Fermentation in Synthetic and AFEX-Treated Hydrolysate Media

Figure 4A:
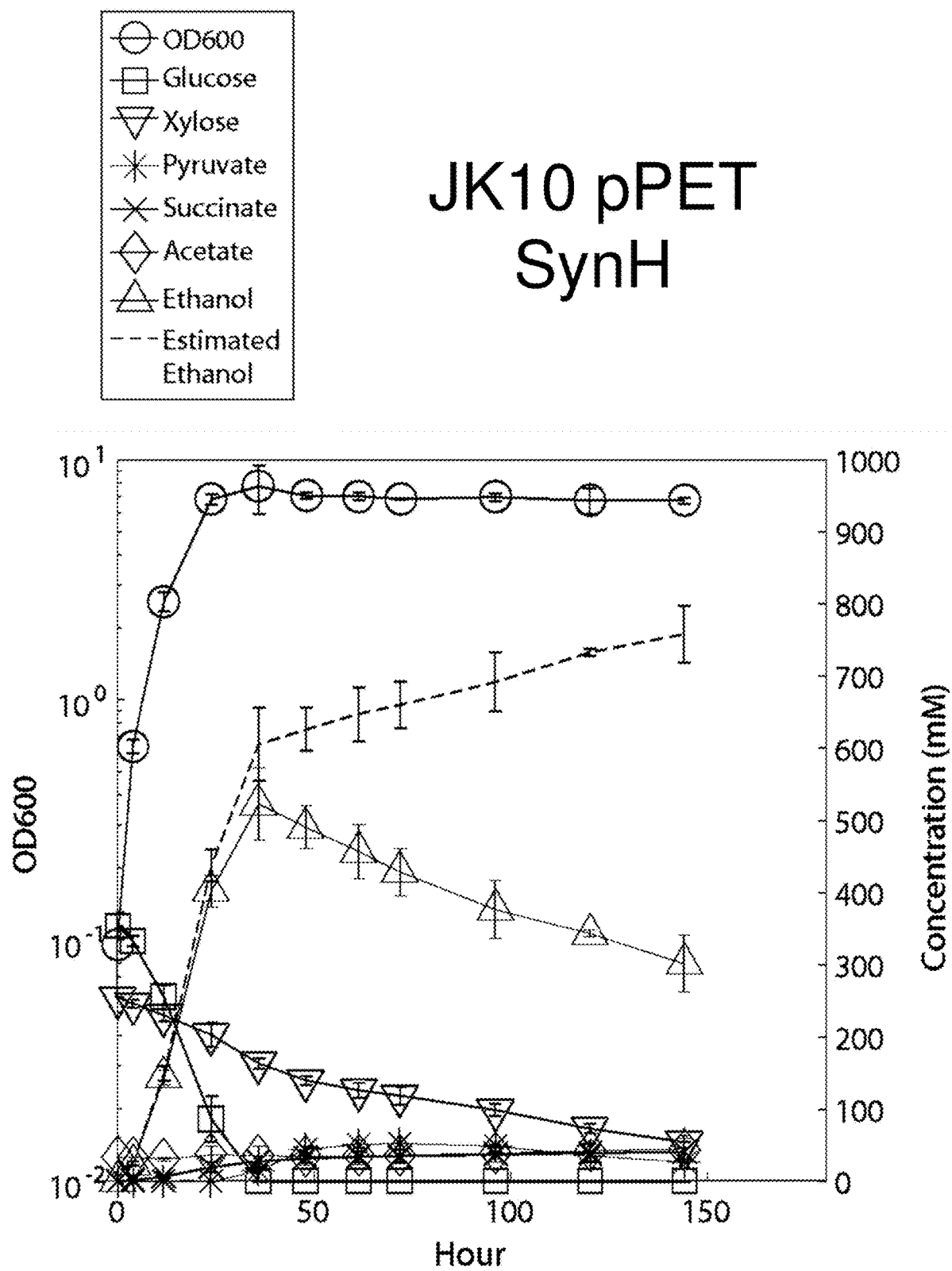
FIGS. 4A-4I show growth (OD600) and compound concentrations versus time for microorganisms of the invention cultured anaerobically in a bioreactor with a synthetic hydrolysate medium (SynH) (FIGS. 4A-4C), ammonia fiber explosion (AFEX)-pretreated corn stover hydrolysate (ACSH) (FIGS. 4D-4F), or AFEX-pretreated switchgrass hydrolysate (ASGH) (FIGS. 4G-4I).
Figure 4B:
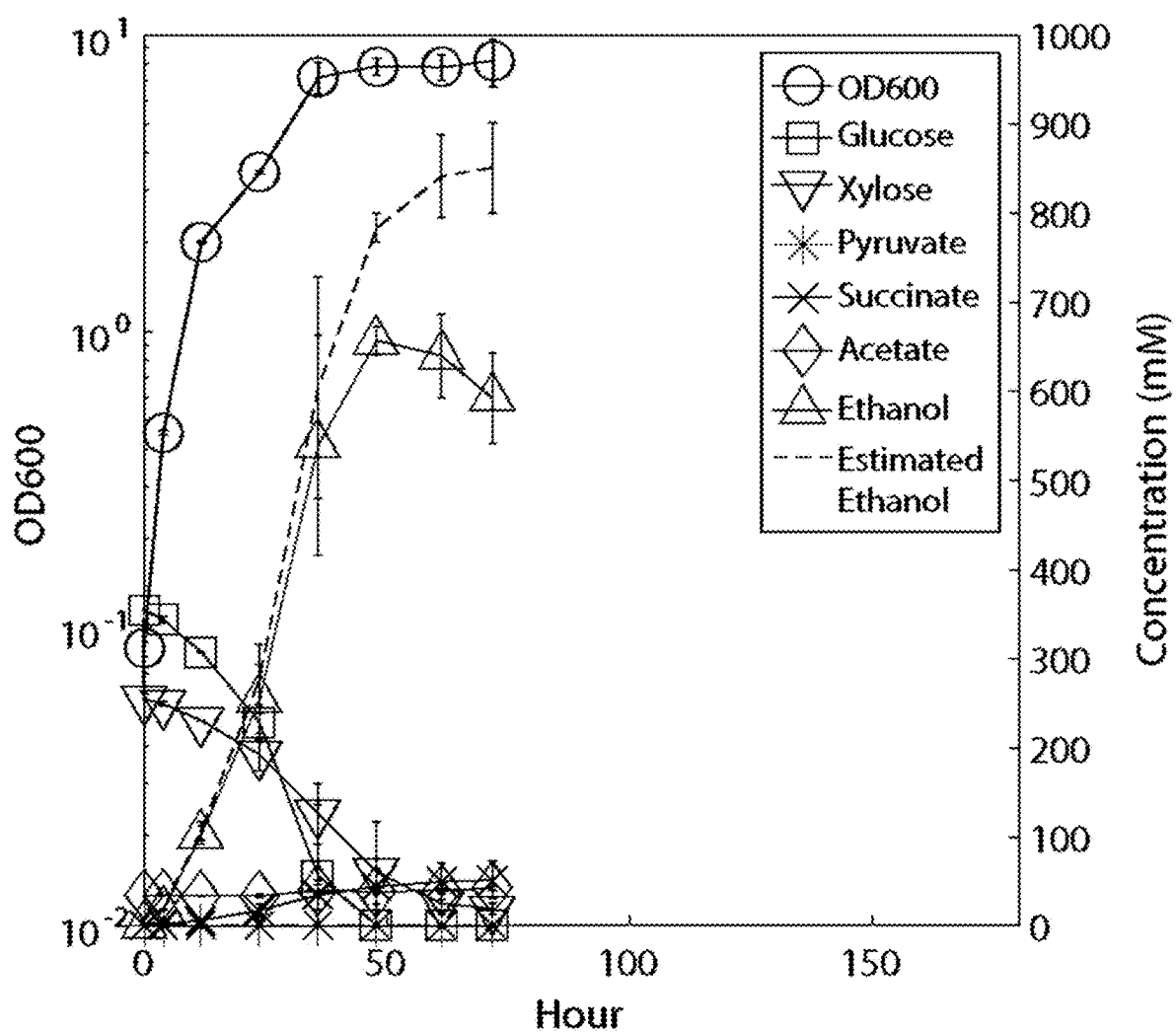
Figure 4C:
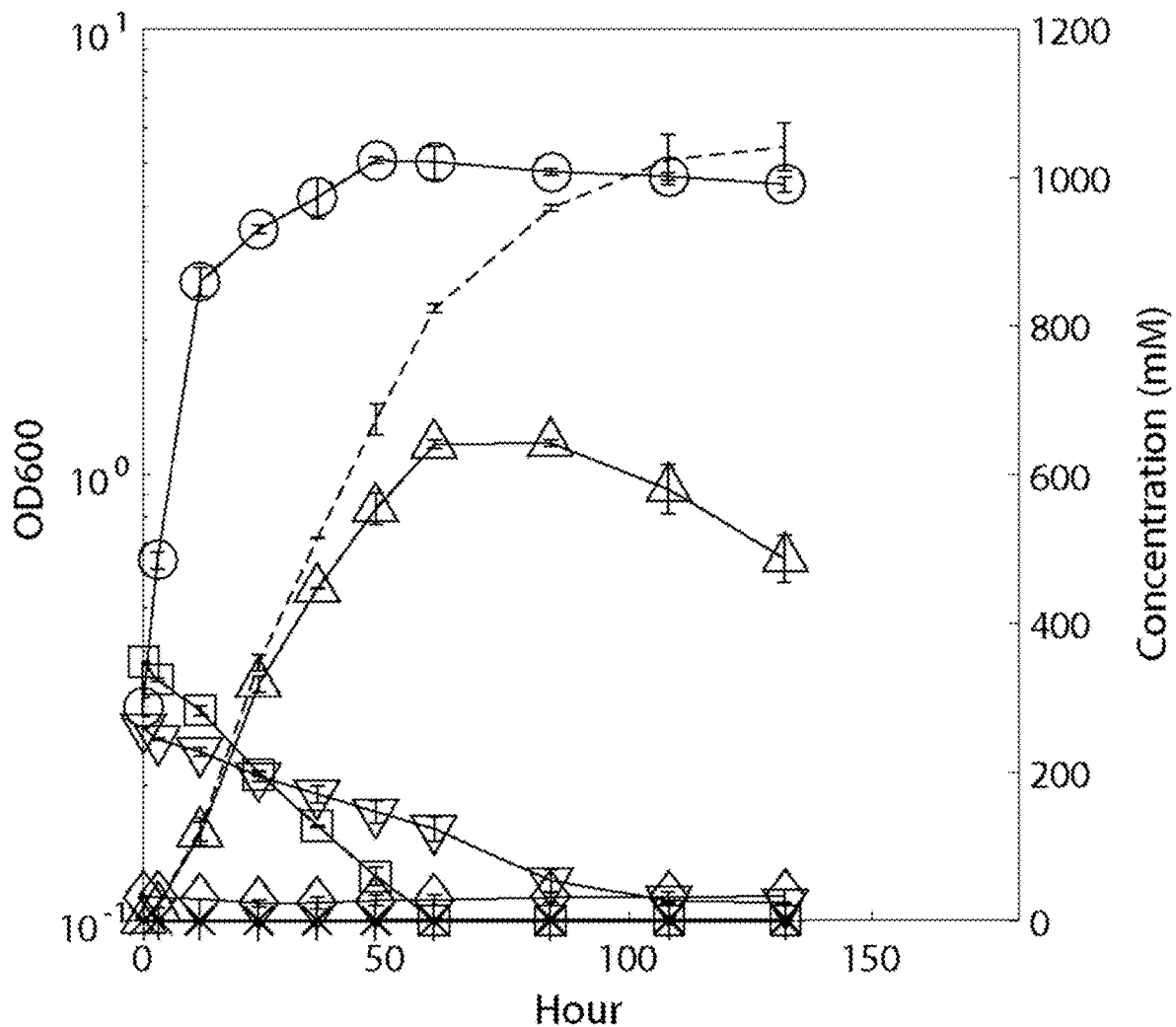

The control strain JK10 pPET and the evolved strains JK32E pPET and JK33 pPET were grown in bioreactors with 100 ml working volumes to demonstrate the evolved strain's ability to co-utilize glucose and xylose in industrially relevant conditions. When grown in SynH using bioreactors, JK10 pPET reached a higher cell density (OD600~7) in 24 hours (compared to shake flasks, FIG. 3E), consumed all glucose within 36 hours, and slowly consumed xylose afterwards (FIG. 4A). JK32E pPET also reached a high cell density (OD600~7) in 36 hours, consumed all glucose within 48 hours, and consumed 92.5% of xylose within 72 hours (FIG. 4B). JK33 pPET reached slightly lower cell density (OD600~5) in 48 hours, consumed all glucose within 60 hours, and consumed 90.6% of xylose within 132 hours (FIG. 4C). Since the evaporation of ethanol from bioreactors due to sparging was significant, we estimated the amount of ethanol lost via evaporation using a simple mass transfer model. The amount lost was added to the measured ethanol titers yielding an estimated ethanol concentration (represented by dotted lines in FIGS. 4A-4I).

Figure 4D:
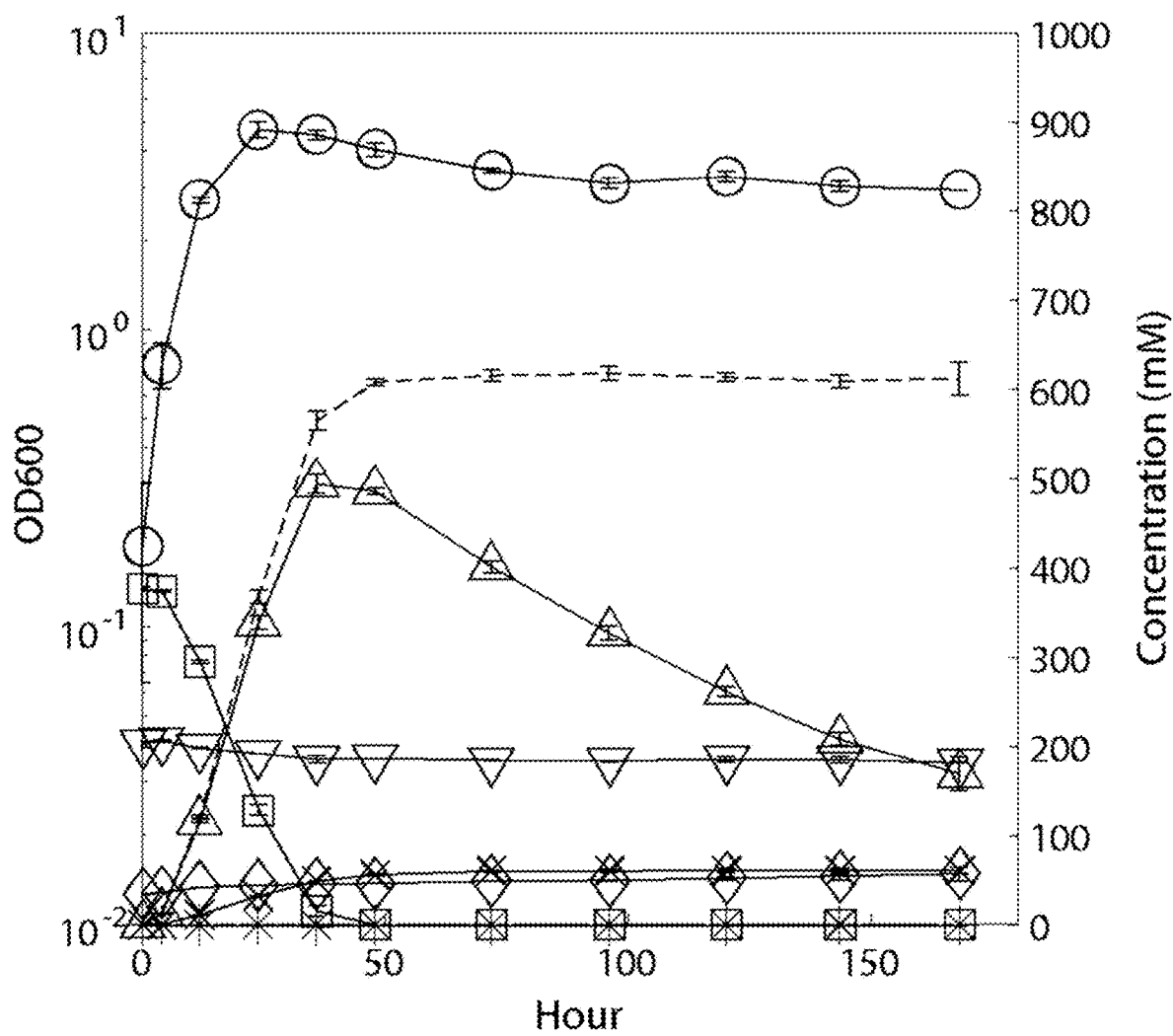
Figure 4E:
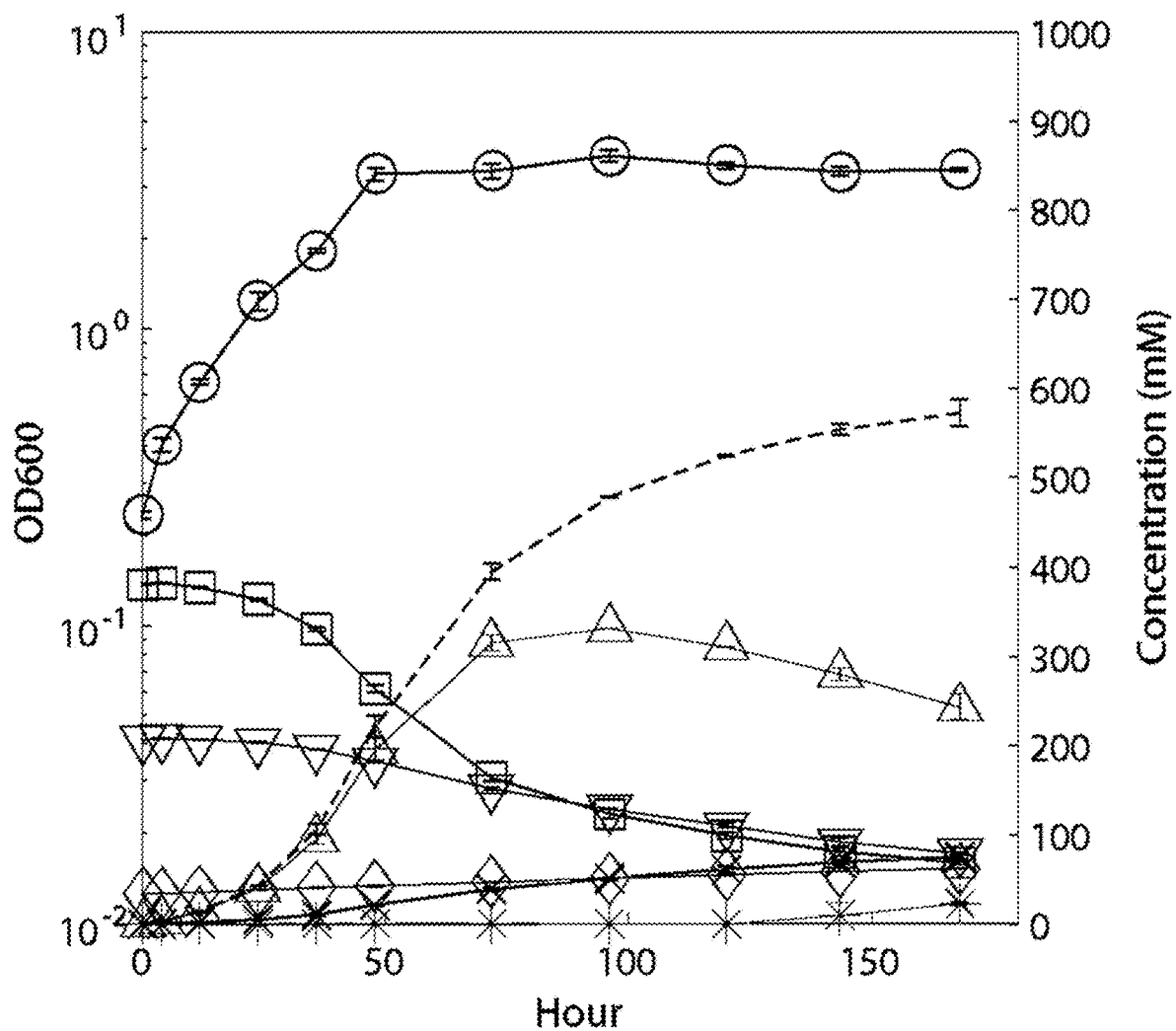
Figure 4F:
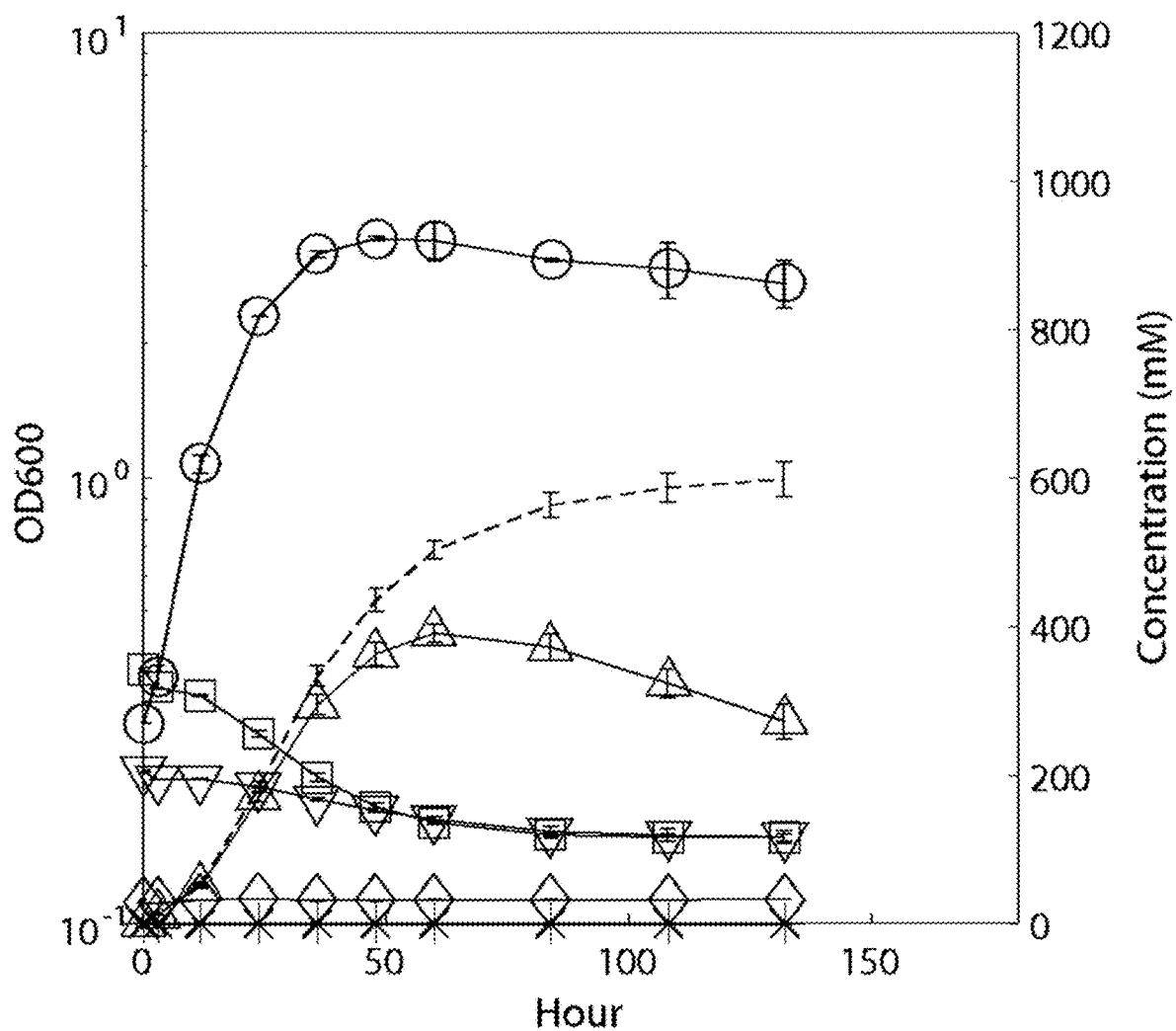
Figure 4G:
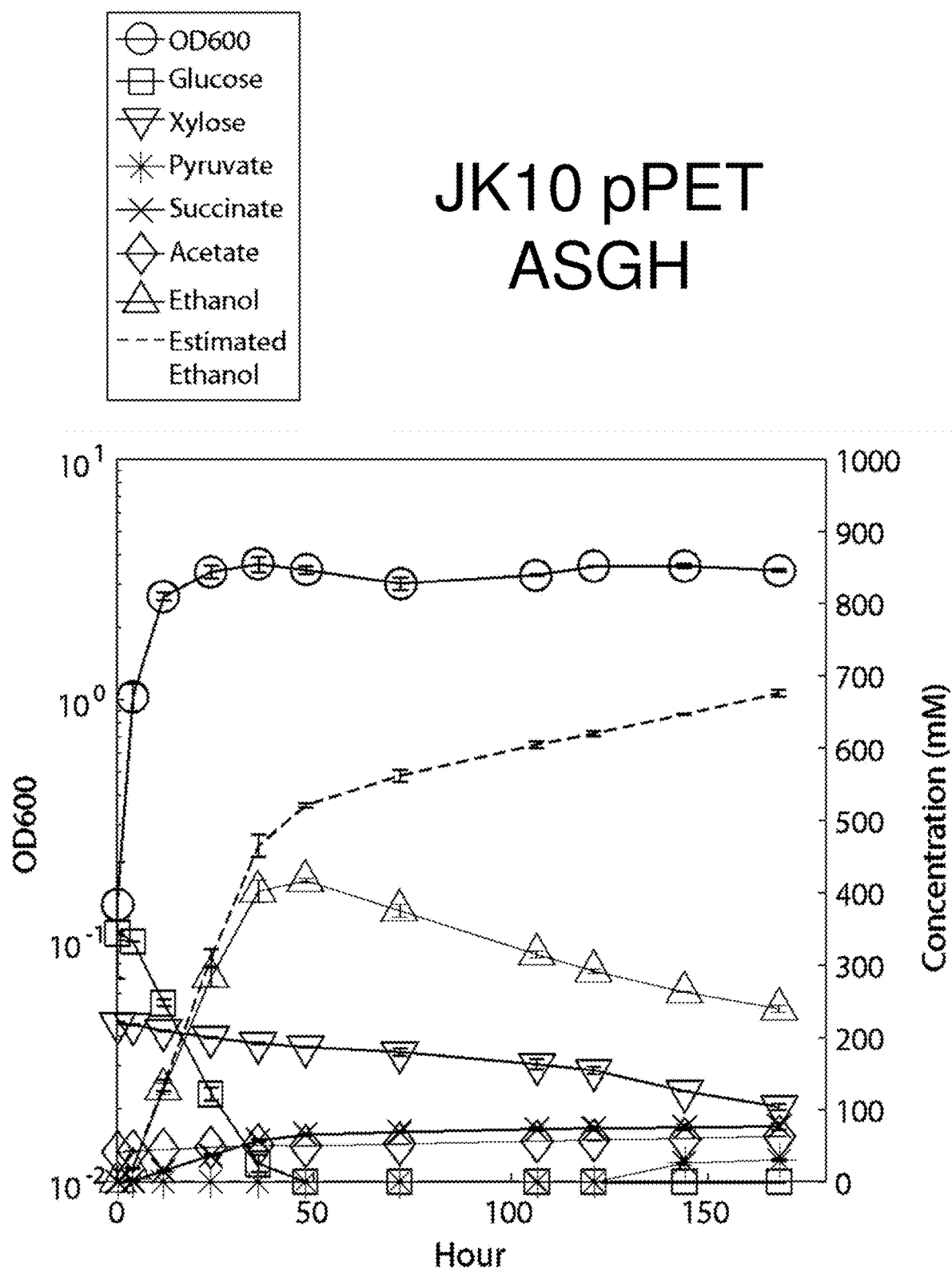
Figure 4H:
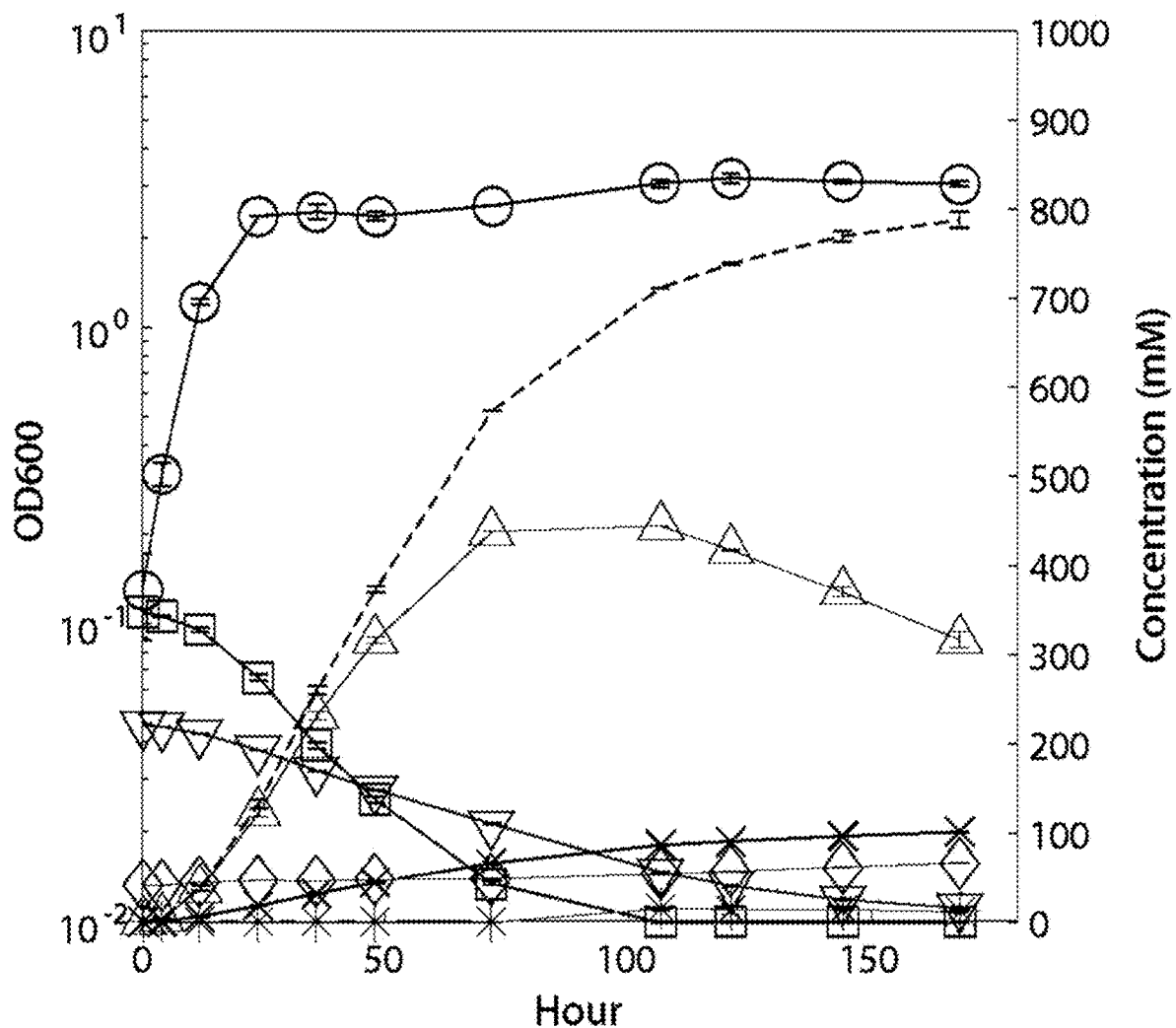
Figure 4I:
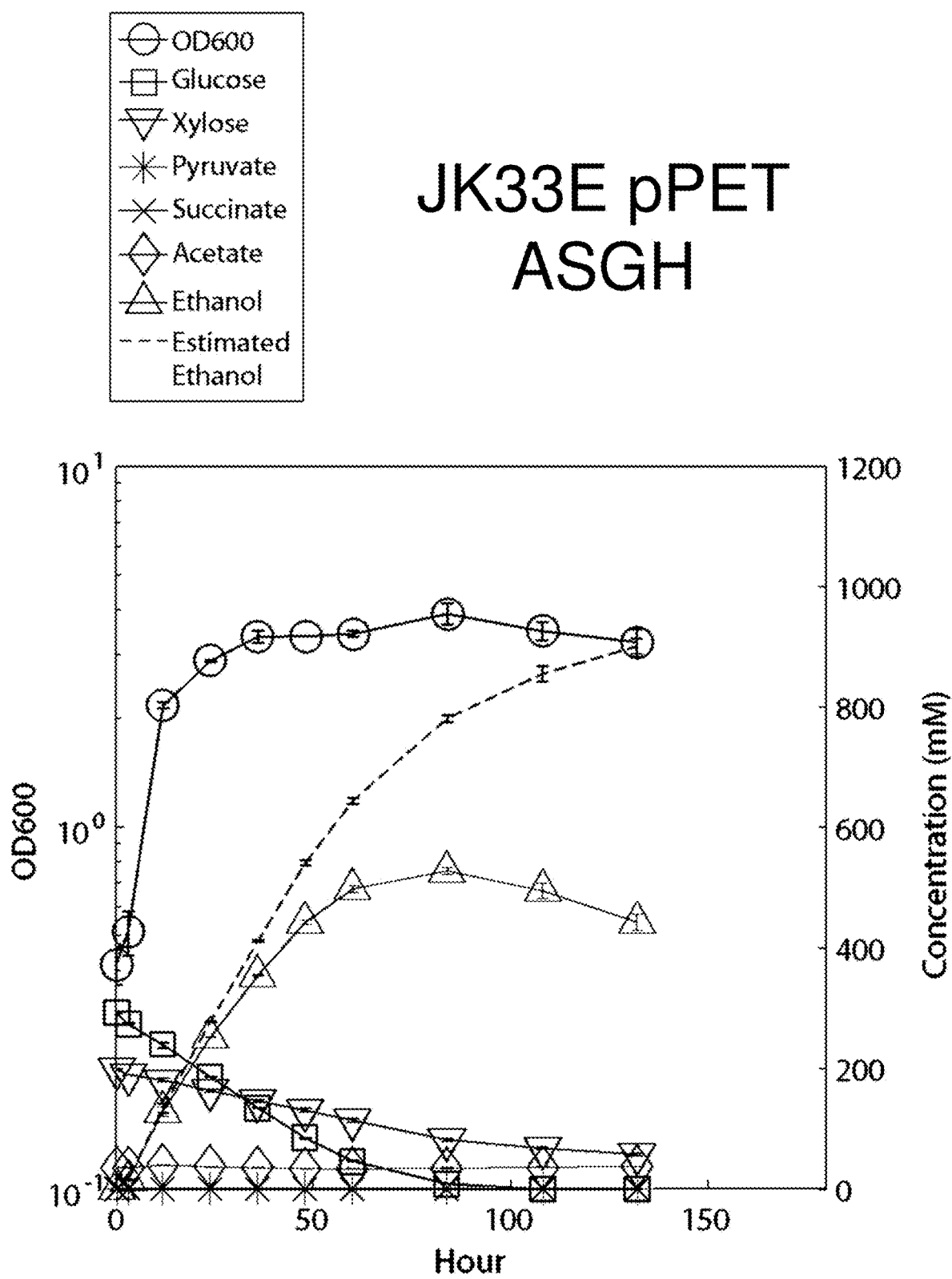

The growth rate and cell density were lower in AFEX-pretreated corn stover and switchgrass hydrolysates (ACSH and ASGH) than in SynH due to the presence of inhibitory compounds from the pretreatment. In ACSH, JK10 pPET was able to utilize glucose within 48 hours, but did not utilize xylose after glucose was depleted (FIG. 4D). JK32E pPET and JK33 pPET were able to co-utilize glucose and xylose, but the conversion slowed down after cells entered stationary phase, likely due to the additional stress caused by lignotoxins and/or accumulated ethanol (FIGS. 4E and 4F). The apparent stress from the pretreatment seemed less significant in ASGH than ACSH. JK10 pPET consumed all glucose and slowly utilized xylose in this medium (FIG. 4G). JK32E pPET and JK33 pPET were able to utilize all glucose and 93% and 71% of xylose, respectively (FIGS. 4H and 4I). The observed ethanol concentration was the highest for the JK33 pPET grown in ASGH among the all strains grown in ACSH or ASGH (Table 3). The estimated amount of ethanol produced by JK33 pPET in ASGH was 900.4 mM (41.5 g/L) which is 109.8% of the theoretical yield based on the consumed glucose and xylose, which could be explained by the other sugars consumed in ACSH and ASGH (e.g., arabinose, fructose, and galactose).

TABLE 3

Sugar consumption and ethanol production in hydrolysate media

| Media Strains | Consumed (mM) | | | Produced (mM) | | Yield (%) |
| --- | --- | --- | --- | --- | --- | --- |
| | Glucose | Xylose | Pyruvate | Succinate | Ethanol (Estimated) | Ethanol (Estimated) |
| SynH | | | | | | |
| JK10 pPET | 353.3 | 199.3 | 27.4 | 41.0 | 522.4 (758.0) | 60.9 (72.9) |
| JK32E pPET | 354.3 | 235.2 | 0.0 | 51.4 | 670.2 (850.3) | 61.6 (77.3) |
| JK33 pPET | 348.5 | 235.1 | 0.0 | 1.7 | 645.2 (1040.9) | 65.8 (95.6) |
| ACSH | | | | | | |
| JK10 pPET | 375.9 | 21.5 | 0.0 | 60.2 | 494.1 (611.8) | 64.4 (78.7) |
| JK32E pPET | 311.1 | 126.3 | 23.3 | 74.3 | 330.6 (572.2) | 51.5 (68.7) |
| JK33 pPET | 225.0 | 88.0 | 0.0 | 0.5 | 390.0 (597.5) | 75.2 (100.1) |
| ASGH | | | | | | |
| JK10 pPET | 344.8 | 116.5 | 31.0 | 76.0 | 415.9 (675.6) | 55.8 (76.4) |
| JK32E pPET | 347.7 | 205.7 | 11.5 | 100.7 | 443.7 (787.5) | 45.7 (75.8) |
| JK33 pPET | 292.3 | 141.0 | 0.0 | 0.1 | 526.8 (900.4) | 69.2 (109.8) |

REFERENCES

Alpert, C. A., M. Dörschug, D. Saffen, R. Frank, J. Deutscher, and W. Hengstenberg. 1985. The bacterial phosphoenolpyruvate-dependent phosphotransferase system. Isolation of active site peptides by reversed-phase high performance liquid chromatography and determination of their primary structure. *J. Chromatogr.* 326:363-371.

Alpert, C.-A., R. Frank, K. Stüber, J. Deutscher, and W. Hengstenberg. 1985. Phosphoenolpyruvate-dependent protein kinase Enzyme I of *Streptococcus faecalis*. Purification and properties of the enzyme and characterization of its active center. *Biochemistry* 24:959-964.

Anderson, B., N. Weigel, W. Kundig, and S. Roseman. 1971. Sugar transport. III. Purification and properties of a phosphocarrier protein of the phosphoenolpyruvate-dependent phosphotransferase system of *Escherichia coli*. *J. Biol. Chem.* 246:7023-7033.

Baba, T., T. Ara, M. Hasegawa, Y. Takai, Y. Okumura, M. Baba, K. A. Datsenko, M. Tomita, B. L. Wanner, and H. Mori. Construction of *Escherichia coli* K-12 in-frame, single-gene knockout mutants: the Keio collection. *Mol Syst Biol*, 2006. 2: p. 2006 0008.

Balderas-Hernández V E, Hernández-Montalvo V, Bolívar F, Gosset G, Martínez A. Adaptive evolution of *Escherichia coli* inactivated in the phosphotransferase system operon improves co-utilization of xylose and glucose under anaerobic conditions. *Appl Biochem Biotechnol.* 2011 February; 163(4):485-96.

Barua, D., J. Kim, and J. L. Reed. An automated phenotype-driven approach (GeneForce) for refining metabolic and regulatory models. *PLoS Comput Biol*, 2010. 6(10): p. e1000970.

Beneski, D. A., A. Nakazawa, N. Weigel, P. E. Hartman, and S. Roseman. 1982. Sugar transport by the bacterial phosphotransferase system. Isolation and characterization of a phosphocarrier protein HPr from wild type and mutants of *Salmonella typhimurium*. J. Biol. Chem. 257:14492-14498.

Beyreuther, K., H. Raufuss, O. Schrecker, and W. Hengstenberg. 1977. The phosphoenolpyruvate-dependent phosphotransferase system of *Staphylococcus aureus*. 1. Aminoacid sequence of the phosphocarrier protein HPr. *Eur. J. Biochem.* 75:275-286.

Binder J B, Raines R T. Fermentable sugars by chemical hydrolysis of biomass. *Proc Natl Acad Sci USA.* 2010 Mar. 9; 107(10):4516-21.

Blatch, G. L., R. R. Scholle, and D. R. Woods. 1990. Nucleotide sequence and analysis of the *Vibrio alginolyticus* sucrose uptake-encoding region. Gene 95:17-23.

Boos, W., U. Ehmann, H. Forki, W. Klein, M. Rimmele, and P. W. Postma. 1990. Trehalose transport and metabolism in *Escherichia coli*. *J. Bacteriol.* 172:3450-3461.

Bramley, H. F., and H. L. Kornberg. 1987. Sequence homologies between proteins of bacterial phosphoenolpyruvate-dependent sugar phosphotransferase systems: identification of possible phosphate-carrying histidine residues. *Proc. Natl. Acad. Sci. USA* 84:4777-4780.

Byrne, C. R., R. S. Monroe, K. A. Ward, and N. M. Kredich. 1988. DNA sequences of the cysK regions of *Salmonella typhimurium* and *Escherichia coli* and linkage of the cysK regions to ptsH. *J. Bacteriol.* 170:3150-3157

Covert, M. W., E. M. Knight, J. L. Reed, M. J. Herrgard, and B. O. Palsson. Integrating high-throughput and computational data elucidates bacterial networks. *Nature*, 2004. 429(6987): p. 92-6.

da Costa Lopes A M, Joao K G, Morais A R C, Bogel-Lukasik E, Bogel-Lukasik R. Ionic Liquids as a tool for lignocellulosic biomass fractionation. *Sustainable Chemical Processes,* 2013. 1(3):1-31.

Datsenko K A, Wanner B L. One-step inactivation of chromosomal genes in *Escherichia coli* K-12 using PCR products. *Proc Natl Acad Sci USA.* 2000 Jun. 6; 97(12): 6640-5.

De Reuse, H., and A. Danchin. 1988. The ptsH, ptsI, and crr genes of the *Escherichia coli* phosphoenolpyruvate-dependent phosphotransferase system: a complex operon with several modes of transcription. *J. Bacteriol.* 170: 3827-3837.

Deutscher, J., B. Pevec, K. Beyreuther, H.-H. Klitz, and W. Hengstenberg. 1986. Streptococcal phosphoenolpyruvatesugar phosphotransferase system: amino acid sequence and site of ATP-dependent phosphorylation of HPr. *Biochemistry* 25:6543-6551.

Dooijewaard, G., F. F. Roossien, and G. T. Robillard. 1979. *Escherichia coli* phosphoenolpyruvate dependent phosphotransferase system. Copurification of HPr and $\alpha$1-6 glucan. *Biochemistry* 18:2990-2996.

Ebner, R., and J. W. Lengeler. 1988. DNA sequence of the gene serA encoding the sucrose transport protein Enzyme-$II^{Ser}$ of the phosphotransferase system from enteric bacteria: homology of the Enzyme $II^{Ser}$ and Enzyme $II^{Bgl}$ proteins. *Mol. Microbiol.* 2:9-17.

Eisermann, R., R. Fischer, U. Kessler, A. Neubauer, and W. Hengstenberg. 1991. Staphylococcal phosphoenolpyruvate-dependent phosphotransferase system. Purification and protein sequencing of the *Staphylococcus camosus* histidine-containing protein, and cloning and DNA sequencing of the ptsH gene. *Eur. J. Biochem.* 197:9-14.

El Hassouni, M., B. Henrissat, M. Chippaux, and F. Barras. 1992. Nucleotide sequence of the arb genes, which control β-glucoside utilization in *Erwinia chrysanthemi*: comparison with the *Escherichia coli* bgl operon and evidence for a new β-glycohydrolase family including enzymes from eubacteria, archaebacteria, and humans. J. Bacteriol. 174:765-777.

Erni, B., and B. Zanolari. 1986. Glucose permease of the bacterial phosphotransferase system. Gene cloning, overproduction, and amino acid sequence of enzyme $II^{Glc}$, *J. Biol. Chem.* 261:16398-16403.

Feist, A. M., C. S. Henry, J. L. Reed, M. Krummenacker, A. R. Joyce, P. D. Karp, L. J. Broadbelt, V. Hatzimanikatis, and B. O. Palsson. A genome-scale metabolic reconstruction for *Escherichia coli* K-12 MG1655 that accounts for 1260 ORFs and thermodynamic information. *Mol Syst Biol*, 2007. 3: p. 121.

Feldheim D A, Chin A M, Nierva C T, Feucht B U, Cao Y W, Xu Y F, Sutrina S L, Saier M H Jr. Physiological consequences of the complete loss of phosphoryl-transfer proteins HPr and FPr of the phosphoenolpyruvate:sugar phosphotransferase system and analysis of fructose (fru) operon expression in *Salmonella typhimurium*. *J Bacteriol.* 1990 September; 172(9):5459-69.

Fouet, A., M. Arnaud, A. Klier, and G. Rapoport. 1987. *Bacillus subtilis* sucrose-specific enzyme II of the phosphotransferase system: expression in *Escherichia coli* and homology to enzymes II from enteric bacteria. *Proc. Natl. Acad. Sci. USA* 84:8773-8777.

Gagnon, G., C. Vadeboncoeur, R. C. Levesque, and M. Frenette. 1992. Cloning, sequencing, and expression in *Escherichia coli* of the ptsI gene encoding enzyme I of the phosphoenolpyruvate:sugar phosphotransferase transport system from *Streptococcus salivarius*. Gene 121:71-78.

Gardner J G, Keating D H. 2010. Requirement of the type II secretion system for utilization of cellulosic substrates by *Cellvibrio japonicus*. *Appl. Environ. Microbiol.* 76:5079-5087.

Geerse, R. H., C. R. Ruig, A. R. J. Schuitema, and P. W. Postma. 1986. Relationship between pseudo-HPr and the PEP:fructose phosphotransferase system in *Salmonella typhimurium* and *Escherichia coli*. *Mol. Gen. Genet.* 203:435-444.

Geerse R H, Izzo F, Postma P W. 1989 The PEP:fructose phosphotransferase system in *Salmonella typhimurium*: FPr combines enzyme III$^{Fru}$ and pseudo-HPr activities. *Mol. Gen. Genet.* 216(2-3):517-25.

Gonzy-Tréboul, G., J. H. de Waard, M. Zagorec, and P. W. Postma. 1991. The glucose permease of the phosphotransferase system of *Bacillus subtilis*: evidence for II01c and III01c domains. *Mol. Microbiol.* 5:1241-1249.

Gonzy-Tréboul, G., M. Zagorec, M.-C. Rain-Guion, and M. Steinmetz. 1989. Phosphoenolpyruvate:sugar phosphotransferase system of *Bacillus subtilis*: nucleotide sequence of ptsX, ptsH, and the 5'-end of ptsI and evidence for a ptsHI operon. *Mol. Microbiol.* 3:103-112.

Hall, B. G., and L. Xu. 1992. Nucleotide sequence, function, activation, and evolution of the cryptic asc operon of *Escherichia coli* K12. Mol. Biol. Evol. 9:688-706.

Hengstenberg, W., O. Schrecker, R. Stein, and R. Weil. 1976. Lactose transport and metabolism in *Staphylococcus aureus*. Zentralbl. *Bakteriol. Parasitenkd. Infektionskr. Hyg. Sect. I* 5:203-219

Jaffor Ullah, A. H., and V. P. Cirillo. 1977. Mycoplasma phosphoenolpyruvate-dependent sugar phosphotransferase system: purification and characterization of enzyme I. *J. Bacteriol.* 131:988-996.

Jaffor Ullah, A. H., and V. P. Cirillo. 1976. Mycoplasma phosphoenolpyruvate-dependent sugar phosphotransferase system: purification and characterization of the phosphocarrier protein. *J. Bacteriol.* 127:1298-1306.

Jenkinson, H. F. 1989. Properties of a phosphocarrier protein (HPr) extracted from intact cells of *Streptococcus sanguis*. *J. Gen. Microbiol.* 135:3183-3197.

Kalbitzer, H. R., W. Hengstenberg, P. Rösch, P. Muss, P. Bernsmann, R. Engelmann, M. Dörschug, and J. Deutscher. 1982. HPr proteins of different microorganisms studied by hydrogen-1 high resolution nuclear magnetic resonance: similarities of structures and mechanisms. *Biochemistry* 21:2879-2885.

Keating, D. H., Y. Zhang, I. M. Ong, S. McIlwain, E. H. Morales, J. A. Grass, M. Tremaine, W. Bothfeld, A. Higbee, A. Ulbrich, et al. Aromatic inhibitors derived from ammonia-pretreated lignocellulose hinder bacterial ethanologenesis by activating regulatory circuits controlling inhibitor efflux and detoxification. *Front Microbiol,* 2014. 5: p. 402.

Kim, J. and J. L. Reed. OptORF: Optimal metabolic and regulatory perturbations for metabolic engineering of microbial strains. *BMC Syst Biol,* 2010. 4: p. 53.

Kim, J. and J. L. Reed: RELATCH: relative optimality in metabolic networks explains robust metabolic and regulatory responses to perturbations. *Genome Biol,* 2012. 13(9): p. R78.

Kohlbrecher, D., R. Eisermann, and W. Hengstenberg. 1992. Staphylococcal phosphoenolpyruvate-dependent phospho-transferase system: molecular cloning and nucleotide sequence of the *Staphylococcus carnosus* ptsI gene and expression and complementation studies of the gene product. *J. Bacteriol.* 174:2208-2214.

Lengeler, J. W., J. Bockmann, H. Heuel, and F. Titgemeyer. 1992. The Enzymes II of the PTS as carbohydrate transport systems: what the evolutionary studies tell us on their structure and function, p. 77-85. In E. Quagliariello and F. Palmieri (ed.), Molecular mechanisms of transport. Elsevier Biomedical Press, Amsterdam.

LiCalsi, C., T. S. Crocenzi, E. Freire, and S. Roseman. 1991. Sugar transport by the bacterial phosphotransferase system. Structural and thermodynamic domains of Enzyme I of *Salmonella typhimurium*. *J. Biol. Chem.* 266:19519-19527.

Lopez-de Los Santos Y, Chan H, Cantu V A, Rettner R, Sanchez F, Zhang Z, Saier M H Jr, Soberon X. Genetic engineering of the phosphocarrier protein NPr of the *Escherichia coli* phosphotransferase system selectively improves sugar uptake activity. *J Biol Chem.* 2012 Aug. 24; 287(35):29931-9.

Marquet, M., M.-C. Creignou, and R. Dedonder. 1976. The phosphoenolpyruvate:methyl-a-n-glucoside phosphotransferase system in *Bacillus subtilis* Marburg 168: purification and identification of the phosphocarrier protein (HPr). *Biochimie* 58:435-441.

Mimura, C. S., L. B. Eisenberg, and G. R. Jacobson. 1984. Resolution of the phosphotransferase enzymes of *Streptococcus mutans*: purification and preliminary characterization of a heat-stable phosphocarrier protein. *Infect. Immun.* 44:708-715.

Nelson, S. O., A. R. J. Schuitema, R. Benne, L. H. T. Vander Ploeg, J. S. Plijter, F. Aan, and P. W. Postma. 1984. Molecular cloning, sequencing, and expression of the crr gene: the structural gene for III$^{Glc}$ of the bacterial PEP:glucose phosphotransferase system. *EMBO J.* 3:1587-1593.

Orth, J. D., T. M. Conrad, J. Na, J. A. Lerman, H. Nam, A. M. Feist, and B. O. Palsson. A comprehensive genome-scale reconstruction of *Escherichia coli* metabolism—2011. *Mol Syst Biol,* 2011. 7: p. 535.

Peri, K. G., H. Goldie, and E. B. Waygood. 1990. Cloning and characterization of the N-acetylglucosamine operon of *Escherichia coli*. Biochem. Cell Biol. 68:123-137

Peri, K. G., and E. B. Waygood. 1988. Sequence of cloned Enzyme II$^{N-acetylglucosamine}$ of the phosphoenolpyruvate:Nacetylglucosamine phosphotransferase system of *Escherichia coli*. *Biochemistry* 27:6054-6061.

Postma P W, Lengeler J W, Jacobson G R. Phosphoenolpyruvate:carbohydrate phosphotransferase systems of bacteria. *Microbiol Rev.* 1993 September; 57(3):543-94.

Powers, D. A., and S. Roseman. 1984. The primary structure of the *Salmonella typhimurium* HPr, a phosphocarrier protein of the phosphoenolpyruvate:glycose phosphotransferase system. A correction. *J. Biol. Chem.* 259:15212-15214.

Reed, J. L., T. D. Vo, C. H. Schilling, and B. O. Palsson. An expanded genome-scale model of *Escherichia coli* K-12 (iJR904 GSM/GPR). *Genome Biol,* 2003. 4(9): p. R54.

Reidl, J., and W. Boos. 1991. The malX malY operon of *Escherichia coli* encodes a novel enzyme II of the phosphotransferase system recognizing glucose and maltose and an enzyme abolishing the endogenous induction of the maltose system. *J. Bacteriol.* 173:4862-4876.

Reizer, J., J. Deutscher, and M. H. Saier, Jr. 1989. Metabolitesensitive, ATP-dependent, protein kinase-catalyzed phosphorylation of HPr, a phosphocarrier protein of the phosphotransferase system in Gram-positive bacteria. *Biochimie* 71:989-996.

Reizer, J., S. L. Sutrina, L.-F. Wu, J. Deutscher, P. Reddy, and M. H. Saier, Jr. 1992. Functional interactions between proteins of the phosphoenolpyruvate:sugar phosphotransferase systems of *Bacillus subtilis* and *Escherichia coli*. *J. Biol. Chem.* 267:9158-9169.

Reizer, J., M. H. Saier, J. Deutscher, F. Grenier, J. Thompson, and W. Hengstenberg. 1988. The phosphoenolpyruvate:sugar phosphotransferase system in Gram-positive bacteria: properties, mechanism and regulation. *Crit. Rev. Microbiol.* 15:297-338.

Reizer, J., S. L. Sutrina, M. H. Saier, G. C. Stewart, A. Peterkofsky, and P. Reddy. 1989. Mechanistic and physiological consequences of HPr (ser) phosphorylation on the activities of the phosphoenolpyruvate:sugar phosphotransferase system in Gram-positive bacteria: studies with site-specific mutants of HPr. *EMBO J.* 8:2111-2120.

Robillard, G. T., G. Dooijewaard, and J. Lolkema. 1979. *Escherichia coli* phosphoenolpyruvate dependent phosphotransferase system. Complete purification of Enzyme I by hydrophobic interaction chromatography. *Biochemistry* 18:2984-2989.

Rogers, M. J., T. Ohgi, J. Plumbridge, and D. Söll. 1988. Nucleotide sequences of the *Escherichia coli* nagE and nagB genes: the structural genes for the N-acetylglucosamine transport protein of the bacterial phosphoenolpyruvate:sugar phosphotransferase system and for glucosamine-6-phosphate deaminase. *Gene* 62:197-207.

Saffen, D. W., K. A. Presper, T. L. Doering, and S. Roseman. 1987. Sugar transport by the bacterial phosphotransferase system. Molecular cloning and structural analysis of the *Escherichia coli* ptsH, ptsI, and crr genes. *J. Biol. Chem.* 262:16241-16253.

Saier, M. H., Jr. and T. M. Ramseier. The catabolite repressor/activator (Cra) protein of enteric bacteria. *J Bacteriol*, 1996. 178(12): p. 3411-7.

Sato, Y., F. Poy, G. R. Jacobson, and H. K. Kuramitsu. 1989. Characterization and sequence analysis of the scrA gene encoding enzyme II$^{Scr}$ of the *Streptococcus mutans* phosphoenolpyruvate-dependent sucrose phosphotransferase system. *J. Bacteriol.* 171:263-271.

Schnetz, K., C. Toloczyki, and B. Rak. 1987. β-Glucoside (bgl) operon of *Escherichia coli* K-12: nucleotide sequence, genetic organization, and possible evolutionary relationship to regulatory components of two *Bacillus subtilis* genes. *J. Bacteriol.* 169:2579-2590.

Schnierow, B. J., M. Yamada, and M. H. Saier, Jr. 1989. Partial nucleotide sequence of the pts operon in *Salmonella typhimurium*: comparative analyses in five bacterial genera. *Mol. Microbiol.* 3:113-118.

Schwalbach, M. S., D. H. Keating, M. Tremaine, W. D. Marner, Y. Zhang, W. Bothfeld, A. Higbee, J. A. Grass, C. Cotten, J. L. Reed, et al. Complex physiology and compound stress responses during fermentation of alkali-pretreated corn stover hydrolysate by an *Escherichia coli* ethanologen. *Appl Environ Microbiol*, 2012. 78(9): p. 3442-57.

Simoni, R. D., T. Nakazawa, J. B. Hays, and S. Roseman. 1973. Sugar transport. IV. Isolation and characterization of the lactose phosphotransferase system in *Staphylococcus aureus*. *J. Biol. Chem.* 248:932-940.

Sutrina, S. L., J. Reizer, and M. H. Saier, Jr. 1988. Inducer expulsion in *Streptococcus pyogenes*: properties and mechanism of the efflux reaction. *J. Bacteriol.* 170:1874-1877.

Tchieu J H, Norris V, Edwards J S, Saier M H Jr. The complete phosphotransferase system in *Escherichia coli*. *J Mol Microbiol Biotechnol.* 2001 July; 3(3):329-46.

Thibault, L., and C. Vadeboncoeur. 1985. Phosphoenolpyruvate-sugar phosphotransferase transport system of *Streptococcus mutans*: purification of HPr and enzyme I and determination of their intracellular concentrations by rocket immunoelectrophoresis. *Infect. Immun.* 50:817-825.

Titgemeyer, F., R. Eisermann, W. Hengstenberg, and J. W. Lengeler. 1990. The nucleotide sequence of ptsH gene from *Klebsiella pneumoniae*. *Nucleic Acids Res.* 18:1898.

Vadeboncoeur, C., M. Proulx, and L. Trahan. 1983. Purification of proteins similar to HPr and enzyme I from the oral bacterium *Streptococcus salivarius*. Biochemical and immunochemical properties. *Can. J. Microbiol.* 29:1694-1705.

Vogler, A. P., and J. W. Lengeler. 1991. Comparison of the sequences of the nagE operons from *Klebsiella pneumonia* and *Escherichia coli* K12: enhanced variability of the enzyme II$^{N-acetylglucosamine}$ in regions connecting functional domains. *Mol. Gen. Genet.* 230:270-276.

Waygood, E. B., and T. Steeves. 1980. Enzyme I of the phosphoenolpyruvate:sugar phosphotransferase system of *Escherichia coli*. Purification to homogeneity and some properties. *Can. J. Biochem.* 58:40-48.

Waygood, E. B. 1980. Resolution of the phosphoenolpyruvate:fructose phosphotransferase system of *Escherichia coli* into two components: enzyme utructose and fructose-induced HPrlike protein (FPr). *Can. J. Biochem.* 58:1144-1146.

Waygood, E. B., R. L. Mattoo, E. Erickson, and C. Vadeboncoeur. 1986. Phosphoproteins and the phosphoenolpyruvate:sugar phosphotransferase system of *Streptococcus salivarius*. Detection of two different ATP-dependent phosphorylations of the phosphocarrier protein HPr. *Can. J. Microbiol.* 32:310-318.

Weigel, N., D. A. Powers, and S. Roseman. 1982. Sugar transport by the bacterial phosphotransferase system. Primary structure and active site of a general phosphocarrier protein (HPr) from *Salmonella typhimurium*. *J. Biol. Chem.* 257:14499-14509.

Weigel, N., E. B. Waygood, M. A. Kukunazinska, A. Nakazawa, and S. Roseman. 1982. Sugar transport by the bacterial phosphotransferase system. Isolation and characterization of Enzyme I from *Salmonella typhimurium*. *J. Biol. Chem.* 257: 14461-14469.

Zagorec, M., and P. W. Postma. 1992. Cloning and nucleotide sequence of the ptsG gene of *Bacillus subtilis*. *Mol. Gen. Genet.* 234:325-328.

Zukowski, M. M., L. Miller, P. CosgweU, K. Chen, S. Aymerich, and M. Steinmetz. 1990. Nucleotide sequence of the sacS locus of *Bacillus subtilis* reveals the presence of two regulatory genes. *Gene* 90:153-155.

We claim:

1. A recombinant microorganism comprising:
   a genetic modification that reduces or ablates the activity of a phosphoglucose isomerase;
   a genetic modification that reduces or ablates the activity of a GntR; and
   one or more of:
      a genetic modification that reduces or ablates the activity of a pyruvate formate lyase; and
      a recombinant pyruvate decarboxylase gene.

2. The recombinant microorganism of claim 1 wherein the microorganism is a bacterium.

3. The recombinant microorganism of claim 1 comprising a genetic modification that reduces or ablates the activity of a pyruvate formate lyase.

4. The recombinant microorganism of claim 1 further comprising a genetic modification that reduces or ablates the activity of a lactate dehydrogenase.

5. The recombinant microorganism of claim 1 comprising a recombinant pyruvate decarboxylase gene and further comprising a recombinant alcohol dehydrogenase gene.

6. The recombinant microorganism of claim 1 further comprising one or more of:
   a genetic modification that reduces or ablates the activity of a lactate dehydrogenase; and
   a recombinant alcohol dehydrogenase gene.

7. The recombinant microorganism of claim 1 comprising:
   a genetic modification that reduces or ablates the activity of a pyruvate formate lyase;
   a genetic modification that reduces or ablates the activity of a lactate dehydrogenase;
   a recombinant pyruvate decarboxylase gene; and
   a recombinant alcohol dehydrogenase gene.

8. A method of consuming a carbohydrate comprising culturing the recombinant microorganism of claim 1 in a medium comprising the carbohydrate, wherein the microorganism consumes the carbohydrate during the culturing.

9. The method of claim 8 wherein the medium comprises glucose and xylose.

10. The method of claim 9 wherein the microorganism consumes at least about 10% of an initial amount of the xylose in the medium during the time the microorganism consumes about 20% of an initial amount of the glucose in the medium.

11. The method of claim 8 wherein the medium comprises a biomass hydrolysate.

12. The method of claim 11 wherein the biomass hydrolysate is an enzymatic hydrolysate, an acid hydrolysate, or a hydrolysate of an ionic liquid.

13. The method of claim 8 wherein the microorganism is adapted to growth in a first medium comprising a component selected from the group consisting of glucose, xylose, and ethanol prior to culturing the microorganism in the medium.

14. The method of claim 8 wherein the culturing produces at least about 300 mM ethanol.

15. The recombinant microorganism of claim 1 further comprising a recombinant alcohol dehydrogenase gene.

16. The recombinant microorganism of claim 1 comprising a recombinant pyruvate decarboxylase gene.

* * * * *

SEQUENCE LISTING

<160> NUMBER OF SEQ ID NOS: 36

<210> SEQ ID NO 1

```
<211> LENGTH: 1728
<212> TYPE: DNA
<213> ORGANISM: Escherichia coli

<400> SEQUENCE: 1
atgatttcag gcattttagc atccccgggt atcgctttcg gtaaagctct gcttctgaaa        60
gaagacgaaa ttgtcattga ccggaaaaaa atttctgccg accaggttga tcaggaagtt       120
gaacgttttc tgagcggtcg tgccaaggca tcagcccagc tggaaacgat caaaacgaaa       180
gctggtgaaa cgttcggtga agaaaaagaa gccatctttg aagggcatat tatgctgctc       240
gaagatgagg agctggagca ggaaatcata gccctgatta agataagca catgacagct        300 gacgcagctg ctcatgaagt tatcgaaggt caggcttctg ccctggaaga gctggatgat       360
gaatacctga agaacgtgc ggctgacgta cgtgatatcg gtaagcgcct gctgcgcaac        420
atcctgggcc tgaagattat cgacctgagc gccattcagg atgaagtcat tctggttgcc       480
gctgacctga cgccgtccga aaccgcacag ctgaacctga gaaggtgct gggtttcatc        540 accgacgcgg gtggccgtac ttcccacacc tctatcatgg cgcgttctct ggaactacct       600
gctatcgtgg gtaccggtag cgtcacctct caggtgaaaa atgacgacta tctgattctg       660
gatgccgtaa ataatcaggt ttacgtcaat ccaaccaacg aagttattga taaatgcgc        720 gctgttcagg agcaagtggc ttctgaaaaa gcagagcttg ctaaactgaa agatctgcca       780
gctattacgc tggacggtca ccaggtagaa gtatgcgcta acattggtac ggttcgtgac       840
gttgaaggtg cagagcgtaa cggcgctgaa ggcgttggtc tgtatcgtac tgagttcctg       900
ttcatggacc gcgacgcact gccccactga agaacagt ttgctgctta caaagcagtg         960
gctgaagcgt gtggctcgca agcggttatc gttcgtacca tggacatcgg cggcgacaaa      1020
gagctgccat acatgaactt cccgaaagaa gagaacccgt tcctcggctg gcgcgctatc      1080
cgtatcgcga tggatcgtag agagatcctg cgcgatcagc tccgcgctat cctgcgtgcc      1140
tcggctttcg gtaaattgcg cattatgttc ccgatgatca tctctgttga agaagtgcgt      1200
gcactgcgca aagagatcga aatctacaaa caggaactgc gcgacgaagg taaagcgttt      1260
gacgagtcaa ttgaaatcgg cgtaatggtg gaaacaccgg ctgccgcaac aattgcacgt      1320
catttagcca agaagttga tttctttagt atcggcacca atgatttaac gcagtacact       1380
ctggcagttg accgtggtaa tgatatgatt tcacacctt taccagccaat gtcaccgtcc      1440 gtgctgaact tgatcaagca agttattgat gcttctcatg ctgaaggcaa atggactggc      1500
atgtgtggtg agcttgctgg cgatgaacgt gctacacttc tgttgctggg atgggtctg       1560 gacgaattct ctatgagcgc catttctatc ccgcgcatta agaagattat ccgtaacacg      1620
aacttcgaag atgcgaaggt gttagcagag caggctcttg ctcaaccgac aacggacgag      1680
ttaatgacgc tggttaacaa gttcattgaa gaaaaaacaa tctgctaa                   1728

<210> SEQ ID NO 2
<211> LENGTH: 575
<212> TYPE: PRT
<213> ORGANISM: Escherichia coli

<400> SEQUENCE: 2

Met Ile Ser Gly Ile Leu Ala Ser Pro Gly Ile Ala Phe Gly Lys Ala
1               5                   10                  15

Leu Leu Leu Lys Glu Asp Glu Ile Val Ile Asp Arg Lys Lys Ile Ser
                20                  25                  30

Ala Asp Gln Val Asp Gln Glu Val Glu Arg Phe Leu Ser Gly Arg Ala
```

-continued

```
              35                  40                  45
Lys Ala Ser Ala Gln Leu Glu Thr Ile Lys Thr Lys Ala Gly Glu Thr
         50                  55                  60
Phe Gly Glu Glu Lys Glu Ala Ile Phe Glu Gly His Ile Met Leu Leu
 65                  70                  75                  80
Glu Asp Glu Glu Leu Glu Gln Glu Ile Ile Ala Leu Ile Lys Asp Lys
                 85                  90                  95
His Met Thr Ala Asp Ala Ala His Glu Val Ile Glu Gly Gln Ala
            100                 105                 110
Ser Ala Leu Glu Glu Leu Asp Asp Glu Tyr Leu Lys Glu Arg Ala Ala
            115                 120                 125
Asp Val Arg Asp Ile Gly Lys Arg Leu Leu Arg Asn Ile Leu Gly Leu
        130                 135                 140
Lys Ile Ile Asp Leu Ser Ala Ile Gln Asp Glu Val Ile Leu Val Ala
145                 150                 155                 160
Ala Asp Leu Thr Pro Ser Glu Thr Ala Gln Leu Asn Leu Lys Lys Val
                165                 170                 175
Leu Gly Phe Ile Thr Asp Ala Gly Gly Arg Thr Ser His Thr Ser Ile
            180                 185                 190
Met Ala Arg Ser Leu Glu Leu Pro Ala Ile Val Gly Thr Gly Ser Val
        195                 200                 205
Thr Ser Gln Val Lys Asn Asp Asp Tyr Leu Ile Leu Asp Ala Val Asn
210                 215                 220
Asn Gln Val Tyr Val Asn Pro Thr Asn Glu Val Ile Asp Lys Met Arg
225                 230                 235                 240
Ala Val Gln Glu Gln Val Ala Ser Glu Lys Ala Glu Leu Ala Lys Leu
            245                 250                 255
Lys Asp Leu Pro Ala Ile Thr Leu Asp Gly His Gln Val Glu Val Cys
        260                 265                 270
Ala Asn Ile Gly Thr Val Arg Asp Val Glu Gly Ala Glu Arg Asn Gly
        275                 280                 285
Ala Glu Gly Val Gly Leu Tyr Arg Thr Glu Phe Leu Phe Met Asp Arg
        290                 295                 300
Asp Ala Leu Pro Thr Glu Glu Glu Gln Phe Ala Ala Tyr Lys Ala Val
305                 310                 315                 320
Ala Glu Ala Cys Gly Ser Gln Ala Val Ile Val Arg Thr Met Asp Ile
            325                 330                 335
Gly Gly Asp Lys Glu Leu Pro Tyr Met Asn Phe Pro Lys Glu Glu Asn
            340                 345                 350
Pro Phe Leu Gly Trp Arg Ala Ile Arg Ile Ala Met Asp Arg Arg Glu
        355                 360                 365
Ile Leu Arg Asp Gln Leu Arg Ala Ile Leu Arg Ala Ser Ala Phe Gly
        370                 375                 380
Lys Leu Arg Ile Met Phe Pro Met Ile Ile Ser Val Glu Glu Val Arg
385                 390                 395                 400
Ala Leu Arg Lys Glu Ile Glu Ile Tyr Lys Gln Glu Leu Arg Asp Glu
            405                 410                 415
Gly Lys Ala Phe Asp Glu Ser Ile Glu Ile Gly Val Met Val Glu Thr
            420                 425                 430
Pro Ala Ala Ala Thr Ile Ala Arg His Leu Ala Lys Glu Val Asp Phe
        435                 440                 445
Phe Ser Ile Gly Thr Asn Asp Leu Thr Gln Tyr Thr Leu Ala Val Asp
450                 455                 460
```

Arg Gly Asn Asp Met Ile Ser His Leu Tyr Gln Pro Met Ser Pro Ser
465                 470                 475                 480

Val Leu Asn Leu Ile Lys Gln Val Ile Asp Ala Ser His Ala Glu Gly
                485                 490                 495

Lys Trp Thr Gly Met Cys Gly Glu Leu Ala Gly Asp Glu Arg Ala Thr
            500                 505                 510

Leu Leu Leu Leu Gly Met Gly Leu Asp Glu Phe Ser Met Ser Ala Ile
        515                 520                 525

Ser Ile Pro Arg Ile Lys Lys Ile Arg Asn Thr Asn Phe Glu Asp
    530                 535                 540

Ala Lys Val Leu Ala Glu Gln Ala Leu Ala Gln Pro Thr Thr Asp Glu
545                 550                 555                 560

Leu Met Thr Leu Val Asn Lys Phe Ile Glu Glu Lys Thr Ile Cys
                565                 570                 575

<210> SEQ ID NO 3
<211> LENGTH: 258
<212> TYPE: DNA
<213> ORGANISM: Escherichia coli

<400> SEQUENCE: 3
atgttccagc aagaagttac cattaccgct ccgaacggtc tgcacacccg ccctgctgcc      60
cagtttgtaa agaagctaa gggcttcact tctgaaatta ctgtgacttc aacggcaaa      120 agcgccagcg cgaaaagcct gtttaaactg cagactctgg gcctgactca aggtaccgtt     180
gtgactatct ccgcagaagg cgaagacgag cagaaagcgg ttgaacatct ggttaaactg     240
atggcggaac tcgagtaa                                                    258

<210> SEQ ID NO 4
<211> LENGTH: 85
<212> TYPE: PRT
<213> ORGANISM: Escherichia coli

<400> SEQUENCE: 4

Met Phe Gln Gln Glu Val Thr Ile Thr Ala Pro Asn Gly Leu His Thr
1               5                   10                  15

Arg Pro Ala Ala Gln Phe Val Lys Glu Ala Lys Gly Phe Thr Ser Glu
            20                  25                  30

Ile Thr Val Thr Ser Asn Gly Lys Ser Ala Ser Ala Lys Ser Leu Phe
        35                  40                  45

Lys Leu Gln Thr Leu Gly Leu Thr Gln Gly Thr Val Val Thr Ile Ser
    50                  55                  60

Ala Glu Gly Glu Asp Glu Gln Lys Ala Val Glu His Leu Val Lys Leu
65                  70                  75                  80

Met Ala Glu Leu Glu
                85

<210> SEQ ID NO 5
<211> LENGTH: 1131
<212> TYPE: DNA
<213> ORGANISM: Escherichia coli

<400> SEQUENCE: 5
atgttccagt tatccgtaca ggacatccat ccgggcgaaa aggccggaga caaagaagag      60
gcgattcgcc aggtcgctgc ggcgctggtg caggccggta atgtagcaga aggctacgtc     120
aatggcatgc tggcgcgcga acagcaaacc tcaacgttcc tcggcaatgg tattgctatt     180

```
ccacacggca ctaccgacac ccgcgatcag gtgctgaaaa ccggcgttca ggtatttcag    240
ttcccggaag gcgtcacctg gggtgacggt caggtagcgt acgtggcaat cggtattgct    300
gccagctcgg atgaacatct gggcctgcta cgccagctga cccacgtact gagcgatgat    360
tccgttgctg aacaactgaa gtcagcaaca acagcagaag aacttcgcgc attactgatg    420
ggcgaaaagc agagtgagca gctgaagctc gacaacgaaa tgctgacact ggatatcgtc    480
gccagcgatc tgctgactct tcaggcgctg aacgctgcgc gtctgaaaga ggcgggggca    540
gttgacgcca ctttcgtcac caaagccatc aatgaacaac cgctgaatct cggacagggt    600
atctggctga gcgatagcgc cgaaggcaat ctgcgtagcg cgattgcggt aagccgtgcg    660
gcaaatgctt ttgatgtgga cggcgaaacg gcagccatgc tggtgagtgt ggcgatgaat    720
gacgatcagc ccatcgcggt tcttaagcgt ctcgctgatt tattgctcga caataaagct    780
gaccgcttgc tgaaagcgga tgcggcaacg ttgctggcgc tgctgaccag cgatgatgcg    840
ccgaccgacg acgtgttaag cgcggagttt gtggtgcgca atgaacacgg cctgcatgct    900
cgtccaggta ccatgctggt caataccatt aaacaattta acagtgatat taccgtgaca    960
aaccttgatg gtaccggcaa accggcaaac ggacgtagtc tgatgaaagt tgtggcactt   1020
ggcgttaaga aaggtcatcg cctacgcttt accgcccagg gtgcagatgc tgaacaggcg   1080
ctgaaagcaa tcggcgacgc tatcgctgct ggtcttgggg agggcgcata a            1131

<210> SEQ ID NO 6
<211> LENGTH: 376
<212> TYPE: PRT
<213> ORGANISM: Escherichia coli

<400> SEQUENCE: 6

Met Phe Gln Leu Ser Val Gln Asp Ile His Pro Gly Glu Lys Ala Gly
1               5                  10                  15

Asp Lys Glu Glu Ala Ile Arg Gln Val Ala Ala Leu Val Gln Ala
            20                  25                  30

Gly Asn Val Ala Glu Gly Tyr Val Asn Gly Met Leu Ala Arg Glu Gln
        35                  40                  45

Gln Thr Ser Thr Phe Leu Gly Asn Gly Ile Ala Ile Pro His Gly Thr
    50                  55                  60

Thr Asp Thr Arg Asp Gln Val Leu Lys Thr Gly Val Gln Val Phe Gln
65                  70                  75                  80

Phe Pro Glu Gly Val Thr Trp Gly Asp Gly Gln Val Ala Tyr Val Ala
                85                  90                  95

Ile Gly Ile Ala Ala Ser Ser Asp Glu His Leu Gly Leu Leu Arg Gln
            100                 105                 110

Leu Thr His Val Leu Ser Asp Asp Ser Val Ala Glu Gln Leu Lys Ser
        115                 120                 125

Ala Thr Thr Ala Glu Glu Leu Arg Ala Leu Leu Met Gly Glu Lys Gln
    130                 135                 140

Ser Glu Gln Leu Lys Leu Asp Asn Glu Met Leu Thr Leu Asp Ile Val
145                 150                 155                 160

Ala Ser Asp Leu Leu Thr Leu Gln Ala Leu Asn Ala Ala Arg Leu Lys
                165                 170                 175

Glu Ala Gly Ala Val Asp Ala Thr Phe Val Thr Lys Ala Ile Asn Glu
            180                 185                 190

Gln Pro Leu Asn Leu Gly Gln Gly Ile Trp Leu Ser Asp Ser Ala Glu
        195                 200                 205
```

Gly Asn Leu Arg Ser Ala Ile Ala Val Ser Arg Ala Ala Asn Ala Phe
    210                 215                 220

Asp Val Asp Gly Glu Thr Ala Ala Met Leu Val Ser Val Ala Met Asn
225                 230                 235                 240

Asp Asp Gln Pro Ile Ala Val Leu Lys Arg Leu Ala Asp Leu Leu
                245                 250                 255

Asp Asn Lys Ala Asp Arg Leu Leu Lys Ala Asp Ala Ala Thr Leu Leu
            260                 265                 270

Ala Leu Leu Thr Ser Asp Asp Ala Pro Thr Asp Asp Val Leu Ser Ala
        275                 280                 285

Glu Phe Val Val Arg Asn Glu His Gly Leu His Ala Arg Pro Gly Thr
    290                 295                 300

Met Leu Val Asn Thr Ile Lys Gln Phe Asn Ser Asp Ile Thr Val Thr
305                 310                 315                 320

Asn Leu Asp Gly Thr Gly Lys Pro Ala Asn Gly Arg Ser Leu Met Lys
                325                 330                 335

Val Val Ala Leu Gly Val Lys Lys Gly His Arg Leu Arg Phe Thr Ala
            340                 345                 350

Gln Gly Ala Asp Ala Glu Gln Ala Leu Lys Ala Ile Gly Asp Ala Ile
        355                 360                 365

Ala Ala Gly Leu Gly Glu Gly Ala
    370                 375

<210> SEQ ID NO 7
<211> LENGTH: 510
<212> TYPE: DNA
<213> ORGANISM: Escherichia coli

<400> SEQUENCE: 7
atgggtttgt tcgataaact gaaatctctg gtttccgacg acaagaagga taccggaact      60
attgagatca ttgctccgct ctctggcgag atcgtcaata tcgaagacgt gccggatgtc     120 gttttttgcgg aaaaaatcgt tggtgatggt attgctatca aaccaacggg taacaaaatg    180
gtcgcgccag tagacggcac cattggtaaa tctttgaaa ccaaccacgc attctctatc     240
gaatctgata gcggcgttga actgttcgtc cacttcggta tcgacaccgt tgaactgaaa    300
ggcgaaggct tcaagcgtat tgctgaagaa ggtcagcgcg tgaaagttgg cgatactgtc    360
attgaatttg atctgccgct gctggaagag aaagccaagt ctaccctgac tccggttgtt    420
atctccaaca tggacgaaat caaagaactg atcaaactgt ccggtagcgt aaccgtgggt    480 gaaacccccgg ttatccgcat caagaagtaa                                    510

<210> SEQ ID NO 8
<211> LENGTH: 169
<212> TYPE: PRT
<213> ORGANISM: Escherichia coli

<400> SEQUENCE: 8

Met Gly Leu Phe Asp Lys Leu Lys Ser Leu Val Ser Asp Asp Lys Lys
1               5                   10                  15

Asp Thr Gly Thr Ile Glu Ile Ile Ala Pro Leu Ser Gly Glu Ile Val
            20                  25                  30

Asn Ile Glu Asp Val Pro Asp Val Val Phe Ala Glu Lys Ile Val Gly
        35                  40                  45

Asp Gly Ile Ala Ile Lys Pro Thr Gly Asn Lys Met Val Ala Pro Val
    50                  55                  60

Asp Gly Thr Ile Gly Lys Ile Phe Glu Thr Asn His Ala Phe Ser Ile
65                  70                  75                  80

Glu Ser Asp Ser Gly Val Glu Leu Phe Val His Phe Gly Ile Asp Thr
                85                  90                  95

Val Glu Leu Lys Gly Glu Gly Phe Lys Arg Ile Ala Glu Gly Gln
                100                 105                 110

Arg Val Lys Val Gly Asp Thr Val Ile Glu Phe Asp Leu Pro Leu Leu
            115                 120                 125

Glu Glu Lys Ala Lys Ser Thr Leu Thr Pro Val Val Ile Ser Asn Met
130                 135                 140

Asp Glu Ile Lys Glu Leu Ile Lys Leu Ser Gly Ser Val Thr Val Gly
145                 150                 155                 160

Glu Thr Pro Val Ile Arg Ile Lys Lys
                165

<210> SEQ ID NO 9
<211> LENGTH: 1434
<212> TYPE: DNA
<213> ORGANISM: Escherichia coli

<400> SEQUENCE: 9
atgtttaaga atgcatttgc taacctgcaa aaggtcggta atcgctgat gctgccggta        60
tccgtactgc ctatcgcagg tattctgctg ggcgtcggtt ccgcgaattt cagctggctg      120
cccgccgttg tatcgcatgt tatggcagaa gcaggcggtt ccgtctttgc aaacatgcca      180
ctgattttg cgatcggtgt cgccctcggc tttaccaata cgatggcgt atccgcgctg        240
gctgcagttg ttgcctatgg catcatggtt aaaaccatgg ccgtggttgc gccactggta      300
ctgcatttac ctgctgaaga atcgcctct aaacacctgg cggatactgg cgtactcgga       360
gggattatct ccggtgcgat cgcagcgtac atgtttaacc gtttctaccg tattaagctg      420
cctgagtatc ttggcttctt tgccggtaaa cgctttgtgc cgatcatttc tggcctggct      480
gccatcttta ctggcgttgt gctgtccttc atttggccgc cgattggttc tgcaatccag      540
accttctctc agtgggctgc ttaccagaac ccggtagttg cgtttggcat tacggtttc       600
atcgaacgtt gcctggtacc gtttggtctg caccacatct ggaacgtacc tttccagatg      660
cagattggtg aataccaccaa cgcagcaggt caggttttcc acggcgacat tccgcgttat     720
atggcgggtg acccgactgc gggtaaactg tctggtggct tcctgttcaa aatgtacggt      780
ctgccagctg ccgcaattgc tatctggcac tctgctaaac agaaaaccg cgcgaaagtg       840
ggcggtatta tgatctccgc ggcgctgacc tcgttcctga ccggtatcac cgagccgatc      900
gagttctcct tcatgttcgt tgcgccgatc ctgtacatca tccackcgat tctggcaggc      960
ctggcattcc aatctgtat tcttctgggg atgcgtgacg gtacgtcgtt tcgcacggt       1020
ctgatcgact tcatcgttct gtctggtaac agcagcaaac tgtggctgtt cccgatcgtc     1080
ggtatcggtt atgcgattgt ttactacacc atcttccgcg tgctgattaa agcactggat     1140
ctgaaaacgc cgggtcgtga agacgcgact gaagatgcaa aagcgacagg taccagcgaa     1200
atggcaccgg ctctggttgc tgcatttggt ggtaaagaaa acattactaa cctcgacgca     1260
tgtattaccc gtctgcgcgt cagcgttgct gatgtgtcta aagtggatca ggctggcctg     1320
aagaaactgg gcgcagcggg cgtagtggtt gctggttctg gtgttcaggc gattttcggt     1380
actaaatccg ataaccctgaa aaccgagatg gatgagtaca tccgtaacca ctaa          1434

<210> SEQ ID NO 10
<211> LENGTH: 477
<212> TYPE: PRT
<213> ORGANISM: Escherichia coli

<400> SEQUENCE: 10

```
Met Phe Lys Asn Ala Phe Ala Asn Leu Gln Lys Val Gly Lys Ser Leu
1               5                   10                  15

Met Leu Pro Val Ser Val Leu Pro Ile Ala Gly Ile Leu Leu Gly Val
                20                  25                  30

Gly Ser Ala Asn Phe Ser Trp Leu Pro Ala Val Val Ser His Val Met
            35                  40                  45

Ala Glu Ala Gly Gly Ser Val Phe Ala Asn Met Pro Leu Ile Phe Ala
        50                  55                  60

Ile Gly Val Ala Leu Gly Phe Thr Asn Asn Asp Gly Val Ser Ala Leu
65                  70                  75                  80

Ala Ala Val Val Ala Tyr Gly Ile Met Val Lys Thr Met Ala Val Val
                85                  90                  95

Ala Pro Leu Val Leu His Leu Pro Ala Glu Glu Ile Ala Ser Lys His
                100                 105                 110

Leu Ala Asp Thr Gly Val Leu Gly Gly Ile Ile Ser Gly Ala Ile Ala
            115                 120                 125

Ala Tyr Met Phe Asn Arg Phe Tyr Arg Ile Lys Leu Pro Glu Tyr Leu
        130                 135                 140

Gly Phe Phe Ala Gly Lys Arg Phe Val Pro Ile Ile Ser Gly Leu Ala
145                 150                 155                 160

Ala Ile Phe Thr Gly Val Val Leu Ser Phe Ile Trp Pro Pro Ile Gly
                165                 170                 175

Ser Ala Ile Gln Thr Phe Ser Gln Trp Ala Ala Tyr Gln Asn Pro Val
                180                 185                 190

Val Ala Phe Gly Ile Tyr Gly Phe Ile Glu Arg Cys Leu Val Pro Phe
            195                 200                 205

Gly Leu His His Ile Trp Asn Val Pro Phe Gln Met Gln Ile Gly Glu
        210                 215                 220

Tyr Thr Asn Ala Ala Gly Gln Val Phe His Gly Asp Ile Pro Arg Tyr
225                 230                 235                 240

Met Ala Gly Asp Pro Thr Ala Gly Lys Leu Ser Gly Gly Phe Leu Phe
                245                 250                 255

Lys Met Tyr Gly Leu Pro Ala Ala Ala Ile Ala Ile Trp His Ser Ala
                260                 265                 270

Lys Pro Glu Asn Arg Ala Lys Val Gly Gly Ile Met Ile Ser Ala Ala
            275                 280                 285

Leu Thr Ser Phe Leu Thr Gly Ile Thr Glu Pro Ile Glu Phe Ser Phe
        290                 295                 300

Met Phe Val Ala Pro Ile Leu Tyr Ile Ile His Ala Ile Leu Ala Gly
305                 310                 315                 320

Leu Ala Phe Pro Ile Cys Ile Leu Leu Gly Met Arg Asp Gly Thr Ser
                325                 330                 335

Phe Ser His Gly Leu Ile Asp Phe Ile Val Leu Ser Gly Asn Ser Ser
                340                 345                 350

Lys Leu Trp Leu Phe Pro Ile Val Gly Ile Gly Tyr Ala Ile Val Tyr
            355                 360                 365

Tyr Thr Ile Phe Arg Val Leu Ile Lys Ala Leu Asp Leu Lys Thr Pro
        370                 375                 380
```

```
Gly Arg Glu Asp Ala Thr Glu Asp Ala Lys Ala Thr Gly Thr Ser Glu
385                 390                 395                 400

Met Ala Pro Ala Leu Val Ala Ala Phe Gly Gly Lys Glu Asn Ile Thr
                405                 410                 415

Asn Leu Asp Ala Cys Ile Thr Arg Leu Arg Val Ser Val Ala Asp Val
            420                 425                 430

Ser Lys Val Asp Gln Ala Gly Leu Lys Lys Leu Gly Ala Ala Gly Val
        435                 440                 445

Val Val Ala Gly Ser Gly Val Gln Ala Ile Phe Gly Thr Lys Ser Asp
    450                 455                 460

Asn Leu Lys Thr Glu Met Asp Glu Tyr Ile Arg Asn His
465                 470                 475

<210> SEQ ID NO 11
<211> LENGTH: 1650
<212> TYPE: DNA
<213> ORGANISM: Escherichia coli

<400> SEQUENCE: 11
```

| | | | | | |
|---|---|---|---|---|---|
| atgaaaaaca | tcaatccaac | gcagaccgct | gcctggcagg | cactacagaa | acacttcgat       60 |
| gaaatgaaag | acgttacgat | cgccgatctt | tttgctaaag | acggcgatcg | ttttctaag       120 |
| ttctccgcaa | ccttcgacga | tcagatgctg | gtggattact | ccaaaaaccg | catcactgaa      180 |
| gagacgctgg | cgaaattaca | ggatctggcg | aaagagtgcg | atctggcggg | cgcgattaag      240 |
| tcgatgttct | ctggcgagaa | gatcaaccgc | actgaaaacc | gcgccgtgct | gcacgtagcg      300 |
| ctgcgtaacc | gtagcaatac | cccgattttg | gttgatggca | agacgtaat | gccggaagtc      360 |
| aacgcggtgc | tggagaagat | gaaaaccttc | tcagaagcga | ttatttccgg | tgagtggaaa      420 |
| ggttataccg | gcaaagcaat | cactgacgta | gtgaacatcg | gatcggcgg | ttctgacctc      480 |
| ggcccataca | tggtgaccga | agctctgcgt | ccgtacaaaa | accacctgaa | catgcacttt      540 |
| gtttctaacg | tcgatgggac | tcacatcgcg | gaagtgctga | aaaagtaaa | cccggaaacc      600 |
| acgctgttct | tggtagcatc | taaaaccttc | accactcagg | aaactatgac | caacgcccat      660 |
| agcgcgcgtg | actggttcct | gaaagcggca | ggtgatgaaa | acacgttgc | aaaacacttt      720 |
| gcggcgcttt | ccaccaatgc | caaagccgtt | ggcgagtttg | gtattgatac | tgccaacatg      780 |
| ttcgagttct | gggactgggt | tggcggccgt | tactcttttgt | ggtcagcgat | ggcctgtcg      840 |
| attgttctct | ccatcggctt | tgataacttc | gttgaactgc | tttccggcgc | acgcgcgatg      900 |
| gacaagcatt | tctccaccac | gcctgccgag | aaaaacctgc | ctgtactgct | ggcgctgatt      960 |
| ggcatctggt | acaacaattt | ctttggtgcg | aaactgaag | cgattctgcc | gtatgaccag     1020 |
| tatatgcacc | gttcgcggc | gtacttccag | cagggcaata | tggagtccaa | cggtaagtat     1080 |
| gttgaccgta | acggtaacgt | tgtggattac | cagactggcc | cgattatctg | gggtgaacca     1140 |
| ggcactaacg | tcagcacgc | gttctaccag | ctgatccacc | agggaaccaa | aatggtaccg     1200 |
| tgcgattca | tcgctccggc | tatcacccat | aacccgctct | ctgatcatca | ccagaaactg     1260 |
| ctgtctaact | tcttcgccca | gaccgaagcg | ctggcgtttg | gtaaatcccg | cgaagtggtt     1320 |
| gagcaggaat | atcgtgatca | gggtaaagat | ccggcaacgc | ttgactacgt | ggtgccgttc     1380 |
| aaagtattcg | aaggtaaccg | cccgaccaac | tccatcctgc | tgcgtgaaat | cactccgttc     1440 |
| agcctgggtg | cgttgattgc | gctgtatgag | cacaaaatct | ttactcaggg | cgtgatcctg     1500 |
| aacatcttca | cctccgacca | gtggggcgtg | aactgggta | aacagctggc | gaaccgtatt     1560 |
| ctgccagagc | tgaaagatga | taaagaaatc | agcagccacg | atagctcgac | caatggtctg     1620 | attaaccgct ataaagcgtg gcgcggttaa                    1650

<210> SEQ ID NO 12
<211> LENGTH: 549
<212> TYPE: PRT
<213> ORGANISM: Escherichia coli

<400> SEQUENCE: 12

Met Lys Asn Ile Asn Pro Thr Gln Thr Ala Ala Trp Gln Ala Leu Gln
1               5                   10                  15

Lys His Phe Asp Glu Met Lys Asp Val Thr Ile Ala Asp Leu Phe Ala
            20                  25                  30

Lys Asp Gly Asp Arg Phe Ser Lys Phe Ser Ala Thr Phe Asp Asp Gln
        35                  40                  45

Met Leu Val Asp Tyr Ser Lys Asn Arg Ile Thr Glu Glu Thr Leu Ala
    50                  55                  60

Lys Leu Gln Asp Leu Ala Lys Glu Cys Asp Leu Ala Gly Ala Ile Lys
65                  70                  75                  80

Ser Met Phe Ser Gly Glu Lys Ile Asn Arg Thr Glu Asn Arg Ala Val
                85                  90                  95

Leu His Val Ala Leu Arg Asn Arg Ser Asn Thr Pro Ile Leu Val Asp
            100                 105                 110

Gly Lys Asp Val Met Pro Glu Val Asn Ala Val Leu Glu Lys Met Lys
        115                 120                 125

Thr Phe Ser Glu Ala Ile Ile Ser Gly Glu Trp Lys Gly Tyr Thr Gly
    130                 135                 140

Lys Ala Ile Thr Asp Val Val Asn Ile Gly Ile Gly Gly Ser Asp Leu
145                 150                 155                 160

Gly Pro Tyr Met Val Thr Glu Ala Leu Arg Pro Tyr Lys Asn His Leu
                165                 170                 175

Asn Met His Phe Val Ser Asn Val Asp Gly Thr His Ile Ala Glu Val
            180                 185                 190

Leu Lys Lys Val Asn Pro Glu Thr Thr Leu Phe Leu Val Ala Ser Lys
        195                 200                 205

Thr Phe Thr Thr Gln Glu Thr Met Thr Asn Ala His Ser Ala Arg Asp
    210                 215                 220

Trp Phe Leu Lys Ala Ala Gly Asp Glu Lys His Val Ala Lys His Phe
225                 230                 235                 240

Ala Ala Leu Ser Thr Asn Ala Lys Ala Val Gly Glu Phe Gly Ile Asp
                245                 250                 255

Thr Ala Asn Met Phe Glu Phe Trp Asp Trp Val Gly Gly Arg Tyr Ser
            260                 265                 270

Leu Trp Ser Ala Ile Gly Leu Ser Ile Val Leu Ser Ile Gly Phe Asp
        275                 280                 285

Asn Phe Val Glu Leu Leu Ser Gly Ala His Ala Met Asp Lys His Phe
    290                 295                 300

Ser Thr Thr Pro Ala Glu Lys Asn Leu Pro Val Leu Leu Ala Leu Ile
305                 310                 315                 320

Gly Ile Trp Tyr Asn Asn Phe Phe Gly Ala Glu Thr Glu Ala Ile Leu
                325                 330                 335

Pro Tyr Asp Gln Tyr Met His Arg Phe Ala Ala Tyr Phe Gln Gln Gly
            340                 345                 350

Asn Met Glu Ser Asn Gly Lys Tyr Val Asp Arg Asn Gly Asn Val Val
        355                 360                 365

```
Asp Tyr Gln Thr Gly Pro Ile Ile Trp Gly Glu Pro Gly Thr Asn Gly
        370                 375                 380

Gln His Ala Phe Tyr Gln Leu Ile His Gln Gly Thr Lys Met Val Pro
385                 390                 395                 400

Cys Asp Phe Ile Ala Pro Ala Ile Thr His Asn Pro Leu Ser Asp His
                405                 410                 415

His Gln Lys Leu Leu Ser Asn Phe Phe Ala Gln Thr Glu Ala Leu Ala
            420                 425                 430

Phe Gly Lys Ser Arg Glu Val Val Glu Gln Glu Tyr Arg Asp Gln Gly
        435                 440                 445

Lys Asp Pro Ala Thr Leu Asp Tyr Val Val Pro Phe Lys Val Phe Glu
    450                 455                 460

Gly Asn Arg Pro Thr Asn Ser Ile Leu Leu Arg Glu Ile Thr Pro Phe
465                 470                 475                 480

Ser Leu Gly Ala Leu Ile Ala Leu Tyr Glu His Lys Ile Phe Thr Gln
                485                 490                 495

Gly Val Ile Leu Asn Ile Phe Thr Phe Asp Gln Trp Gly Val Glu Leu
            500                 505                 510

Gly Lys Gln Leu Ala Asn Arg Ile Leu Pro Glu Leu Lys Asp Asp Lys
        515                 520                 525

Glu Ile Ser Ser His Asp Ser Ser Thr Asn Gly Leu Ile Asn Arg Tyr
    530                 535                 540

Lys Ala Trp Arg Gly
545

<210> SEQ ID NO 13
<211> LENGTH: 996
<212> TYPE: DNA
<213> ORGANISM: Escherichia coli

<400> SEQUENCE: 13
atgaaaaaga aaagacccgt acttcaggat gtggctgacc gtgtaggcgt gaccaaaatg        60
acggtcagcc gttttttacg caacccggag caggtttccg tcgctctacg cggcaagatt       120
gccgcggctc ttgatgaact gggctatatt cccaatcgtg cgcccgatat cctctctaac       180
gccaccagcc gggcgattgg cgtcctgtta ccttctctca ccaaccaggt tttcgcggaa       240
gtattacgcg gaatcgaaag cgtcaccgac gcgcacggtt atcagaccat gctggcgcac       300
tacggttata aaccggaaat ggagcaagaa cgcctcgaat ccatgctctc ctggaatatc       360
gacggcctga tcctcaccga acgtacccac acgccgcgca ccttaaagat gattgaagtg       420
gcgggtattc ccgtggtgga actgatggac agcaagtcgc catgccttga tatcgccgtc       480
ggttttgata actttgaagc agcacgccag atgaccactg ccattattgc tcgcgggcat       540
cgccacattg cctatctcgg cgcacgtctc gacgaacgta ctatcatcaa acagaaggga       600
tacgaacagg cgatgctgga tgcaggcctg tgccatata gcgtgatggt tgagcaatct       660
tcttcttact cttccggtat tgaactgatt cgccaggcgc ggcgggaata tccgcagctg       720
gatggcgtgt tctgtacgaa tgatgacctg gcggtcggcg cggcgtttga atgtcagcgt       780 ctgggggttaa aagttcctga cgatatggcg attgccggtt tccacggtca tgacattggt       840
caggtgatgg agccacgact tgcgagcgtg ctgacgccgc gtgagcggat gggcagtatt       900
ggcgctgaac gcctgctggc gcgtattcgt ggcgaatctg tgacaccgaa aatgttagat       960
ttaggtttca ccttgtcacc gggcggatct atttaa                                  996
```

<210> SEQ ID NO 14
<211> LENGTH: 331
<212> TYPE: PRT
<213> ORGANISM: Escherichia coli

<400> SEQUENCE: 14

Met Lys Lys Lys Arg Pro Val Leu Gln Asp Val Ala Asp Arg Val Gly
1               5                   10                  15

Val Thr Lys Met Thr Val Ser Arg Phe Leu Arg Asn Pro Glu Gln Val
            20                  25                  30

Ser Val Ala Leu Arg Gly Lys Ile Ala Ala Leu Asp Glu Leu Gly
        35                  40                  45

Tyr Ile Pro Asn Arg Ala Pro Asp Ile Leu Ser Asn Ala Thr Ser Arg
    50                  55                  60

Ala Ile Gly Val Leu Leu Pro Ser Leu Thr Asn Gln Val Phe Ala Glu
65                  70                  75                  80

Val Leu Arg Gly Ile Glu Ser Val Thr Asp Ala His Gly Tyr Gln Thr
                85                  90                  95

Met Leu Ala His Tyr Gly Tyr Lys Pro Glu Met Glu Gln Glu Arg Leu
            100                 105                 110

Glu Ser Met Leu Ser Trp Asn Ile Asp Gly Leu Ile Leu Thr Glu Arg
        115                 120                 125

Thr His Thr Pro Arg Thr Leu Lys Met Ile Glu Val Ala Gly Ile Pro
    130                 135                 140

Val Val Glu Leu Met Asp Ser Lys Ser Pro Cys Leu Asp Ile Ala Val
145                 150                 155                 160

Gly Phe Asp Asn Phe Glu Ala Ala Arg Gln Met Thr Thr Ala Ile Ile
                165                 170                 175

Ala Arg Gly His Arg His Ile Ala Tyr Leu Gly Ala Arg Leu Asp Glu
            180                 185                 190

Arg Thr Ile Ile Lys Gln Lys Gly Tyr Glu Gln Ala Met Leu Asp Ala
        195                 200                 205

Gly Leu Val Pro Tyr Ser Val Met Val Glu Gln Ser Ser Tyr Ser
    210                 215                 220

Ser Gly Ile Glu Leu Ile Arg Gln Ala Arg Arg Glu Tyr Pro Gln Leu
225                 230                 235                 240

Asp Gly Val Phe Cys Thr Asn Asp Asp Leu Ala Val Gly Ala Ala Phe
                245                 250                 255

Glu Cys Gln Arg Leu Gly Leu Lys Val Pro Asp Asp Met Ala Ile Ala
            260                 265                 270

Gly Phe His Gly His Asp Ile Gly Gln Val Met Glu Pro Arg Leu Ala
        275                 280                 285

Ser Val Leu Thr Pro Arg Glu Arg Met Gly Ser Ile Gly Ala Glu Arg
    290                 295                 300

Leu Leu Ala Arg Ile Arg Gly Glu Ser Val Thr Pro Lys Met Leu Asp
305                 310                 315                 320

Leu Gly Phe Thr Leu Ser Pro Gly Gly Ser Ile
                325                 330

<210> SEQ ID NO 15
<211> LENGTH: 990
<212> TYPE: DNA
<213> ORGANISM: Escherichia coli

<400> SEQUENCE: 15

-continued

```
atgaaactcg ccgtttatag cacaaaacag tacgacaaga agtacctgca acaggtgaac    60
gagtcctttg gctttgagct ggaattttt gactttctgc tgacggaaaa aaccgctaaa    120
actgccaatg gctgcgaagc ggtatgtatt tcgtaaacg atgacggcag ccgcccggtg    180
ctggaagagc tgaaaaagca cggcgttaaa tatatcgccc tgcgctgtgc cggtttcaat    240
aacgtcgacc ttgacgcggc aaaagaactg gggctgaaag tagtccgtgt tccagcctat    300
gatccagagg ccgttgctga acacgccatc ggtatgatga tgacgctgaa ccgccgtatt    360
caccgcgcgt atcagcgtac ccgtgatgct aacttctctc tggaaggtct gaccggcttt    420
actatgtatg gcaaaacggc aggcgttatc ggtaccggta aaatcggtgt ggcgatgctg    480
cgcattctga aaggttttgg tatgcgtctg ctggcgttcg atccgtatcc aagtgcagcg    540
gcgctggaac tcggtgtgga gtatgtcgat ctgccaaccc tgttctctga atcagacgtt    600
atctctctgc actgcccgct gacaccggaa aactatcatc tgttgaacga agccgccttc    660
gaacagatga aaaatggcgt gatgatcgtc aataccagtc gcggtgcatt gattgattct    720
caggcagcaa ttgaagcgct gaaaaatcag aaaattggtt cgttgggtat ggacgtgtat    780
gagaacgaac gcgatctatt ctttgaagat aaatccaacg acgtgatcca ggatgacgta    840
ttccgtcgcc tgtctgcctg ccacaacgtg ctgtttaccg gcaccaggc attcctgaca    900
gcagaagctc tgaccagtat ttctcagact acgctgcaaa acttaagcaa tctggaaaaa    960
ggcgaaacct gcccgaacga actggtttaa                                    990
```

<210> SEQ ID NO 16
<211> LENGTH: 329
<212> TYPE: PRT
<213> ORGANISM: Escherichia coli

<400> SEQUENCE: 16

```
Met Lys Leu Ala Val Tyr Ser Thr Lys Gln Tyr Asp Lys Lys Tyr Leu
1               5                   10                  15

Gln Gln Val Asn Glu Ser Phe Gly Phe Glu Leu Glu Phe Phe Asp Phe
            20                  25                  30

Leu Leu Thr Glu Lys Thr Ala Lys Thr Ala Asn Gly Cys Glu Ala Val
        35                  40                  45

Cys Ile Phe Val Asn Asp Asp Gly Ser Arg Pro Val Leu Glu Glu Leu
    50                  55                  60

Lys Lys His Gly Val Lys Tyr Ile Ala Leu Arg Cys Ala Gly Phe Asn
65                  70                  75                  80

Asn Val Asp Leu Asp Ala Ala Lys Glu Leu Gly Leu Lys Val Val Arg
                85                  90                  95

Val Pro Ala Tyr Asp Pro Glu Ala Val Ala Glu His Ala Ile Gly Met
            100                 105                 110

Met Met Thr Leu Asn Arg Arg Ile His Arg Ala Tyr Gln Arg Thr Arg
        115                 120                 125

Asp Ala Asn Phe Ser Leu Glu Gly Leu Thr Gly Phe Thr Met Tyr Gly
    130                 135                 140

Lys Thr Ala Gly Val Ile Gly Thr Gly Lys Ile Gly Val Ala Met Leu
145                 150                 155                 160

Arg Ile Leu Lys Gly Phe Gly Met Arg Leu Leu Ala Phe Asp Pro Tyr
                165                 170                 175

Pro Ser Ala Ala Ala Leu Glu Leu Gly Val Glu Tyr Val Asp Leu Pro
            180                 185                 190

Thr Leu Phe Ser Glu Ser Asp Val Ile Ser Leu His Cys Pro Leu Thr
```

|   | 195 |   |   |   | 200 |   |   |   | 205 |   |   |
|---|---|---|---|---|---|---|---|---|---|---|---|

Pro Glu Asn Tyr His Leu Leu Asn Glu Ala Ala Phe Glu Gln Met Lys
210 215 220

Asn Gly Val Met Ile Val Asn Thr Ser Arg Gly Ala Leu Ile Asp Ser
225 230 235 240

Gln Ala Ala Ile Glu Ala Leu Lys Asn Gln Lys Ile Gly Ser Leu Gly
245 250 255

Met Asp Val Tyr Glu Asn Glu Arg Asp Leu Phe Phe Glu Asp Lys Ser
260 265 270

Asn Asp Val Ile Gln Asp Val Phe Arg Arg Leu Ser Ala Cys His
275 280 285

Asn Val Leu Phe Thr Gly His Gln Ala Phe Leu Thr Ala Glu Ala Leu
290 295 300

Thr Ser Ile Ser Gln Thr Thr Leu Gln Asn Leu Ser Asn Leu Glu Lys
305 310 315 320

Gly Glu Thr Cys Pro Asn Glu Leu Val
325

<210> SEQ ID NO 17
<211> LENGTH: 2283
<212> TYPE: DNA
<213> ORGANISM: Escherichia coli

<400> SEQUENCE: 17

```
atgtccgagc ttaatgaaaa gttagccaca gcctgggaag ttttaccaa aggtgactgg      60
cagaatgaag taaacgtccg tgacttcatt cagaaaaact acactccgta cgagggtgac    120
gagtccttcc tggctggcgc tactgaagcg accaccaccc tgtgggacaa agtaatggaa    180
ggcgttaaac tggaaaaccg cactcacgcg ccagttgact ttgacaccgc tgttgcttcc    240
accatcacct ctcacgacgc tggctacatc aacaagcagc ttgagaaaat cgttggtctg    300
cagactgaag ctccgctgaa acgtgctctt atcccgttcg gtggtatcaa aatgatcgaa    360
ggttcctgca aagcgtacaa ccgcgaactg atccgatga tcaaaaaaat cttcactgaa    420
taccgtaaaa ctcacaacca gggcgtgttc gacgtttaca ctccggacat cctgcgttgc    480
cgtaaatctg tgttctgac cggtctgcca gatgcatatg gccgtggccg tatcatcggt    540
gactaccgtc gcgttgcgct gtacggtatc gactacctga tgaaagacaa actggcacag    600
ttcacttctc tgcaggctga tctggaaaac ggcgtaaacc tggaacagac tatccgtctg    660
cgcgaagaaa tcgctgaaca gcaccgcgct ctgggtcaga tgaaagaaat ggctgcgaaa    720
tacggctacg acatctctgg tccggctacc aacgctcagg aagctatcca gtggacttac    780
ttcggctacc tggctgctgt taagtctcag aacggtgctg caatgtcctt cggtcgtacc    840
tccaccttcc tggatgtgta catcgaacgt gacctgaaag ctggcaagat caccgaacaa    900
gaagcgcagg aaatggttga ccacctggtc atgaaactgc gtatggttcg cttcctgcgt    960
actccggaat acgatgaact gttctctggc gacccgatct gggcaaccga atctatcggt   1020
ggtatgggcc tcgacggtcg taccctggtt accaaaaaca gcttccgttt cctgaacacc   1080
ctgtacacca tggtccgtc tccggaaccg aacatgacca ttctgtggtc tgaaaaactg   1140
ccgctgaact tcaagaaatt cgccgctaaa gtgtccatcg acacctcttc tctgcagtat   1200
gagaacgatg acctgatgcg tccggacttc aacaacgatg actacgctat tgcttgctgc   1260
gtaagcccga tgatcgttgg taaacaaatg cagttcttcg gtgcgcgtgc aaacctggcg   1320
aaaaccatgc tgtacgcaat caacggcggc gttgacgaaa aactgaaaat gcaggttggt   1380
```

```
ccgaagtctg aaccgatcaa aggcgatgtc ctgaactatg atgaagtgat ggagcgcatg   1440
gatcacttca tggactggct ggctaaacag tacatcactg cactgaacat catccactac   1500
atgcacgaca agtacagcta cgaagcctct ctgatggcgc tgcacgaccg tgacgttatc   1560
cgcaccatgg cgtgtggtat cgctggtctg tccgttgctg ctgactccct gtctgcaatc   1620
aaatatgcga agttaaaacc gattcgtgac gaagacggtc tggctatcga cttcgaaatc   1680
gaaggcgaat acccgcagtt tggtaacaat gatccgcgtg tagatgacct ggctgttgac   1740
ctggtagaac gtttcatgaa gaaaattcag aaactgcaca cctaccgtga cgctatcccg   1800
actcagtctg ttctgaccat cacttctaac gttgtgtatg gtaagaaaac gggtaacacc   1860
ccagacggtc gtcgtgctgg cgcgccgttc ggaccgggtg ctaacccgat gcacggtcgt   1920
gaccagaaag gtgcagtagc ctctctgact tccgttgcta aactgccgtt tgcttacgct   1980
aaagatggta tctcctacac cttctctatc gttccgaacg cactgggtaa agacgacgaa   2040
gttcgtaaga ccaacctggc tggtctgatg gatggttact tccaccacga agcatccatc   2100
gaaggtggtc agcacctgaa cgttaacgtg atgaaccgtg aaatgctgct cgacgcgatg   2160
gaaaacccgg aaaatatcc gcagctgacc atccgtgtat ctggctacgc agtacgtttc   2220
aactcgctga ctaaagaaca gcagcaggac gttattactc gtaccttcac tcaatctatg   2280
taa                                                                   2283

<210> SEQ ID NO 18
<211> LENGTH: 760
<212> TYPE: PRT
<213> ORGANISM: Escherichia coli

<400> SEQUENCE: 18

Met Ser Glu Leu Asn Glu Lys Leu Ala Thr Ala Trp Glu Gly Phe Thr
1               5                   10                  15

Lys Gly Asp Trp Gln Asn Glu Val Asn Val Arg Asp Phe Ile Gln Lys
            20                  25                  30

Asn Tyr Thr Pro Tyr Glu Gly Asp Glu Ser Phe Leu Ala Gly Ala Thr
        35                  40                  45

Glu Ala Thr Thr Thr Leu Trp Asp Lys Val Met Glu Gly Val Lys Leu
    50                  55                  60

Glu Asn Arg Thr His Ala Pro Val Asp Phe Asp Thr Ala Val Ala Ser
65                  70                  75                  80

Thr Ile Thr Ser His Asp Ala Gly Tyr Ile Asn Lys Gln Leu Glu Lys
                85                  90                  95

Ile Val Gly Leu Gln Thr Glu Ala Pro Leu Lys Arg Ala Leu Ile Pro
            100                 105                 110

Phe Gly Gly Ile Lys Met Ile Glu Gly Ser Cys Lys Ala Tyr Asn Arg
        115                 120                 125

Glu Leu Asp Pro Met Ile Lys Lys Ile Phe Thr Glu Tyr Arg Lys Thr
    130                 135                 140

His Asn Gln Gly Val Phe Asp Val Tyr Thr Pro Asp Ile Leu Arg Cys
145                 150                 155                 160

Arg Lys Ser Gly Val Leu Thr Gly Leu Pro Asp Ala Tyr Gly Arg Gly
                165                 170                 175

Arg Ile Ile Gly Asp Tyr Arg Arg Val Ala Leu Tyr Gly Ile Asp Tyr
            180                 185                 190

Leu Met Lys Asp Lys Leu Ala Gln Phe Thr Ser Leu Gln Ala Asp Leu
        195                 200                 205
```

```
Glu Asn Gly Val Asn Leu Glu Gln Thr Ile Arg Leu Arg Glu Glu Ile
    210                 215                 220

Ala Glu Gln His Arg Ala Leu Gly Gln Met Lys Glu Met Ala Ala Lys
225                 230                 235                 240

Tyr Gly Tyr Asp Ile Ser Gly Pro Ala Thr Asn Ala Gln Glu Ala Ile
                245                 250                 255

Gln Trp Thr Tyr Phe Gly Tyr Leu Ala Ala Val Lys Ser Gln Asn Gly
            260                 265                 270

Ala Ala Met Ser Phe Gly Arg Thr Ser Thr Phe Leu Asp Val Tyr Ile
        275                 280                 285

Glu Arg Asp Leu Lys Ala Gly Lys Ile Thr Glu Gln Glu Ala Gln Glu
    290                 295                 300

Met Val Asp His Leu Val Met Lys Leu Arg Met Val Arg Phe Leu Arg
305                 310                 315                 320

Thr Pro Glu Tyr Asp Glu Leu Phe Ser Gly Asp Pro Ile Trp Ala Thr
                325                 330                 335

Glu Ser Ile Gly Gly Met Gly Leu Asp Gly Arg Thr Leu Val Thr Lys
            340                 345                 350

Asn Ser Phe Arg Phe Leu Asn Thr Leu Tyr Thr Met Gly Pro Ser Pro
        355                 360                 365

Glu Pro Asn Met Thr Ile Leu Trp Ser Glu Lys Leu Pro Leu Asn Phe
    370                 375                 380

Lys Lys Phe Ala Ala Lys Val Ser Ile Asp Thr Ser Ser Leu Gln Tyr
385                 390                 395                 400

Glu Asn Asp Asp Leu Met Arg Pro Asp Phe Asn Asn Asp Asp Tyr Ala
                405                 410                 415

Ile Ala Cys Cys Val Ser Pro Met Ile Val Gly Lys Gln Met Gln Phe
            420                 425                 430

Phe Gly Ala Arg Ala Asn Leu Ala Lys Thr Met Leu Tyr Ala Ile Asn
        435                 440                 445

Gly Gly Val Asp Glu Lys Leu Lys Met Gln Val Gly Pro Lys Ser Glu
    450                 455                 460

Pro Ile Lys Gly Asp Val Leu Asn Tyr Asp Glu Val Met Glu Arg Met
465                 470                 475                 480

Asp His Phe Met Asp Trp Leu Ala Lys Gln Tyr Ile Thr Ala Leu Asn
                485                 490                 495

Ile Ile His Tyr Met His Asp Lys Tyr Ser Tyr Glu Ala Ser Leu Met
            500                 505                 510

Ala Leu His Asp Arg Asp Val Ile Arg Thr Met Ala Cys Gly Ile Ala
        515                 520                 525

Gly Leu Ser Val Ala Ala Asp Ser Leu Ser Ala Ile Lys Tyr Ala Lys
    530                 535                 540

Val Lys Pro Ile Arg Asp Glu Asp Gly Leu Ala Ile Asp Phe Glu Ile
545                 550                 555                 560

Glu Gly Glu Tyr Pro Gln Phe Gly Asn Asn Asp Pro Arg Val Asp Asp
                565                 570                 575

Leu Ala Val Asp Leu Val Glu Arg Phe Met Lys Lys Ile Gln Lys Leu
            580                 585                 590

His Thr Tyr Arg Asp Ala Ile Pro Thr Gln Ser Val Leu Thr Ile Thr
        595                 600                 605

Ser Asn Val Val Tyr Gly Lys Lys Thr Gly Asn Thr Pro Asp Gly Arg
    610                 615                 620
```

Arg Ala Gly Ala Pro Phe Gly Pro Gly Ala Asn Pro Met His Gly Arg
625                 630                 635                 640

Asp Gln Lys Gly Ala Val Ala Ser Leu Thr Ser Val Ala Lys Leu Pro
            645                 650                 655

Phe Ala Tyr Ala Lys Asp Gly Ile Ser Tyr Thr Phe Ser Ile Val Pro
        660                 665                 670

Asn Ala Leu Gly Lys Asp Asp Glu Val Arg Lys Thr Asn Leu Ala Gly
            675                 680                 685

Leu Met Asp Gly Tyr Phe His His Glu Ala Ser Ile Glu Gly Gly Gln
690                 695                 700

His Leu Asn Val Asn Val Met Asn Arg Glu Met Leu Leu Asp Ala Met
705                 710                 715                 720

Glu Asn Pro Glu Lys Tyr Pro Gln Leu Thr Ile Arg Val Ser Gly Tyr
                725                 730                 735

Ala Val Arg Phe Asn Ser Leu Thr Lys Glu Gln Gln Gln Asp Val Ile
            740                 745                 750

Thr Arg Thr Phe Thr Gln Ser Met
            755                 760

<210> SEQ ID NO 19
<211> LENGTH: 741
<212> TYPE: DNA
<213> ORGANISM: Escherichia coli

<400> SEQUENCE: 19
atgtcagtta ttggtcgcat tcactccttt gaatcctgtg gaaccgtaga cggcccaggt    60
attcgcttta tcaccttttt ccagggctgc ctgatgcgct gcctgtattg tcataaccgc   120
gacacctggg acacgcatgg cggtaaagaa gttaccgttg aagatttgat gaaggaagtg   180
gtgacctatc gccactttat gaacgcttcc ggcggcggcg ttaccgcatc cggcggtgaa   240
gcaatcctgc aagctgagtt tgttcgtgac tggttccgcg cctgcaaaaa agaaggcatt   300
catacctgtc tggacaccaa cggttttgtt cgtcgttacg atccggtgat tgatgaactg   360
ctggaagtaa ccgacctggt aatgctcgat ctcaaacaga tgaacgacga gatccaccaa   420
aatctggttg gagtttccaa ccaccgcacg ctggagttcg ctaaatatct ggcgaacaaa   480
aatgtgaagg tgtggatccg ctacgttgtt gtcccaggct ggtctgacga tgacgattca   540
gcgcatcgcc tcggtgaatt tacccgtgat atgggcaacg ttgagaaaat cgagcttctc   600
ccctaccacg agctgggcaa acacaaatgg gtggcaatgg gtgaagagta caaactcgac   660
ggtgttaaac caccgaagaa agagaccatg aacgcgtga aaggcattct tgagcagtac   720
ggtcataagg taatgttcta a                                             741

<210> SEQ ID NO 20
<211> LENGTH: 246
<212> TYPE: PRT
<213> ORGANISM: Escherichia coli

<400> SEQUENCE: 20

Met Ser Val Ile Gly Arg Ile His Ser Phe Glu Ser Cys Gly Thr Val
1               5                   10                  15

Asp Gly Pro Gly Ile Arg Phe Ile Thr Phe Phe Gln Gly Cys Leu Met
            20                  25                  30

Arg Cys Leu Tyr Cys His Asn Arg Asp Thr Trp Asp Thr His Gly Gly
        35                  40                  45

Lys Glu Val Thr Val Glu Asp Leu Met Lys Glu Val Val Thr Tyr Arg

```
            50                   55                   60
His Phe Met Asn Ala Ser Gly Gly Val Thr Ala Ser Gly Glu
 65                   70                   75                   80

Ala Ile Leu Gln Ala Glu Phe Val Arg Asp Trp Phe Arg Ala Cys Lys
                 85                   90                   95

Lys Glu Gly Ile His Thr Cys Leu Asp Thr Asn Gly Phe Val Arg Arg
            100                  105                  110

Tyr Asp Pro Val Ile Asp Glu Leu Leu Glu Val Thr Asp Leu Val Met
        115                  120                  125

Leu Asp Leu Lys Gln Met Asn Asp Glu Ile His Gln Asn Leu Val Gly
    130                  135                  140

Val Ser Asn His Arg Thr Leu Glu Phe Ala Lys Tyr Leu Ala Asn Lys
145                  150                  155                  160

Asn Val Lys Val Trp Ile Arg Tyr Val Val Pro Gly Trp Ser Asp
                165                  170                  175

Asp Asp Asp Ser Ala His Arg Leu Gly Glu Phe Thr Arg Asp Met Gly
            180                  185                  190

Asn Val Glu Lys Ile Glu Leu Leu Pro Tyr His Glu Leu Gly Lys His
        195                  200                  205

Lys Trp Val Ala Met Gly Glu Tyr Lys Leu Asp Gly Val Lys Pro
    210                  215                  220

Pro Lys Lys Glu Thr Met Glu Arg Val Lys Gly Ile Leu Glu Gln Tyr
225                  230                  235                  240

Gly His Lys Val Met Phe
                245

<210> SEQ ID NO 21
<211> LENGTH: 1809
<212> TYPE: DNA
<213> ORGANISM: Escherichia coli

<400> SEQUENCE: 21
gtgcaaacct tcaagccga tcttgccatt gtaggcgccg gtggcgcggg attacgtgct      60
gcaattgctg ccgcgcaggc aaatccgaat gcaaaaatcg cactaatctc aaaagtatac     120
ccgatgcgta gccataccgt tgctgcagaa gggggctccg ccgctgtcgc gcaggatcat     180
gacagcttcg aatatcactt tcacgataca gtagcgggtg gcgactggtt gtgtgagcag     240
gatgtcgtgg attatttcgt ccaccactgc ccaaccgaaa tgacccaact ggaactgtgg     300
ggatgcccat ggagccgtcg cccggatggt agcgtcaacg tacgtcgctt cggcggcatg     360
aaaatcgagc gcacctggtt cgccgccgat aagaccggct tccatatgct gcacacgctg     420
ttccagacct ctctgcaatt cccgcagatc cagcgttttg acgaacattt cgtgctggat     480
attctggttg atgatggtca tgttcgcggc ctggtagcaa tgaacatgat ggaaggcacg     540
ctggtgcaga tccgtgctaa cgcggtcgtt atggctactg cggtgcgggt cgcgtttat     600 cgttacaaca ccaacggcgg catcgttacc ggtgacggta tgggtatggc gctaagccac     660
ggcgttccgc tgcgtgacat ggaattcgtt cagtatcacc caaccggtct gccaggttcc     720
ggtatcctga tgaccgaagg ttgccgcggt gaaggcggta ttctggtcaa caaaaatggc     780
taccgttatc tgcaagatta cggcatgggc ccggaaactc gctgggcga gccgaaaaac     840 aaatatatgg aactgggtcc acgcgacaaa gtctctcagg ccttctggca cgaatggcgt     900
aaaggcaaca ccatctccac gccgcgtggc gatgtggttt atctcgactt gcgtcacctc     960
ggcgagaaaa aactgcatga acgtctgccg ttcatctgcg aactggcgaa agcgtacgtt    1020
```

-continued

```
ggcgtcgatc cggttaaaga accgattccg gtacgtccga ccgcacacta caccatgggc    1080
ggtatcgaaa ccgatcagaa ctgtgaaacc cgcattaaag gtctgttcgc cgtgggtgaa    1140
tgttcctctg ttggtctgca cggtgcaaac cgtctgggtt ctaactccct ggcggaactg    1200
gtggtcttcg gccgtctggc cggtgaacaa gcgacagagc gtgcagcaac tgccggtaat    1260
ggcaacgaag cggcaattga agcgcaggca gctggcgttg aacaacgtct gaaagatctg    1320
gttaaccagg atggcggcga aaactggggcg aagatccgcg acgaaatggg cctggctatg    1380
gaagaaggct gcggtatcta ccgtacgccg gaactgatgc agaaaaccat cgacaagctg    1440
gcagagctgc aggaacgctt caagcgcgtg cgcatcaccg acacttccag cgtgttcaac    1500
accgacctgc tctacaccat tgaactgggc cacggtctga cgttgctga atgtatggcg    1560 cactccgcaa tggcacgtaa agagtcccgc ggcgcgcacc agcgtctgga cgaaggttgc    1620
accgagcgtg acgacgtcaa cttcctcaaa cacaccctcg ccttccgcga tgctgatggc    1680
acgactcgcc tggagtacag cgacgtgaag attactacgc tgccgccagc taaacgcgtt    1740
tacggtggcg aagcggatgc agccgataag gcggaagcag ccaataagaa ggagaaggcg    1800
aatggctga                                                            1809
```

<210> SEQ ID NO 22
<211> LENGTH: 602
<212> TYPE: PRT
<213> ORGANISM: Escherichia coli

<400> SEQUENCE: 22

```
Met Gln Thr Phe Gln Ala Asp Leu Ala Ile Val Gly Ala Gly Gly Ala
1               5                   10                  15

Gly Leu Arg Ala Ala Ile Ala Ala Ala Gln Ala Asn Pro Asn Ala Lys
            20                  25                  30

Ile Ala Leu Ile Ser Lys Val Tyr Pro Met Arg Ser His Thr Val Ala
        35                  40                  45

Ala Glu Gly Gly Ser Ala Ala Val Ala Gln Asp His Asp Ser Phe Glu
    50                  55                  60

Tyr His Phe His Asp Thr Val Ala Gly Gly Asp Trp Leu Cys Glu Gln
65                  70                  75                  80

Asp Val Val Asp Tyr Phe Val His His Cys Pro Thr Glu Met Thr Gln
                85                  90                  95

Leu Glu Leu Trp Gly Cys Pro Trp Ser Arg Arg Pro Asp Gly Ser Val
            100                 105                 110

Asn Val Arg Arg Phe Gly Gly Met Lys Ile Glu Arg Thr Trp Phe Ala
        115                 120                 125

Ala Asp Lys Thr Gly Phe His Met Leu His Thr Leu Phe Gln Thr Ser
    130                 135                 140

Leu Gln Phe Pro Gln Ile Gln Arg Phe Asp Glu His Phe Val Leu Asp
145                 150                 155                 160

Ile Leu Val Asp Asp Gly His Val Arg Gly Leu Val Ala Met Asn Met
                165                 170                 175

Met Glu Gly Thr Leu Val Gln Ile Arg Ala Asn Ala Val Val Met Ala
            180                 185                 190

Thr Gly Gly Ala Gly Arg Val Tyr Arg Tyr Asn Thr Asn Gly Gly Ile
        195                 200                 205

Val Thr Gly Asp Gly Met Gly Met Ala Leu Ser His Gly Val Pro Leu
    210                 215                 220
```

Arg Asp Met Glu Phe Val Gln Tyr His Pro Thr Gly Leu Pro Gly Ser
225                 230                 235                 240

Gly Ile Leu Met Thr Glu Gly Cys Arg Gly Glu Gly Gly Ile Leu Val
            245                 250                 255

Asn Lys Asn Gly Tyr Arg Tyr Leu Gln Asp Tyr Gly Met Gly Pro Glu
        260                 265                 270

Thr Pro Leu Gly Glu Pro Lys Asn Lys Tyr Met Glu Leu Gly Pro Arg
    275                 280                 285

Asp Lys Val Ser Gln Ala Phe Trp His Glu Trp Arg Lys Gly Asn Thr
290                 295                 300

Ile Ser Thr Pro Arg Gly Asp Val Val Tyr Leu Asp Leu Arg His Leu
305                 310                 315                 320

Gly Glu Lys Lys Leu His Glu Arg Leu Pro Phe Ile Cys Glu Leu Ala
            325                 330                 335

Lys Ala Tyr Val Gly Val Asp Pro Val Lys Glu Pro Ile Pro Val Arg
        340                 345                 350

Pro Thr Ala His Tyr Thr Met Gly Gly Ile Glu Thr Asp Gln Asn Cys
    355                 360                 365

Glu Thr Arg Ile Lys Gly Leu Phe Ala Val Gly Glu Cys Ser Ser Val
370                 375                 380

Gly Leu His Gly Ala Asn Arg Leu Gly Ser Asn Ser Leu Ala Glu Leu
385                 390                 395                 400

Val Val Phe Gly Arg Leu Ala Gly Glu Gln Ala Thr Glu Arg Ala Ala
            405                 410                 415

Thr Ala Gly Asn Gly Asn Glu Ala Ala Ile Glu Ala Gln Ala Ala Gly
        420                 425                 430

Val Glu Gln Arg Leu Lys Asp Leu Val Asn Gln Asp Gly Gly Glu Asn
    435                 440                 445

Trp Ala Lys Ile Arg Asp Glu Met Gly Leu Ala Met Glu Glu Gly Cys
450                 455                 460

Gly Ile Tyr Arg Thr Pro Glu Leu Met Gln Lys Thr Ile Asp Lys Leu
465                 470                 475                 480

Ala Glu Leu Gln Glu Arg Phe Lys Arg Val Arg Ile Thr Asp Thr Ser
            485                 490                 495

Ser Val Phe Asn Thr Asp Leu Leu Tyr Thr Ile Glu Leu Gly His Gly
        500                 505                 510

Leu Asn Val Ala Glu Cys Met Ala His Ser Ala Met Ala Arg Lys Glu
    515                 520                 525

Ser Arg Gly Ala His Gln Arg Leu Asp Glu Gly Cys Thr Glu Arg Asp
530                 535                 540

Asp Val Asn Phe Leu Lys His Thr Leu Ala Phe Arg Asp Ala Asp Gly
545                 550                 555                 560

Thr Thr Arg Leu Glu Tyr Ser Asp Val Lys Ile Thr Thr Leu Pro Pro
            565                 570                 575

Ala Lys Arg Val Tyr Gly Gly Glu Ala Asp Ala Ala Asp Lys Ala Glu
        580                 585                 590

Ala Ala Asn Lys Lys Glu Lys Ala Asn Gly
    595                 600

<210> SEQ ID NO 23
<211> LENGTH: 735
<212> TYPE: DNA
<213> ORGANISM: Escherichia coli

<400> SEQUENCE: 23

```
atggctgaga tgaaaaacct gaaaattgag gtggtgcgct ataacccgga agtcgatacc    60
gcaccgcata gcgcattcta tgaagtgcct tatgacgcaa ctacctcatt actggatgcg   120
ctgggctaca tcaaagacaa cctggcaccg gacctgagct accgctggtc ctgccgtatg   180
gcgatttgtg gttcctgcgg catgatggtt aacaacgtgc caaaactggc atgtaaaacc   240
ttcctgcgtg attacaccga cggtatgaag gttgaagcgt tagctaactt cccgattgaa   300
cgcgatctgg tggtcgatat gacccacttc atcgaaagtc tggaagcgat caaaccgtac   360
atcatcggca actcccgcac cgcggatcag ggtactaaca tccagacccc ggcgcagatg   420
gcgaagtatc accagttctc cggttgcatc aactgtggtt tgtgctacgc cgcgtgcccg   480
cagtttggcc tgaacccaga gttcatcggt ccggctgcca ttacgctggc catcgttat   540 aacgaagata gccgcgacca cggtaagaag gagcgtatgg cgcagttgaa cagccagaac   600
ggcgtatgga gctgtacttt cgtgggctac tgctccgaag tctgcccgaa acacgtcgat   660
ccggctgcgg ccattcagca gggcaaagta gaaagttcga agactttctc tatcgcgacc   720
ctgaaaccac gctaa                                                    735
```

<210> SEQ ID NO 24
<211> LENGTH: 244
<212> TYPE: PRT
<213> ORGANISM: Escherichia coli

<400> SEQUENCE: 24

```
Met Ala Glu Met Lys Asn Leu Lys Ile Glu Val Val Arg Tyr Asn Pro
1               5                   10                  15

Glu Val Asp Thr Ala Pro His Ser Ala Phe Tyr Glu Val Pro Tyr Asp
                20                  25                  30

Ala Thr Thr Ser Leu Leu Asp Ala Leu Gly Tyr Ile Lys Asp Asn Leu
            35                  40                  45

Ala Pro Asp Leu Ser Tyr Arg Trp Ser Cys Arg Met Ala Ile Cys Gly
        50                  55                  60

Ser Cys Gly Met Met Val Asn Asn Val Pro Lys Leu Ala Cys Lys Thr
65                  70                  75                  80

Phe Leu Arg Asp Tyr Thr Asp Gly Met Lys Val Glu Ala Leu Ala Asn
                85                  90                  95

Phe Pro Ile Glu Arg Asp Leu Val Val Asp Met Thr His Phe Ile Glu
            100                 105                 110

Ser Leu Glu Ala Ile Lys Pro Tyr Ile Ile Gly Asn Ser Arg Thr Ala
        115                 120                 125

Asp Gln Gly Thr Asn Ile Gln Thr Pro Ala Gln Met Ala Lys Tyr His
    130                 135                 140

Gln Phe Ser Gly Cys Ile Asn Cys Gly Leu Cys Tyr Ala Ala Cys Pro
145                 150                 155                 160

Gln Phe Gly Leu Asn Pro Glu Phe Ile Gly Pro Ala Ala Ile Thr Leu
                165                 170                 175

Ala His Arg Tyr Asn Glu Asp Ser Arg Asp His Gly Lys Lys Glu Arg
            180                 185                 190

Met Ala Gln Leu Asn Ser Gln Asn Gly Val Trp Ser Cys Thr Phe Val
        195                 200                 205

Gly Tyr Cys Ser Glu Val Cys Pro Lys His Val Asp Pro Ala Ala Ala
    210                 215                 220

Ile Gln Gln Gly Lys Val Glu Ser Ser Lys Asp Phe Leu Ile Ala Thr
225                 230                 235                 240
```

<210> SEQ ID NO 25
<211> LENGTH: 396
<212> TYPE: DNA
<213> ORGANISM: Escherichia coli

<400> SEQUENCE: 25

```
atgacgacta aacgtaaacc gtatgtacgg ccaatgacgt ccacctggtg gaaaaaattg      60
ccgttttatc gcttttacat gctgcgcgaa ggcacggcgg ttccggctgt gtggttcagc     120
attgaactga ttttcgggct gtttgccctg aaaaatggcc cggaagcctg ggcgggattc     180
gtcgactttt tacaaaaccc ggttatcgtg atcattaacc tgatcactct ggcggcagct     240
ctgctgcaca ccaaaacctg gtttgaactg caccgaaag cggccaatat cattgtaaaa      300
gacgaaaaaa tgggaccaga gccaattatc aaaagtctct gggcggtaac tgtggttgcc     360
accatcgtaa tcctgtttgt tgccctgtac tggtaa                              396
```

<210> SEQ ID NO 26
<211> LENGTH: 131
<212> TYPE: PRT
<213> ORGANISM: Escherichia coli

<400> SEQUENCE: 26

```
Met Thr Thr Lys Arg Lys Pro Tyr Val Arg Pro Met Thr Ser Thr Trp
  1               5                  10                  15
Trp Lys Lys Leu Pro Phe Tyr Arg Phe Tyr Met Leu Arg Glu Gly Thr
             20                  25                  30
Ala Val Pro Ala Val Trp Phe Ser Ile Glu Leu Ile Phe Gly Leu Phe
         35                  40                  45
Ala Leu Lys Asn Gly Pro Glu Ala Trp Ala Gly Phe Val Asp Phe Leu
     50                  55                  60
Gln Asn Pro Val Ile Val Ile Asn Leu Ile Thr Leu Ala Ala Ala
 65                  70                  75                  80
Leu Leu His Thr Lys Thr Trp Phe Glu Leu Ala Pro Lys Ala Ala Asn
                 85                  90                  95
Ile Ile Val Lys Asp Glu Lys Met Gly Pro Glu Pro Ile Ile Lys Ser
            100                 105                 110
Leu Trp Ala Val Thr Val Val Ala Thr Ile Val Ile Leu Phe Val Ala
        115                 120                 125
Leu Tyr Trp
    130
```

<210> SEQ ID NO 27
<211> LENGTH: 360
<212> TYPE: DNA
<213> ORGANISM: Escherichia coli

<400> SEQUENCE: 27

```
atgattaatc caaatccaaa gcgttctgac gaaccggtat tctggggcct cttcggggcc      60
ggtggtatgt ggagcgccat cattgcgccg gtgatgatcc tgctggtggg tattctgctg     120
ccactggggt tgtttccggg tgatgcgctg agctacgagc gcgttctggc gttcgcgcag     180
agcttcattg gtcgcgtatt cctgttcctg atgatcgttc tgccgctgtg gtgtggttta     240
caccgtatgc accacgcgat gcacgatctg aaaatccacg tacctgcggg caatggggtt     300
ttctacggtc tggctgctat cctgacagtt gtcacgctga ttggtgtcgt tacaatctaa     360
```

<210> SEQ ID NO 28
<211> LENGTH: 119
<212> TYPE: PRT
<213> ORGANISM: Escherichia coli

<400> SEQUENCE: 28

```
Met Ile Asn Pro Asn Pro Lys Arg Ser Asp Glu Pro Val Phe Trp Gly
1               5                   10                  15

Leu Phe Gly Ala Gly Gly Met Trp Ser Ala Ile Ala Pro Val Met
            20                  25                  30

Ile Leu Leu Val Gly Ile Leu Leu Pro Leu Gly Leu Phe Pro Gly Asp
        35                  40                  45

Ala Leu Ser Tyr Glu Arg Val Leu Ala Phe Ala Gln Ser Phe Ile Gly
    50                  55                  60

Arg Val Phe Leu Phe Leu Met Ile Val Leu Pro Leu Trp Cys Gly Leu
65                  70                  75                  80

His Arg Met His His Ala Met His Asp Leu Lys Ile His Val Pro Ala
                85                  90                  95

Gly Lys Trp Val Phe Tyr Gly Leu Ala Ala Ile Leu Thr Val Val Thr
            100                 105                 110

Leu Ile Gly Val Val Thr Ile
        115
```

<210> SEQ ID NO 29
<211> LENGTH: 1812
<212> TYPE: DNA
<213> ORGANISM: Escherichia coli

<400> SEQUENCE: 29

```
atgaatccac aattgttacg cgtaacaaat cgaatcattg aacgttcgcg cgagactcgc      60
tctgcttatc tcgcccggat agaacaagcg aaaacttcga ccgttcatcg ttcgcagttg     120
gcatgcggta acctggcaca cggtttcgct gcctgccagc cagaagacaa agcctctttg     180
aaaagcatgt tgcgtaacaa tatcgccatc atcacctcct ataacgacat gctctccgcg     240
caccagcctt atgaacacta tccagaaatc attcgtaaag ccctgcatga agcgaatgcg     300
gttggtcagg ttgcgggcgg tgttccggcg atgtgtgatg gtgtcaccca ggggcaggat     360
ggaatggaat tgtcgctgct aagccgcgaa gtgatagcga tgtctgcggc ggtgggctg     420 tcccataaca tgtttgatgg tgctctgttc ctcggtgtgt cgacaagat tgtcccgggt     480 ctgacgatgg cagccctgtc gtttggtcat ttgcctgcgg tgtttgtgcc gtctggaccg     540
atggcaagcg gtttgccaaa taagaaaaa gtgcgtattc gccagcttta tgccgaaggt     600
aaagtggacc gcatggcctt actggagtca gaagccgcgt cttaccatgc gccgggaaca     660
tgtactttct acggtactgc caacaccaac cagatggtgg tggagtttat ggggatgcag     720
ttgccaggct cttcttttgt tcatccggat tctccgctgc gcgatgcttt gaccgccgca     780
gctgcgcgtc aggttacacg catgaccggt aatggtaatg aatggatgcc gatcggtaag     840
atgatcgatg agaaagtggt ggtgaacggt atcgttgcac tgctggcgac cggtggttcc     900
actaaccaca ccatgcacct ggtggcgatg gcgcgcgcgg ccgtattca gattaactgg     960 gatgacttct ctgacctttc tgatgttgta ccgctgatgg cacgtctcta cccgaacggt    1020
ccggccgata ttaaccactt ccaggcggca ggtggcgtac cggttctggt cgtgaactg    1080 ctcaaagcag gcctgctgca tgaagatgtc aatacggtgg caggttttgg tctgtctcgt    1140
```

```
tataccettg aaccatggct gaataatggt gaactggact ggcgggaagg ggcggaaaaa    1200
tcactcgaca gcaatgtgat cgcttccttc gaacaacctt tctctcatca tggtgggaca    1260
aaagtgttaa gcggtaacct gggccgtgcg gttatgaaaa cctctgccgt gccggttgag    1320
aaccaggtga ttgaagcgcc agcggttgtt tttgaaagcc agcatgacgt tatgccggcc    1380
tttgaagcgg gtttgctgga ccgcgattgt gtcgttgttg tccgtcatca ggggccaaaa    1440
gcgaacggaa tgccagaatt acataaactc atgccgccac ttggtgtatt attggaccgg    1500
tgtttcaaaa ttgcgttagt taccgatgga cgactctccg gcgcttcagg taaagtgccg    1560
tcagctatcc acgtaacacc agaagcctac gatggcgggc tgctggcaaa agtgcgcgac    1620
ggggacatca ttcgtgtgaa tggacagaca ggcgaactga cgctgctggt agacgaagcg    1680
gaactggctg ctcgcgaacc gcacattcct gacctgagcg cgtcacgcgt gggaacagga    1740
cgtgaattat tcagcgcctt gcgtgaaaaa ctgtccggtg ccgaacaggg cgcaacctgt    1800
atcacttttt aa                                                       1812
```

<210> SEQ ID NO 30
<211> LENGTH: 603
<212> TYPE: PRT
<213> ORGANISM: Escherichia coli

<400> SEQUENCE: 30

```
Met Asn Pro Gln Leu Leu Arg Val Thr Asn Arg Ile Ile Glu Arg Ser
1               5                   10                  15

Arg Glu Thr Arg Ser Ala Tyr Leu Ala Arg Ile Glu Gln Ala Lys Thr
            20                  25                  30

Ser Thr Val His Arg Ser Gln Leu Ala Cys Gly Asn Leu Ala His Gly
        35                  40                  45

Phe Ala Ala Cys Gln Pro Glu Asp Lys Ala Ser Leu Lys Ser Met Leu
    50                  55                  60

Arg Asn Asn Ile Ala Ile Ile Thr Ser Tyr Asn Asp Met Leu Ser Ala
65                  70                  75                  80

His Gln Pro Tyr Glu His Tyr Pro Glu Ile Ile Arg Lys Ala Leu His
                85                  90                  95

Glu Ala Asn Ala Val Gly Gln Val Ala Gly Val Pro Ala Met Cys
            100                 105                 110

Asp Gly Val Thr Gln Gly Gln Asp Gly Met Glu Leu Ser Leu Ser
        115                 120                 125

Arg Glu Val Ile Ala Met Ser Ala Ala Val Gly Leu Ser His Asn Met
130                 135                 140

Phe Asp Gly Ala Leu Phe Leu Gly Val Cys Asp Lys Ile Val Pro Gly
145                 150                 155                 160

Leu Thr Met Ala Ala Leu Ser Phe Gly His Leu Pro Ala Val Phe Val
                165                 170                 175

Pro Ser Gly Pro Met Ala Ser Gly Leu Pro Asn Lys Glu Lys Val Arg
            180                 185                 190

Ile Arg Gln Leu Tyr Ala Glu Gly Lys Val Asp Arg Met Ala Leu Leu
        195                 200                 205

Glu Ser Glu Ala Ala Ser Tyr His Ala Pro Gly Thr Cys Thr Phe Tyr
    210                 215                 220

Gly Thr Ala Asn Thr Asn Gln Met Val Val Glu Phe Met Gly Met Gln
225                 230                 235                 240

Leu Pro Gly Ser Ser Phe Val His Pro Asp Ser Pro Leu Arg Asp Ala
                245                 250                 255
```

Leu Thr Ala Ala Ala Ala Arg Gln Val Thr Arg Met Thr Gly Asn Gly
        260                 265                 270

Asn Glu Trp Met Pro Ile Gly Lys Met Ile Asp Glu Lys Val Val
        275                 280                 285

Asn Gly Ile Val Ala Leu Leu Ala Thr Gly Gly Ser Thr Asn His Thr
290                 295                 300

Met His Leu Val Ala Met Ala Arg Ala Ala Gly Ile Gln Ile Asn Trp
305                 310                 315                 320

Asp Asp Phe Ser Asp Leu Ser Asp Val Val Pro Leu Met Ala Arg Leu
                325                 330                 335

Tyr Pro Asn Gly Pro Ala Asp Ile Asn His Phe Gln Ala Ala Gly Gly
            340                 345                 350

Val Pro Val Leu Val Arg Glu Leu Leu Lys Ala Gly Leu Leu His Glu
        355                 360                 365

Asp Val Asn Thr Val Ala Gly Phe Gly Leu Ser Arg Tyr Thr Leu Glu
370                 375                 380

Pro Trp Leu Asn Asn Gly Glu Leu Asp Trp Arg Glu Gly Ala Glu Lys
385                 390                 395                 400

Ser Leu Asp Ser Asn Val Ile Ala Ser Phe Glu Gln Pro Phe Ser His
                405                 410                 415

His Gly Gly Thr Lys Val Leu Ser Gly Asn Leu Gly Arg Ala Val Met
            420                 425                 430

Lys Thr Ser Ala Val Pro Val Glu Asn Gln Val Ile Glu Ala Pro Ala
        435                 440                 445

Val Val Phe Glu Ser Gln His Asp Val Met Pro Ala Phe Glu Ala Gly
        450                 455                 460

Leu Leu Asp Arg Asp Cys Val Val Val Arg His Gln Gly Pro Lys
465                 470                 475                 480

Ala Asn Gly Met Pro Glu Leu His Lys Leu Met Pro Pro Leu Gly Val
                485                 490                 495

Leu Leu Asp Arg Cys Phe Lys Ile Ala Leu Val Thr Asp Gly Arg Leu
            500                 505                 510

Ser Gly Ala Ser Gly Lys Val Pro Ser Ala Ile His Val Thr Pro Glu
        515                 520                 525

Ala Tyr Asp Gly Gly Leu Leu Ala Lys Val Arg Asp Gly Asp Ile Ile
        530                 535                 540

Arg Val Asn Gly Gln Thr Gly Glu Leu Thr Leu Leu Val Asp Glu Ala
545                 550                 555                 560

Glu Leu Ala Ala Arg Glu Pro His Ile Pro Asp Leu Ser Ala Ser Arg
                565                 570                 575

Val Gly Thr Gly Arg Glu Leu Phe Ser Ala Leu Arg Glu Lys Leu Ser
            580                 585                 590

Gly Ala Glu Gln Gly Ala Thr Cys Ile Thr Phe
        595                 600

<210> SEQ ID NO 31
<211> LENGTH: 642
<212> TYPE: DNA
<213> ORGANISM: Escherichia coli

<400> SEQUENCE: 31
atgaaaaact ggaaaacaag tgcagaatca atcctgacca ccggcccggt tgtaccggtt     60
atcgtggtaa aaaaactgga acacgcggtg ccgatggcaa aagcgttggt tgctggtggg    120

-continued

```
gtgcgcgttc tggaagtgac tctgcgtacc gagtgtgcag ttgacgctat ccgtgctatc      180
gccaaagaag tgcctgaagc gattgtgggt gccggtacgg tgctgaatcc acagcagctg      240
gcagaagtca ctgaagcggg tgcacagttc gcaattagcc cgggtctgac cgagccgctg      300
ctgaaagctg ctaccgaagg gactattcct ctgattccgg ggatcagcac tgtttccgaa      360
ctgatgctgg gtatggacta cggtttgaaa gagttcaaat tcttcccggc tgaagctaac      420
ggcggcgtga aagccctgca ggcgatcgcg ggtccgttct cccaggtccg tttctgcccg      480
acgggtggta tttctccggc taactaccgt gactacctgg cgctgaaaag cgtgctgtgc      540
atcggtggtt cctggctggt tccggcagat gcgctggaag cgggcgatta cgaccgcatt      600
actaagctgg cgcgtgaagc tgtagaaggc gctaagctgt aa                         642
```

<210> SEQ ID NO 32
<211> LENGTH: 213
<212> TYPE: PRT
<213> ORGANISM: Escherichia coli

<400> SEQUENCE: 32

```
Met Lys Asn Trp Lys Thr Ser Ala Glu Ser Ile Leu Thr Thr Gly Pro
1               5                   10                  15

Val Val Pro Val Ile Val Lys Lys Leu Glu His Ala Val Pro Met
            20                  25                  30

Ala Lys Ala Leu Val Ala Gly Gly Val Arg Val Leu Glu Val Thr Leu
        35                  40                  45

Arg Thr Glu Cys Ala Val Asp Ala Ile Arg Ala Ile Ala Lys Glu Val
    50                  55                  60

Pro Glu Ala Ile Val Gly Ala Gly Thr Val Leu Asn Pro Gln Gln Leu
65                  70                  75                  80

Ala Glu Val Thr Glu Ala Gly Ala Gln Phe Ala Ile Ser Pro Gly Leu
                85                  90                  95

Thr Glu Pro Leu Leu Lys Ala Ala Thr Glu Gly Thr Ile Pro Leu Ile
            100                 105                 110

Pro Gly Ile Ser Thr Val Ser Glu Leu Met Leu Gly Met Asp Tyr Gly
        115                 120                 125

Leu Lys Glu Phe Lys Phe Phe Pro Ala Glu Ala Asn Gly Gly Val Lys
    130                 135                 140

Ala Leu Gln Ala Ile Ala Gly Pro Phe Ser Gln Val Arg Phe Cys Pro
145                 150                 155                 160

Thr Gly Gly Ile Ser Pro Ala Asn Tyr Arg Asp Tyr Leu Ala Leu Lys
                165                 170                 175

Ser Val Leu Cys Ile Gly Gly Ser Trp Leu Val Pro Ala Asp Ala Leu
            180                 185                 190

Glu Ala Gly Asp Tyr Asp Arg Ile Thr Lys Leu Ala Arg Glu Ala Val
        195                 200                 205

Glu Gly Ala Lys Leu
    210
```

<210> SEQ ID NO 33
<211> LENGTH: 1707
<212> TYPE: DNA
<213> ORGANISM: Zymomonas mobilis
<220> FEATURE:
<221> NAME/KEY: misc_feature
<222> LOCATION: (622)..(622)
<223> OTHER INFORMATION: n is a, c, g, or t

<400> SEQUENCE: 33

-continued

```
atgagttata ctgtcggtac ctatttagcg gagcggcttg tccagattgg tctcaagcat    60
cacttcgcag tcgcgggcga ctacaacctc gtccttcttg acaacctgct tttgaacaaa   120
aacatggagc aggtttattg ctgtaacgaa ctgaactgcg gtttcagtgc agaaggttat   180
gctcgtgcca aggcgcagc agcagccgtc gttacctaca cgtcggtgc gctttccgca    240
tttgatgcta tcggtggcgc ctatgcagaa accttccgg ttatcctgat ctccggtgct    300
ccgaacaaca atgaccacgc tgctggtcac gtgttcatc acgctcttgg caaaaccgac    360
tatcactatc agttggaaat ggccaagaac atcacggccg ccgctgaagc gatttatacc    420
ccggaagaag ctccggctaa aatcgatcac gtgattaaaa ctgctcttcg tgagaagaag    480
ccggtttatc tcgaaatcgc ttgcaacatt gcttccatgc cctgcgccgc tcctggaccg    540
gcaagcgcat tgttcaatga cgaagccagc gacgaagctt ctttgaatgc agcggttgaa    600
gaaaccctga aattcatcgc cnaccgcgac aaagttgccg tcctcgtcgg cagcaagctg    660
cgcgcagctg gtgctgaaga agctgctgtc aaatttgctg atgctcttgg tggcgcagtt    720
gctaccatgg ctgctgcaaa aagcttcttc ccagaagaaa acccgcatta catcggtacc    780
tcatggggtg aagtcagcta tccgggcgtt gaaaagacga tgaaagaagc cgatgcggtt    840
atcgctctgg ctcctgtctt taacgactac tccaccactg gttggacgga tattcctgat    900
cctaagaaac tggttctcgc tgaaccgcgt tctgtcgtcg ttaacggcat tcgcttcccc    960
agcgtccatc tgaaagacta tctgacccgt ttggctcaga agtttccaa gaaaaccggt   1020
gctttggact tcttcaaatc cctcaatgca ggtgaactga agaaagccgc tccggctgat   1080
ccgagtgctc cgttggtcaa cgcagaaatc gcccgtcagg tcgaagctct tctgaccccg   1140
aacacgacgg ttattgctga aaccggtgac tcttggttca atgctcagcg catgaagctc   1200
ccgaacggtg ctcgcgttga atatgaaatg cagtggggtc acattggttg gtccgttcct   1260
gccgccttcg gttatgccgt cggtgctccg gaacgtcgca acatcctcat ggttggtgat   1320
ggttccttcc agctgacggc tcaggaagtc gctcagatgg ttcgcctgaa actgccggtt   1380
atcatcttct tgatcaataa ctatggttac accatcgaag ttatgatcca tgatggtccg   1440
tacaacaaca tcaagaactg ggattatgcc ggtctgatgg aagtgttcaa cggtaacggt   1500
ggttatgaca gcggtgctgg taaaggcctg aaggctaaaa ccggtggcga actggcagaa   1560
gctatcaagg ttgctctggc aaacaccgac ggcccaaccc tgatcgaatg cttcatcggt   1620
cgtgaagact gcactgaaga attggtcaaa tggggtaagc gcgttgctgc cgccaacagc   1680
cgtaagcctg ttaacaagct cctctag                                       1707
```

<210> SEQ ID NO 34
<211> LENGTH: 568
<212> TYPE: PRT
<213> ORGANISM: Zymomonas mobilis
<220> FEATURE:
<221> NAME/KEY: misc_feature
<222> LOCATION: (208)..(208)
<223> OTHER INFORMATION: Xaa can be any naturally occurring amino acid

<400> SEQUENCE: 34

Met Ser Tyr Thr Val Gly Thr Tyr Leu Ala Glu Arg Leu Val Gln Ile
1               5                   10                  15

Gly Leu Lys His His Phe Ala Val Ala Gly Asp Tyr Asn Leu Val Leu
                20                  25                  30

Leu Asp Asn Leu Leu Leu Asn Lys Asn Met Glu Gln Val Tyr Cys Cys
        35                  40                  45

```
Asn Glu Leu Asn Cys Gly Phe Ser Ala Glu Gly Tyr Ala Arg Ala Lys
         50                  55                  60
Gly Ala Ala Ala Ala Val Val Thr Tyr Ser Val Gly Ala Leu Ser Ala
 65                  70                  75                  80
Phe Asp Ala Ile Gly Gly Ala Tyr Ala Glu Asn Leu Pro Val Ile Leu
                 85                  90                  95
Ile Ser Gly Ala Pro Asn Asn Asn Asp His Ala Ala Gly His Val Leu
            100                 105                 110
His His Ala Leu Gly Lys Thr Asp Tyr His Tyr Gln Leu Glu Met Ala
        115                 120                 125
Lys Asn Ile Thr Ala Ala Glu Ala Ile Tyr Thr Pro Glu Glu Ala
130                 135                 140
Pro Ala Lys Ile Asp His Val Ile Lys Thr Ala Leu Arg Glu Lys Lys
145                 150                 155                 160
Pro Val Tyr Leu Glu Ile Ala Cys Asn Ile Ala Ser Met Pro Cys Ala
                165                 170                 175
Ala Pro Gly Pro Ala Ser Ala Leu Phe Asn Asp Glu Ala Ser Asp Glu
            180                 185                 190
Ala Ser Leu Asn Ala Ala Val Glu Glu Thr Leu Lys Phe Ile Ala Xaa
        195                 200                 205
Arg Asp Lys Val Ala Val Leu Val Gly Ser Lys Leu Arg Ala Ala Gly
210                 215                 220
Ala Glu Glu Ala Ala Val Lys Phe Ala Asp Ala Leu Gly Gly Ala Val
225                 230                 235                 240
Ala Thr Met Ala Ala Lys Ser Phe Phe Pro Glu Glu Asn Pro His
                245                 250                 255
Tyr Ile Gly Thr Ser Trp Gly Glu Val Ser Tyr Pro Gly Val Glu Lys
                260                 265                 270
Thr Met Lys Glu Ala Asp Ala Val Ile Ala Leu Ala Pro Val Phe Asn
                275                 280                 285
Asp Tyr Ser Thr Thr Gly Trp Thr Asp Ile Pro Asp Pro Lys Lys Leu
        290                 295                 300
Val Leu Ala Glu Pro Arg Ser Val Val Asn Gly Ile Arg Phe Pro
305                 310                 315                 320
Ser Val His Leu Lys Asp Tyr Leu Thr Arg Leu Ala Gln Lys Val Ser
                325                 330                 335
Lys Lys Thr Gly Ala Leu Asp Phe Phe Lys Ser Leu Asn Ala Gly Glu
            340                 345                 350
Leu Lys Lys Ala Ala Pro Ala Asp Pro Ser Ala Pro Leu Val Asn Ala
        355                 360                 365
Glu Ile Ala Arg Gln Val Glu Ala Leu Leu Thr Pro Asn Thr Thr Val
    370                 375                 380
Ile Ala Glu Thr Gly Asp Ser Trp Phe Asn Ala Gln Arg Met Lys Leu
385                 390                 395                 400
Pro Asn Gly Ala Arg Val Glu Tyr Glu Met Gln Trp Gly His Ile Gly
                405                 410                 415
Trp Ser Val Pro Ala Ala Phe Gly Tyr Ala Val Gly Ala Pro Glu Arg
                420                 425                 430
Arg Asn Ile Leu Met Val Gly Asp Gly Ser Phe Gln Leu Thr Ala Gln
            435                 440                 445
Glu Val Ala Gln Met Val Arg Leu Lys Leu Pro Val Ile Ile Phe Leu
        450                 455                 460
```

Ile Asn Asn Tyr Gly Tyr Thr Ile Glu Val Met Ile His Asp Gly Pro
465                 470                 475                 480

Tyr Asn Asn Ile Lys Asn Trp Asp Tyr Ala Gly Leu Met Glu Val Phe
            485                 490                 495

Asn Gly Asn Gly Gly Tyr Asp Ser Gly Ala Gly Lys Gly Leu Lys Ala
        500                 505                 510

Lys Thr Gly Gly Glu Leu Ala Glu Ala Ile Lys Val Ala Leu Ala Asn
    515                 520                 525

Thr Asp Gly Pro Thr Leu Ile Glu Cys Phe Ile Gly Arg Glu Asp Cys
    530                 535                 540

Thr Glu Glu Leu Val Lys Trp Gly Lys Arg Val Ala Ala Ala Asn Ser
545                 550                 555                 560

Arg Lys Pro Val Asn Lys Leu Leu
            565

<210> SEQ ID NO 35
<211> LENGTH: 1152
<212> TYPE: DNA
<213> ORGANISM: Zymomonas mobilis

<400> SEQUENCE: 35
atggcttctt caactttta tattcctttc gtcaacgaaa tgggcgaagg ttcgcttgaa       60
aaagcaatca aggatcttaa cggcagcggc tttaaaaatg cgctgatcgt ttctgatgct      120
ttcatgaaca atccggtgt tgtgaagcag gttgctgacc tgttgaaagc acagggtatt      180
aattctgctg tttatgatgg cgttatgccg aacccgactg ttaccgcagt tctggaaggc      240
cttaagatcc tgaaggataa caattcagac ttcgtcatct ccctcggtgg tggttctccc      300
catgactgcg ccaaagccat cgctctggtc gcaaccaatg gtggtgaagt caaagactac      360
gaaggtatcg acaaatctaa gaaacctgcc ctgcctttga tgtcaatcaa cacgacggct      420
ggtacggctt ctgaaatgac gcgtttctgc atcatcactg atgaagtccg tcacgttaag      480
atggccattg ttgaccgtca cgttaccccg atggtttccg tcaacgatcc tctgttgatg      540
gttggtatgc caaaaggcct gaccgccgcc accggtatgg atgctctgac ccacgcattt      600
gaagcttatt cttcaacggc agctactccg atcaccgatg cttgcgcctt gaaggctgcg      660
tccatgatcg ctaagaatct gaagaccgct tgcgacaacg gtaaggatat gccagctcgt      720
gaagctatgg cttatgccca attcctcgct ggtatggcct tcaacaacgc ttcgcttggt      780
tatgtccatg ctatggctca ccagttgggc ggctactaca acctgccgca tggtgtctgc      840
aacgctgttc tgcttccgca tgttctggct tataacgcct tgtcgttgc tggtcgtctg      900 aaagacgttg gtgttgctat gggtctcgat atcgccaatc tcggtgataa agaaggcgca      960
gaagccacca ttcaggctgt tcgcgatctg gctgcttcca ttggtattcc agcaaatctg     1020
accgagctgg gtgctaagaa agaagatgtg ccgcttcttg ctgaccacgc tctgaaagat     1080
gcttgtgctc tgaccaaccc gcgtcagggt gatcagaaag aagttgaaga actcttcctg     1140
agcgctttct aa                                                         1152

<210> SEQ ID NO 36
<211> LENGTH: 383
<212> TYPE: PRT
<213> ORGANISM: Zymomonas mobilis

<400> SEQUENCE: 36

Met Ala Ser Ser Thr Phe Tyr Ile Pro Phe Val Asn Glu Met Gly Glu
1               5                   10                  15

```
Gly Ser Leu Glu Lys Ala Ile Lys Asp Leu Asn Gly Ser Gly Phe Lys
             20                  25                  30

Asn Ala Leu Ile Val Ser Asp Ala Phe Met Asn Lys Ser Gly Val Val
             35                  40                  45

Lys Gln Val Ala Asp Leu Leu Lys Ala Gln Gly Ile Asn Ser Ala Val
 50                  55                  60

Tyr Asp Gly Val Met Pro Asn Pro Thr Val Thr Ala Val Leu Glu Gly
 65                  70                  75                  80

Leu Lys Ile Leu Lys Asp Asn Asn Ser Asp Phe Val Ile Ser Leu Gly
             85                  90                  95

Gly Gly Ser Pro His Asp Cys Ala Lys Ala Ile Ala Leu Val Ala Thr
             100                 105                 110

Asn Gly Gly Glu Val Lys Asp Tyr Glu Gly Ile Asp Lys Ser Lys Lys
             115                 120                 125

Pro Ala Leu Pro Leu Met Ser Ile Asn Thr Thr Ala Gly Thr Ala Ser
130                 135                 140

Glu Met Thr Arg Phe Cys Ile Ile Thr Asp Glu Val Arg His Val Lys
145                 150                 155                 160

Met Ala Ile Val Asp Arg His Val Thr Pro Met Val Ser Val Asn Asp
                 165                 170                 175

Pro Leu Leu Met Val Gly Met Pro Lys Gly Leu Thr Ala Ala Thr Gly
                 180                 185                 190

Met Asp Ala Leu Thr His Ala Phe Glu Ala Tyr Ser Ser Thr Ala Ala
             195                 200                 205

Thr Pro Ile Thr Asp Ala Cys Ala Leu Lys Ala Ala Ser Met Ile Ala
             210                 215                 220

Lys Asn Leu Lys Thr Ala Cys Asp Asn Gly Lys Asp Met Pro Ala Arg
225                 230                 235                 240

Glu Ala Met Ala Tyr Ala Gln Phe Leu Ala Gly Met Ala Phe Asn Asn
                 245                 250                 255

Ala Ser Leu Gly Tyr Val His Ala Met Ala His Gln Leu Gly Gly Tyr
             260                 265                 270

Tyr Asn Leu Pro His Gly Val Cys Asn Ala Val Leu Leu Pro His Val
             275                 280                 285

Leu Ala Tyr Asn Ala Ser Val Val Ala Gly Arg Leu Lys Asp Val Gly
290                 295                 300

Val Ala Met Gly Leu Asp Ile Ala Asn Leu Gly Asp Lys Glu Gly Ala
305                 310                 315                 320

Glu Ala Thr Ile Gln Ala Val Arg Asp Leu Ala Ala Ser Ile Gly Ile
                 325                 330                 335

Pro Ala Asn Leu Thr Glu Leu Gly Ala Lys Lys Glu Asp Val Pro Leu
             340                 345                 350

Leu Ala Asp His Ala Leu Lys Asp Ala Cys Ala Leu Thr Asn Pro Arg
             355                 360                 365

Gln Gly Asp Gln Lys Glu Val Glu Glu Leu Phe Leu Ser Ala Phe
370                 375                 380
```